US009155723B2

(12) United States Patent
Jain et al.

(10) Patent No.: US 9,155,723 B2
(45) Date of Patent: Oct. 13, 2015

(54) ANTI-CXCR4 AS A SENSITIZER TO CANCER THERAPEUTICS

(75) Inventors: Rakesh K. Jain, Wellesley, MA (US); Dan G. Duda, Belmont, MA (US); Sergey V. Kozin, Cambridge, MA (US); Dai Fukumura, Newton, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 13/806,929

(22) PCT Filed: Jun. 28, 2011

(86) PCT No.: PCT/US2011/042185

§ 371 (c)(1), (2), (4) Date: Feb. 21, 2013

(87) PCT Pub. No.: WO2012/047339

PCT Pub. Date: Apr. 12, 2012

(65) Prior Publication Data

US 2013/0216531 A1 Aug. 22, 2013

Related U.S. Application Data

(60) Provisional application No. 61/359,138, filed on Jun. 28, 2010.

(51) Int. Cl.

| | |
|---|---|
| ***G01N 33/53*** | (2006.01) |
| ***A61K 31/395*** | (2006.01) |
| ***A61K 45/06*** | (2006.01) |
| ***A61K 31/404*** | (2006.01) |
| ***A61K 31/44*** | (2006.01) |
| ***A61K 31/517*** | (2006.01) |
| ***A61K 39/395*** | (2006.01) |
| *A61K 38/00* | (2006.01) |

(52) U.S. Cl.

CPC ............ *A61K 31/395* (2013.01); *A61K 31/404* (2013.01); *A61K 31/44* (2013.01); *A61K 31/517* (2013.01); *A61K 39/3955* (2013.01); *A61K 45/06* (2013.01); *A61K 38/00* (2013.01)

(58) Field of Classification Search

None

See application file for complete search history.

(56) References Cited

U.S. PATENT DOCUMENTS

| | | | | |
|---|---|---|---|---|
| 2003/0148940 | A1 | 8/2003 | Tudan et al. | |
| 2010/0178271 | A1 | 7/2010 | Bridger et al. | |
| 2011/0091486 | A1* | 4/2011 | Brown et al. | 424/174.1 |
| 2013/0039882 | A1* | 2/2013 | Kim et al. | 424/85.1 |

OTHER PUBLICATIONS

Kioi et al (Journal Clinical Investigation, Mar. 2010, 120:694-705, published online Feb. 22, 2010).*

Redjal et al (Clinical Cancer Research, 2006, 12:6765-6771).*

Rubin et al (PNAS, 2003, 100:13513-13518).*

Maderna et al (Cancer Biology and Therapy, 2007, 6:1018-1024).*

Salmaggi et al (J Neuro-Oncology, 2004, 67:305-317).*

Dawson et al., Author Manuscript of Nature, 461:(7262):E4-E5 (2009). "VEGFR1-activity-independent metastasis formation."

Du et al., Cancer Cell, 13:206-220 with Supplemental Data Figures S1-S4 (2008). "HIF1α Induces the Recruitment of Bone Marrow-Derived Vascular Modulatory Cells to Regulate Tumor Angiogenesis and Invasion."

Lapteva et al., Cancer Gene Therapy, 12:84-89 (2005). "CXCR4 knockdown by small interfering RNA abrogates breast tumor growth in vivo."

Liang et al., Author Manuscript of Biochem Biophys Res Commun, 359(3):716-722 (2007). "CXCR4/CXCL12 axis promotes VEGF-mediated tumor angiogenesis through Akt signaling pathway."

Shaked et al., Cancer Cell, 14:263-273 with Supplemental Data Table S1 and Figures S1-S6 (2008). "Rapid Chemotherapy-Induced Acute Endothelial Progenitor Cell Mobilization: Implications for Antiangiogenic Drugs as Chemosensitizing Agents."

Shaked et al., Science, 313:1785 (2006). "Therapy-Induced Acute Recruitment of Circulating Endothelial Progenitor Cells to Tumors."

Staller et al., 425:307-311 with Supplemental Data Figure S1 and Tables S2-S5 (2003). "Chemokine receptor CXCR4 downregulated by von Hippel-Lindau tumour suppressor pVHL."

Xu et al., Cancer Res, 69(20):7905-7910 (2009). "Direct Evidence that Bevacizumab, an Anti-VEGF Antibody, Up-regulates SDF1α, CXCR4, CXCL6, and Neuropilin 1 in Tumors from Patients with Rectal Cancer."

Zeng et al., 113(24):6215-6224 with Supplemental Data Figures S1-S4 (2009). "Targeting the leukemia microenvironment by CXCR4 inhibition overcomes resistance to kinase inhibitors and chemotherapy in AML."

* cited by examiner

*Primary Examiner* — Laura B Goddard

(74) *Attorney, Agent, or Firm* — Nixon Peabody LLP; David S. Resnick; Nicole D. King

(57) ABSTRACT

Inhibition of CXCR4 can inhibit tumor growth and metastasis during certain therapeutic windows. Disclosed are novel methods for treating and preventing cancer in a subject related to administration of CXCR4 inhibitors during a therapeutic window following treatment with another anti-tumor therapy.

18 Claims, 21 Drawing Sheets

ANTI-CXCR4 AS A SENSITIZER TO CANCER THERAPEUTICS

GOVERNMENT SUPPORT

This invention was made with Government support under R01-CA115767, P01-CA80124, R01-CA126642, R01-CA085140, R21-CA139168, R01-CA096915 and Proton Beam Federal Share Grants awarded by the National Institutes of Health and under W81XWH-10-1-0016 awarded by the Department of Defense. The Government has certain rights in the invention.

CROSS REFERENCE TO RELATED APPLICATIONS

This application is a 35 U.S.C. 371 National Stage Application of International Application No. PCT/US2011/042185 filed on Jun. 28, 2011, which designates the United States, and which claims benefit under 35 U.S.C. §119(e) of the U.S. Provisional Application Ser. No. 61/359,138 filed on Jun. 28, 2010, the contents of which are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jul. 25, 2011, is named 30258PCT.txt and is 19,056 bytes in size.

FIELD OF THE INVENTION

The present invention relates to novel methods for the treatment of cancer by administering anti-CXCR4 therapeutics.

BACKGROUND OF THE INVENTION

In the U.S. alone, cancer affects approximately 11.7 million adults and children, and this year, more than 1.5 million new cases will be diagnosed (American Cancer Society. Cancer Facts & Figures 2011. Atlanta: American Cancer Society; 2011). Over 500,000 Americans are expected to die from cancer in 2011, more than 1,300 people per day.

Currently, cancer therapy involves surgery, chemotherapy and/or radiation treatment or eradicate cancerous cells in a patient (see, for example, Stockdale, 1998, "Principles of Cancer Patient Management", in Scientific American: Medicine, vol. 3, Rubenstein and Federman, eds., Chapter 12, Section IV). All of these approaches pose significant drawbacks for the patient. Surgery, for example, can be contraindicated due to the health of the patient or can be unacceptable to the patient. Additionally, surgery might not completely remove the neoplastic tissue. Radiation therapy is effective only when the irradiated cancerous tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in Scientific American Medicine, vol. 3, Rubenstein and Federman, eds., ch. 12, sect. 10). Almost all chemotherapeutic agents are toxic, and chemotherapy can cause significant, and often dangerous, side effects, including severe nausea, bone marrow depression, immunosuppression, etc. Additionally, many tumor cells are resistant or develop resistance to chemotherapeutic agents through multi-drug resistance.

The development of novel or improved therapies focuses on preventing angiogenesis, growth or regrowth and metastasis of tumors as these are key processes that must be halted in order to successfully treat or cure a cancer. These processes can be promoted by bone marrow-derived cells (BMDCs), e.g. myelomonocytes and macrophages which have migrated into the tumor or the surrounding tissue. Recruitment of BMDCs to a tumor can be triggered by certain chemotherapeutics, vascular disruption treatments, or radiation therapy (Shaked Y, Ciarrocchi A, Franco M, et al. Science 2006; 313:1785-7 Shaked Y, Henke E, Roodhart J M, et al, Cancer Cell 2008; 14:263-73). One mechanism believed to drive recruitment of BMDCs to tumors is the CXCR4-CXCL12 signal pathway. CXCR4 is the receptor for CXCL12 and is suspected of controlling cancer cell migration and metastasis as well as BDMC infiltration into tissues[14].

An increased understanding of the kinetics and mechanisms of the CXCR4-CXCL12 pathway and its promotion of BMDC infiltration of tumors will enable more effective therapies, improved combination therapy strategies, and allow lower and fewer doses of anti-cancer treatments without compromising efficacy, thereby avoiding the detrimental side effects of chemotherapy and radiation therapy.

SUMMARY OF THE INVENTION

Described herein is the discovery that the recruitment of certain hematopoietic/immune BMDCs, i.e. myelomonocytes and macrophages promotes tumor and endothelial cell survival, tumor regrowth, and metastasis and that an effective therapeutic treatment window exists in which CXCR4 inhibitors can be administered to a patient in order to prevent BMDC infiltration of a tumor. As further demonstrated herein, administration of a CXCR4 inhibitor was effective in suppressing tumor regrowth, angiogenesis, and metastasis if administered within 5 days of local irradiation but was ineffective after that time.

Accordingly, aspects of the invention described herein are related to a method of treating or preventing a cancer tumor in a subject in need thereof, comprising: (a) administering an anti-tumor therapy to the subject; and (b) administering a therapeutically effective amount of a CXCR4 inhibitor to the subject within 5 days of administering the anti-tumor therapy.

Aspects of the invention described herein are related to a method of treating or preventing metastasis of a cancer tumor in a subject in need thereof, comprising: (a) administering an anti-tumor therapy to the subject; and (b) administering a therapeutically effective amount of a CXCR4 inhibitor to the subject within 5 days of administering the anti-tumor therapy.

The inventors have also demonstrated herein that CXCL12 is upregulated during the above-referenced therapeutic window in the cancer cells of subject that has been administered an anti-tumor therapy. Accordingly, aspects of the invention described herein are related to a method of treating or preventing a cancer tumor in a subject in need thereof, comprising: (a) administering an anti-tumor therapy to the subject; (b) measuring the level of CXCL12 expression in the subject; (c) comparing the level of CXCL12 expression in the subject to a reference level; and (d) administering a therapeutically effective amount of a CXCR4 inhibitor to the subject until CXCL12 expression is within 10% of the reference level. Aspects of the invention described herein are related to a method of treating or preventing metastasis of a cancer tumor in a subject in need thereof, comprising: (a) administering an anti-tumor therapy to the subject; (b) measuring the level of CXCL12 expression in the subject; (c) comparing the level of CXCL12 expression in the subject to a reference level; and (d) administering a therapeutically effective amount of a CXCR4 inhibitor to the subject until CXCL12 expression is within 10% of the reference level.

In some embodiments, the CXCR4 inhibitor is selected from the group consisting of small organic or inorganic molecules; polysaccharides; peptides; polypeptides; proteins; antibodies; peptide analogs and derivatives; peptidomimetics; nucleic acids; nucleic acid analogs and derivatives; an extract made from biological materials such as bacteria, plants, fungi, animal cells, or tissues; and any combinations thereof.

In some embodiments the CXCR4 inhibitor is selected from the group consisting of 1,1'-[1,4-phenylene-bis(methylene)]-bis-1,4,8,11-tetraazacyclotetradecane (AMD-3100); Mozobil; Plerixafor; NOXA12; CTCE-9908; ALX40-4C; T22; T140; Met-SDFlbeta (Met-SDF-1β); T134; AMD-3465; N'-(1-Hbenzimidazol-2-ylmethyl)-N1-(5,6,7,8-tetrahydroquinoline-8-yl)-butane-1,4-diamine; CTCF-0214; CTCF-9908; CP-1221 (linear peptides, cyclic peptides, natural amino-acids, unnatural amino acids, and peptidomimetic compounds); 4F-benzoylTN24003; KRH-1120; KRH-1636; KRH-2731; polyphemusin analogue; ALX40-4C; T-140; T-140 analogs and derivatives; TN14003; TC14012; TE14011; and any combinations thereof.

In some embodiments, the anti-tumor therapy is selected from the group consisting of radiation therapy, chemotherapy, antiangiogenic therapy, and any combinations thereof.

In some embodiments, the anti-tumor therapy increases the expression of CXCL12 by at least 10%. In some embodiments, the antitumor therapy comprises administering a VEGF inhibitor. In some embodiments, the VEGF inhibitor is selected from the group consisting of ABT-869: AEE-788; AG-13736; AG-028262; Angiostatin; bevacizumab; AVE-8062; AZD-2171; sorafenib; BMS-387032; CEP-7055; CHIR-258; GFKI; CP-547632; CP-564959; E-7080; 786034; GW-654652; IMC-1C11; KRN-951; PKC-412; PTK-787; SU11248; SU-5416; SU-6668; AVE-0005; thalidomide; XL-647; XL-999; ZD-6474; ZK-304709; Pazopanib; CDP791; Enzastaurin; BIBF 1120; BAY 573952; BAY 734506; XL 184; IMC-1121B; CEP 701; SU 014813; SU 10944; SU 12662; OSI-930; BMS 582664; ZD-6126; Imatinib; Glivec; Gleevec; STI-571; CGP-57148; RAD-001; BMS-354825; Volociximab; CCI-779; 17-AAG; DMXAA; CI-1040; CI-1033; (5-[5-fluoro-2-oxo-1,2-dihydroindol (3Z)-ylidenemethyl]-2,4-dimethyl-1H-pyrrole-3-carboxylic acid [2-diethylaminoethyl]amide); 4TBPPAPC; AMG 706; Nexavar®; and PTK/ZK.

In some embodiments, the anti-tumor therapy comprises administering a chemotherapeutic agent.

In some embodiments, the anti-tumor therapy comprises administering a p38 MAPK inhibitor. In some embodiments, the p38 MAPK inhibitor is selected from the group consisting of antisense p38 MAPK nucleic acids and fragments thereof, antibodies that bind p38 MAPK and fragments thereof, EO-1428, SB239063, SB281832, VX-702, VX-745, ZM336372, RPR 200765A, N-(3-tert-butyl-1-methyl-5-pyrazolyl)N'-(4-(4-pyridinylmethyl)phenyl)urea, SB203580, SB202190, PD169316, fr-167653, trans-1-(4-hydroxycyclohexyl)-4-(4-fluorophenyl)-5-(2 methoxypyridimidin-4-yl)imidazole, 2-(4-Chlorophenyl)-4-)4-fluorophenyl)-5-pyridin-4-yl-1,2-dihydropyrazol-3-one, and any combinations thereof.

In some embodiments, the cancer is selected from the group consisting of basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome In some embodiments, the CXCR4 inhibitor administration is systemic administration. In some embodiments, the CXCR4 inhibitor administration is by injection, infusion, instillation, inhalation, or ingestion. In some embodiments, the injection is intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, or intrasternal injection.

In some embodiments, the therapeutically effective amount of the CXCR4 inhibitor is 1 μg/kg to 150 mg/kg of bodyweight.

In some embodiments, the CXCR4 inhibitor is administered daily. In some embodiments, the CXCR4 inhibitor is administered for at least 1 day. In some embodiments, the CXCR4 inhibitor is administered for at least one week.

In some embodiments, the subject to be administered a CXCR4 inhibitor according to the methods provided herein is selected as suffering from a cancer tumor prior to administering the anti-tumor therapy and the CXCR4 inhibitor.

In some embodiments, the subject to be administered a CXCR4 inhibitor according to the methods provided herein is selected as being in need of treatment to prevent of metastasis of a cancer tumor prior to administering the anti-tumor therapy and the CXCR4 inhibitor.

In some embodiments, the subject is a mammal. In some embodiments, the subject is a human.

BRIEF DESCRIPTION OF THE FIGURES

FIG. 1A shows primary tumor growth is transient (i.e., at day 10) in BMT-CXCR4$^{-/-}$ mice (CXCR4-KO) in TRAMP-C1 and E0771 models. Both tumors grew significantly slower in BMT-CXCR4$^{-/-}$ VEGFR1$^{TK-/-}$ (CXCR4/TK-KO) mice compared with control [BMT-CXCR4$^{flox/+}$ VEGFR1 TK$^{+/+}$ mice: control BMT (Ctrl BMT)]. FIGS. 1B and 1C demonstrate lung metastatic burden at 4 wk after primary tumor removal (i.e., number and volume of macrometastases) is substantially decreased by genetic deletion of CXCR4 in BMDCs in TRAMP-C1 (1B) and E0771 (1C) tumors in CXCR4-KO and CXCR4/TK-KO mice compared with Ctrl BMT mice. *P<0.05 compared with control; error bars represent mean±SEM.

FIGS. 2A and 2B show tumor vascular density (2A) and myeloid BMDC infiltration (2B) are decreased in both TRAMP-C1 and E0771 models in BMT-CXCR4$^{-/-}$ mice (CXCR4-KO) and in BMT-CXCR4$^{-/-}$ VEGFR1$^{TK-/-}$ (CXCR4/TK-KO) mice compared with control [BMT-CXCR4$^{flox/+}$VEGFR1$^{TK+/+}$ mice: control (Ctrl BMT)]. FIGS. 2C and 2D show Gr-1+ BMDC infiltration is decreased in both tumors in mice with CXCR4$^{-/-}$ BMDCs, irrespective of VEGFR1-TK status (2C). Conversely, tumor-associated macrophage (TAM) infiltration is decreased only in mice with VEGFR1TK$^{-/-}$ BMDCs (2D). *P<0.05 compared with control; error bars represent mean±SEM.

FIGS. 3A and 3B show in a preventive setting: Early tumor growth is transiently inhibited by CXCR4 blockade with AMD3100 pumps (AMD) started from the time of tumor implantation in C57BL/6 mice (WT) and moderately delayed in BMT-VEGFR1$^{TK-/-}$ (TK) mice in both TRAMP-C1 (3A) and E0771 (3B) models. However, a more significant tumor growth delay is seen with AMD3100 in TK mice. FIG. 3C shows in an intervention setting: after 28 d of AMD3100 treatment of established TRAMP-C1 tumors, a significant growth delay was seen only in TK mice. FIGS. 3D and 3E demonstrate that AMD3100 treatment significantly decreases the number and volume of lung metastases at 4 wk after tumor resection only in TRAMP-C1 tumors (3D). In E0771 tumors, a significant decrease in metastatic burden is seen after AMD3100 treatment only in TK mice (3E). *P<0.05 compared with control PBS (WT); error bars represent mean±SEM.

FIGS. 4A and 4B show AMD3100 treatment (AMD) decreases tumor vascular density (4A) and myeloid BMDC infiltration (4B) in both TRAMP-C1 and E0771 models only in BMT-VEGFR1$^{TK-/-}$ (TK) mice but not in C57BL/6 mice (WT). CXCR4 or VEGFR1-TK inhibition alone decreases vascular density and myeloid BMDC number only in E0771 tumors. FIG. 4C shows AMD3100 treatment decreases Gr-1$^{+}$ BMDC infiltration irrespective of VEGFR1-TK status. FIG. 4D shows that conversely, TAM infiltration is decreased only in mice with VEGFR1$^{TK-/-}$ BMDCs. *P<0.05 compared with control PBS (WT); error bars represent mean±SEM.

FIG. 5A shows myeloid BMDC migration: VEGF and CXCL12 independently increase migration of CD11b$^{+}$ BMDCs. FIGS. 5B and 5C show p38 MAPK activity: Exposure to recombinant (r)VEGF, rPlGF (both VEGFR1 ligands), or rCXCL12 (CXCR4 ligand) increased phospho-P38 MAPK in myeloid BMDCs (5B); this increase was specifically abrogated by the inhibition of VEGFR1-TK (in TK-KO cells) or CXCR4 using AMD3100 (AMD), respectively (5C). FIG. 5D shows a role of p38 MAPK in myeloid BMDC migration: The p38 MAPK inhibitor SB203580 decreased migration of myeloid BMDCs in response to either rVEGF or rCXCL12. FIGS. 5E and 5F show migration of specific myeloid BMDC subsets: VEGF increased the migration of F4/80$^{+}$ BMDCs (5E) but not of Gr1$^{+}$ BMDCs (5F), and this effect was abrogated by VEGFR1-TK inhibition (5E). rCXCL12 specifically increased the migration of Gr-1$^{+}$ BMDCs, and this effect was reversed by CXCR4 but not by VEGFR1-TK inhibition. V, rVEGF; P, rPlGF, C, rCXCL12; *P<0.05 compared with control (N); error bars represent mean±SEM.

FIG. 9A depicts the experimental design: tumors received the same total radiation dose (21 Gy) over the same period of time, either by LI and WBI or by two fractions of LI. B and C, WBI significantly delayed tumor regrowth after radiation therapy in both 54A (FIG. 9B) and MCa8 (FIG. 9C) models, and this effect was abrogated by the infusion of bone marrow cells from nonirradiated donors (n=7-9; *, P<0.05). FIG. 9D, at higher LI doses, the addition of WBI (n=21) significantly enhanced the local control probability (>90 d) of 54A tumor compared with LI alone (n=22, P<0.05).

FIG. 10A depicts quantification of CXCL12 expression before and 2 d after 20 Gy of radiation. Irradiation induced a significant increase in SDF-1$\alpha$. FIG. 10B and FIG. 10C demonstrate the effect of CXCR4 blockade using AMD3100 on tumor regrowth after irradiation of 54A (FIG. 10B) and MCa8 (FIG.

10C) tumors. CXCR4 blockade delayed tumor growth when commenced immediately after but not 5 d after irradiation (n=6-8; *, P<0.05).

Figure 11:
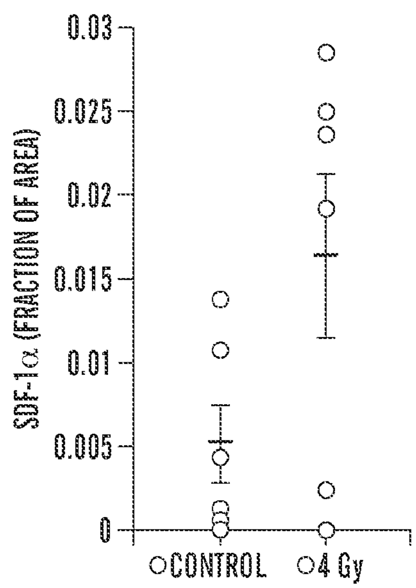

FIG. 11 depicts CXCL12 (SDF-1α) expression in MCa8 tumor two days after one fraction of 4 Gy of local irradiation. There is a tendency for rapid increase in CXCL12 expression in the tumor tissue even after this low dose of local irradiation (p=0.08).

Figure 12:
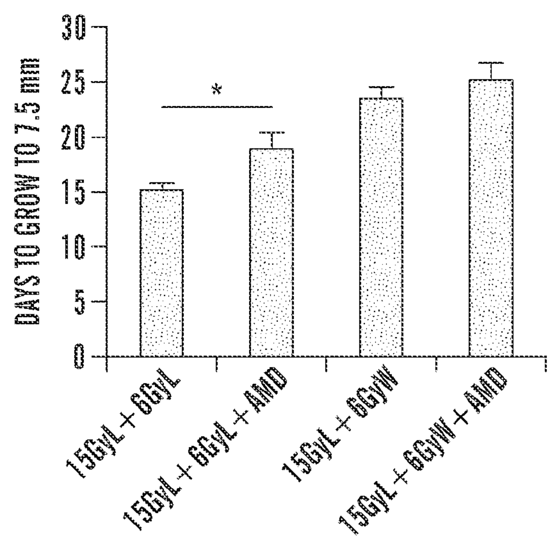

FIG. 12 demonstrates the anti-tumor effects of local (15 GyL+6 GyL) and mixed local and whole-body (15 GyL+6 GyW) irradiation, alone or followed by AMD3100 (AMD) treatment, in mice with MCa8 mammary carcinoma. As previously shown (see FIGS. 10A-10C), AMD treatment commenced immediately after local irradiation induced a statistically significant delay of tumor growth, compared to local irradiation alone (*denotes p<0.05). However, combination of AMD with mixed 15 GyL+6 GyW irradiation induced no significant additional tumor growth delay.

Figure 13A:
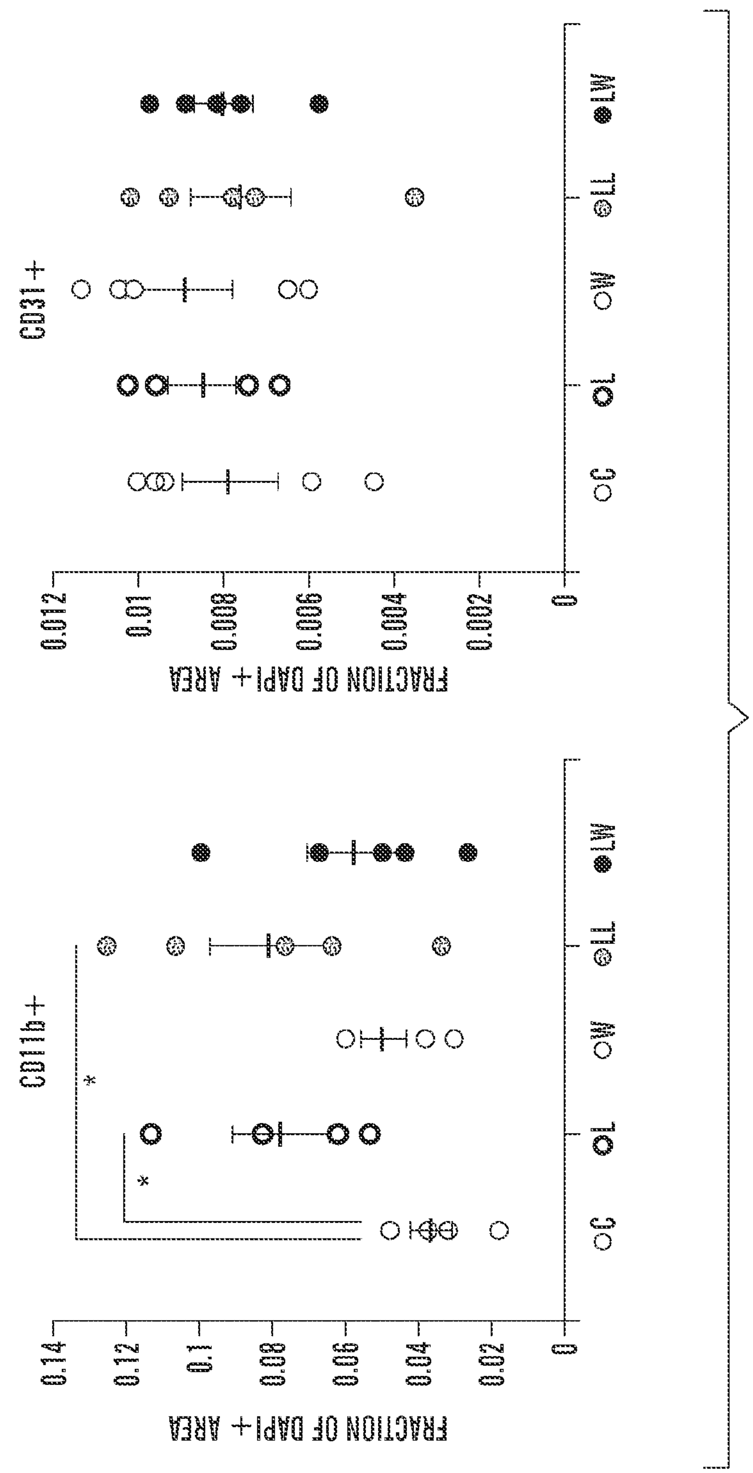
Figure 13C:
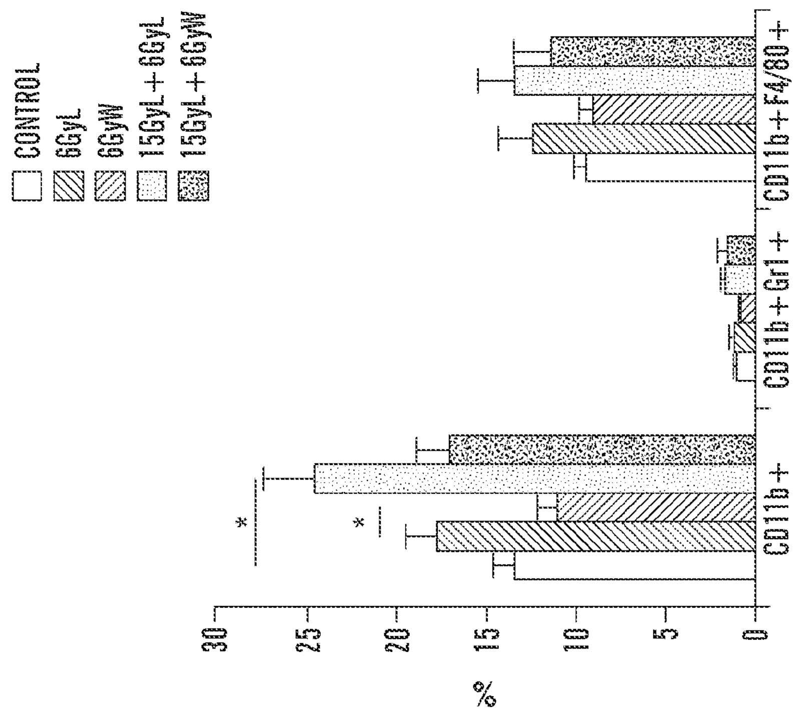
Figure 13B:
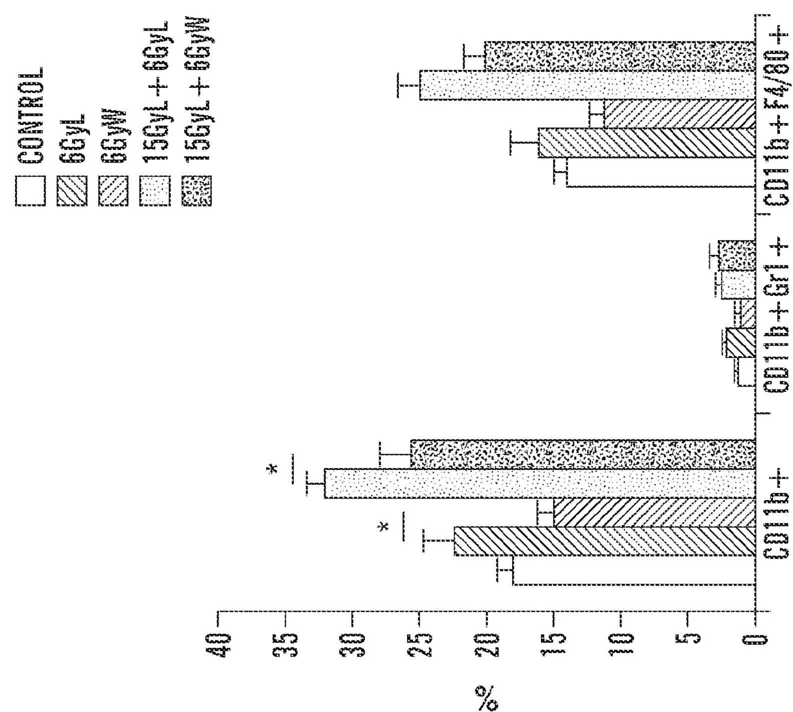

FIGS. 13A-13C indicate BMDC infiltration into tumors 3 d postirradiation. FIG. 13A depicts immunohistochemistry for CD11b and CD31 expression in 54A tumors. LI significantly increased the number of $CD11b^+$ myeloid BMDCs compared with control tumors, whereas the inclusion of WBI abrogated this effect. No significant difference was seen in microvascular density measured by CD31 expression. C=control; L=6 GyL; W=6 GyW; LL=15 GyL+6 GyL; LW=15 GyL+6 GyW. W=whole body irradiation, L=local irradiation. FIG. 13B-13C depict flow cytometry analysis of whole tumor lysates confirmed the changes in myeloid BMDCs after LI and WBI (n=5). The majority of BMDCs were $F4/80^+$ TAMs in both 54A (FIG. 13B) and MCa8 (FIG. 13C) tumors (*, P<0.05). For FIGS. 13B and 13C, the first series of data is the control, the second series is 6 GyL, the third series is 6 GyW, the fourth series is 15 GyL+6 GyL, and the fifth series is 15 GyL+6 GyW.

Figure 14A:
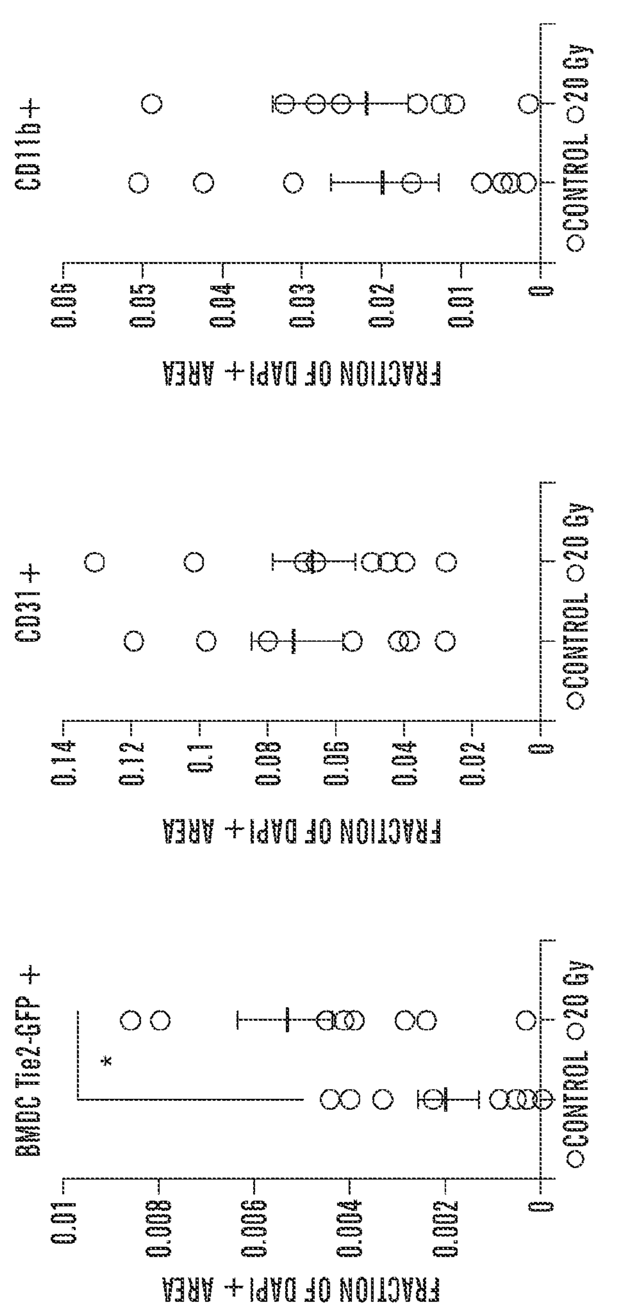
Figure 14B:
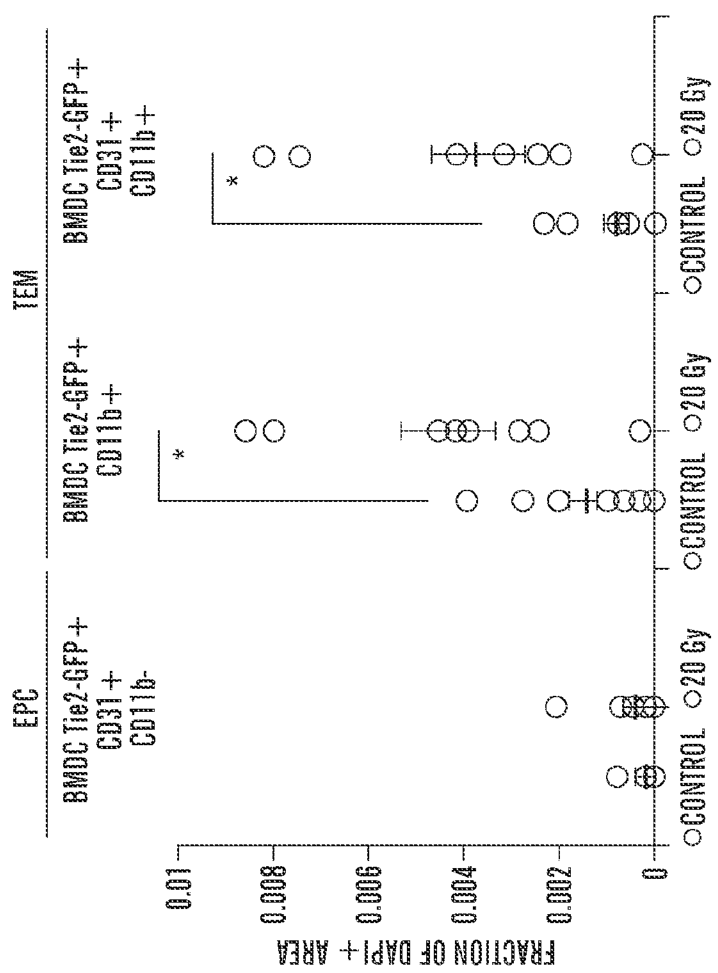

FIGS. 14A-14B depict analysis of BMDCs in tumors recurring after LI in wild-type/Tie2-GFP-BMT mice. Quantification of BMDCs: overall myeloid cell infiltration ($CD11b^+$) and $CD31^+$ microvascular density were not significantly changed, but the total number of $Tie2^+$ BMDCs increased in irradiated tumors (FIG. 14A). These represented mostly $Tie2^+CD11b^+$ or Tie2-expressing monocytes (TEMs), the majority of which were also $CD31^+$ but had perivascular location; in contrast, the number of vessel-incorporated $Tie2^+CD31^+CD11b^-$ EPCs was negligible and not different in tumors growing after irradiation (FIG. 14B; *, P<0.05).

DETAILED DESCRIPTION

The invention described herein generally relates to the discovery that recruitment of certain BMDCs, i.e. myelomonocytes and macrophages promotes tumor and endothelial cell survival, tumor regrowth, and metastasis and that an effective therapeutic treatment window exists in which CXCR4 inhibitors can be administered to a patient in order to prevent BMDC infiltration of a tumor. As demonstrated herein, increased expression of CXCL12 was detected in tumors 2 days after local irradiation of the tumor. As further demonstrated herein, administration of a CXCR4 inhibitor was effective in suppressing tumor regrowth, angiogenesis, and metastasis if administered within 5 days of local irradiation but was ineffective after that time.

The inventors also demonstrate herein that CXCR4 and VEGF promote angiogenesis via independent pathways and that administration of both a VEGF inhibitor and a CXCR4 inhibitor is required to prevent growth, angiogenesis, and metastasis in some tumors. Finally, the inventors demonstrate herein that CXCR4 is particularly effective in preventing metastasis. In some embodiments, administration of both a VEGF inhibitor and a CXCR4 inhibitor to a subject can inhibit metastasis of a breast cancer. In some embodiments, administration of both a VEGF inhibitor and a CXCR4 inhibitor to a subject is required to inhibit lung metastasis. In some embodiments, administration of a CXCR4 inhibitor to a subject can inhibit metastasis or growth of a prostate cancer.

Accordingly, provided herein, in part, are methods for the treatment and prevention of a cancer in a subject in need thereof. In some embodiments, the methods comprise treating the subject with an anti-tumor therapy and administering a CXCR4 inhibitor within the therapeutic window described herein. In some embodiments, the methods comprise treating the subject with an anti-tumor therapy and administering a CXCR4 inhibitor to the subject within 5 days of administering the anti-tumor therapy.

Also provided herein, are methods for the treatment and prevention of a cancer which comprise (a) administering an anti-tumor therapy to a subject; (b) measuring the level of CXCL12 expression in the subject; and (c) administering a CXCR4 inhibitor to the subject until a decrease in CXCL12 expression is detected.

The term "CXCR4", as used herein, shall be understood to refer to the CXCR4 chemokine receptor, a receptor in the GPCR (G-protein coupled receptor) gene family, which is expressed by cells in the bone marrow, immune system and the central nervous system. In response to binding its ligand CXCL12 or SDF-1α (stromal cell-derived factor-1α), CXCR4 is thought to trigger the migration and recruitment of immune cells, as well as the homing of stem cells (e.g., EPCs). The receptor is believed to enhance downstream signaling by several different pathways. As a GPCR, CXCR4 binding of CXCL12 activates G-protein mediated signaling, including downstream pathways such as ras, and PI3 kinase. PI3 kinase activated by CXCL12 and CXCR4 plays a role in lymphocyte chemotaxis in response to these signals. One endpoint of CXCR4 signaling is the activation of transcription factors such as AP-1 and chemokine regulated genes. JAK/STAT signaling pathways also appear to play a role in CXCL12/CXCR4 signaling.

Stromal derived factor-1α (SDF-1α, also called CXCL12) is a member of the CXC chemokine family and is highly conserved among species, including human and mouse. SDF-1α is produced by bone marrow stromal cells and also by epithelial cells in many other organs and has chemotactic activity for some cells of the hematopoietic lingeage (Aiuti, A. et al. (1997) /. *Exp. Med.* 185:111-20; Jo, D. Y. et al. (2000) /. *Clin. Invest.* 105:101-11; Nagasawa, T. et al. (1994) *Proc. Natl. Acad. Sci. USA* 91:2305-9; Nagasawa, T. (1996) *Proc. Natl. Acad. Sci. USA* 93:14726-9).

The sequence and structure of the human CXCR4 is known; see GenBank Accession Nos. NM 003467 and NM 001008540 for the nucleotide sequence and NP 003458 The nucleotide and polypeptide sequences of human SDF-1α are set forth in GenBank Accession Nos. NM_000609 and NP_000600, respectively. See Hwang, J. H. et al. (2003) *J. Clin. Endocrinol Metab.* 88(1): 408-416; Babcock, G. J. et al. (2003) *J. Biol. Chem.* 278(5): 3378-3385; Barbouche, R. et al. (2003) *J. Biol. Chem.* 278 (5):3131-3136; Adams, G. B. et al. (2003) *Blood* 101(1):4551; Lapham, C. K. et al. (2002) *J. Leukcoc. Biol.* 72(6): 12061214; Zhou, Y. et al. (2002) *J. Biol. Chem.* 277(51):4948149487; Sun, Y. et al. (2002) *J. Biol. Chem.* 277(51):4921249219; Bachelder, R. E. et al. (2002) *Cancer Res.* 62(24): 7203-7206; Barbero, S. et al. (2002) *Ann. NY. Acad. Sci.* 973:60-69; Rey, M. et al. (2002) *J. Immunol.* 169(10):54105414; Basmaciogullari, S. et al. (2002) *J.*

*Virol.* 76(21): 10791-10800; Konig, R. R. et al. (2002) *J. Virol.* 76(21): 10627-10636; Martinez-Caceres, E. M. et al. (2002) *Mult. Scler.* 8(5):390-395; Odemis, V. et al. (2002) *J. Biol. Chem.* 277(42):39801-39808; Moriuchi, M. et al. (2002) *J. Infect. Dis.* 186(8): 1194-1197; Kollet, O. et al. (2002) *Blood* 100(8): 2778-2786; Libura, J. et al. (2002) *Blood* 100(7): 2597-2606; Honczarenko, M. et al. (2002) *Blood* 100(7): 2321-2329; Ptasznik, A. et al. (2002) *J. Exp. Med.* 196(5): 667-678; Estes, J. D. et al. (2002) *J. Immunol.* 169(5):2313-2322; Farzan, M. et al. (2002) *J. Biol. Chem.* 277 (33):29484-29489; Fotopoulos, G. et al. (2002) *Proc. Natl. Acad. Sci. U.S.A.* 99(14):94109414; Peled, A. et al. (2002) *Stem Cells* 20(3):259-266; Habasque, C. (2002) *Mol. Hum. Reprod.* 8(5):419-425; Zhou, N. et al. (2002) *J. Biol. Chem.* 277(20): 17476-17485; Lu, M. et al. (2002) *Proc. Natl. Acad. Sci. U.S.A.* 99(10):7090-7095; Valenzuela-Fernandez, A. et al. (2002) *J. Biol. Chem.* 277 (18): 15677-15689; Schrader, A. J. et al. (2002) *Br. J. Cancer* 86(8):1250-1256; Nguyen, D. H. and Taub, D. (2002) *J. Immunol.* 168(8):4121-4126; Salvucci, O. et al. (2002) *Blood* 99(8):2703-2711; Juffermans, N. P. et al. (2002) *J. Infect. Dis.* 185(7):986-989; Taichman, R. S. et al. (2002) *Cancer Res.* 62(6):1832-1837; Zamarchi, R. et al. (2002) *Clin. Exp. Immunol.* 127(2):321-330; Arthos, J. et al. (2002) *Virology* 292(1): 98-106; Ferraro, G. A. et al. (2001) *AIDS Res. Hum. Retroviruses* 17(13):1241-1247; Ullrich, C. K. et al. (2000) *Blood* 96(4):1438-1442; Poznansky, M. C. et al. (2000) *Nat. Med.* 6(5):543-548; Secchiero, P. et al. (2000) *J. Immunol.* 164(8): 4018-4024; Cheng, Z. J. et al. (2000) *J. Biol. Chem.* 275(4): 2479-2485; Lalani, A. S. et al. (1999) *Science* 286(5446): 1968-1971; Sotsios, Y. et al. (1999) *J. Immunol.* 163(11): 5954-5963; Gupta, S. K. and Pillariseffi, K. (1999) *J. Immunol.* 163(5):2368-2372; Klein, R. S. et al. (1999) *J. Immunol.* 163(3): 1636-1646; Ling, K. et al. (1999) *Proc. Natl. Acad. Sci. U.S.A.* 96(14):7922-7927; Yasukawa, M. et al. (1999) *J. Immunol.* 162(9):5417-5422; Zou, Y. R. et al. (1998) *Nature* 393(6685):595-599; Tachibana, K. et al. (1998) *Nature* 393(6685):591-594; Caruz, A. et al. (1998) *FEBS Lett.* 426(2):271-278; Moriuchi, M. et al. (1997) *J. Immunol.* 159(9):4322-4329; Bleul, C. C. et al. (1996) *Nature* 382(6594):829-833; Choe, H. et al. (1996) *Cell* 85(7):11351148; Lu, Z. H. et al. (1995) *J. Biol. Chem.* 270 (44):2623926245; Loetscher, M. et al. (1994) *J. Biol. Chem.* 269(1):232237; Nomura, H. et al. (1993) *Int. Immunol.* 5(10): 12391249; Jazin, E. E. et al. (1993) *Regul. Pept.* 47(3):247-258; Herzog, H. et al. (1993) *DNA Cell Biol.* 12(6):465-471; Federsppiel, B. et al. (2993) *Genomics* 16(3):707-712 (1993); Bleul, C. C. et al. (1996) *Nature* 382(6594):829-33); Cheng, Z. et al. (2000) *J. Biol. Chem.* 275(4):2476-2485; Dutt, P. et al. (1998) *J. Immunology.* 161: 3652-3658; Wang, J. F. et al. (2000) *Blood* 95(8):2505-13; Ling K. et al. (1999) *Cell Biology* 96:7922-7927; Vicente-Manzanares, M. et al. (1999) *Immunology* 163:4001-12; Ganju, R. K. et al. (1998) *Biological Chemistry* 273(36):23169-175; and Zhang, X. F. et al. (2001) *Blood* 97(11):3342-3348; Glodek, A. M. et al. (2003) *J. Exp. Med.* 197(4):461-473; Roland, J. et al. (2003) *Blood* 101(2):399-406; Adamns, G. B. (2003) *Blood* 101(1):45-51; Sun, Y. et al. (2002) *J. Biol. Chem.* 277(51):49212-49219; Krug, A. et al. (2002) *J. Immunol.* 169(11):6079-6083; Barbero, S. et al. (2002) *Ann. N.Y. Acad. Sci.* 973:60-69; Nance, C. L. and Shearer, W. T. (2002) *Clin. Immunol.* 105(2):208-214; Libura, J. et al. (2002) *Blood* 100 (7):2597-2606; Honczarenko, M. (2002) *Blood* 100(7):23212329; Netelenbos, T. (2002) *J. Leukoc. Biol.* 72(2):353-362; Farzan, M. et al. (2002) *J. Biol. Chem.* 277(33):29484-29489; Okabe, S. et al. (2002) *E^. Hematol.* 30(7):761-766; Langford, D. (2002) *J Neuroimmunol.* 127(1-2):115-126; Inngjerdingen, M. et al. (2002) *Blood* 99(12):4318-4325; Lee, Y. (2002) 99(12):4307-4317; Peled, A. (2002) *Stem Cells* 20(3):259-266; Wright, N. et al. (2002) *J. Immunol.* 168(10): 5268-5277; Valenzuela-Fernandez, A. (2002) *J. Biol. Chem.* 277(18):15677-15689; Schrader, A. J. et al. (2002) *Br. J. Cancer* 86(8): 1250-1256; Salvucci, O. et al. (2002) *Blood* 99(8):2703-2711; Taichman, R. S. et al. (2002) *Cancer Res.* 62(6):1832-1837; Zaitseva, M. et al. (2002) *J. Immunol.* 168 (6):2609-2617; Casamayor-Palleja, M. et al. (2002) *Blood* 99(6): 1913-1921; Phillips, R. and Ager, A. (2002) *Eur. J. Immunol.* 32(3):837-847; Tresoldi, E. et al. (2002) *J. Infect. Dis.* 185(5):696-700; Riabov, G. S. et al. (2002) *Genetika* 38(2):278-280; Lataillade, J. J. et al. (2002) *Blood* 99(4): 1117-1129; Nanki, T. and Lipsky, P. E. (2001) *Cell. Immunol.* 214(2):145-154; Lathey, J. L. et al. (2001) *J. Infect. Dis.* 184(11):1402-1411; Bajetto, A. et al. (2001) *J. Neurochem.* 77(5): 1226-1236; Poznansky, M. C. et al. (2000) *Nat. Med.* 6(5):543-548; Ghezzi, S. et al. (2000) *Biochem. Biophys. Res. Commun.* 270(3):992-996; Cheng, Z. J. et al. (2000) *J. Biol. Chem.* 275(4):2479-2485; Luttichau, H. R. et al. (2000) *J. Exp. Med.* 191(1):171-180; Lalani, A. S. et al. (1999) *Science* 286(5446):1968-1971; Sotsios, Y. et al. (1999) *J. Immunol.* 163(11):5954-5963; Vicente-Manzanares, M. et al. (1999) *J. Immunol.* 163(7):4001-4012; Kozak, S. L. et al. (1999) *J. Biol. Chem.* 274(33):23499-23507; Su, S. B. et al. (1999) *J. Immunol.* 162(12):7128-7132; Weber, K. S. et al. (1999) *Mol. Biol. Cell* 10(4):861-873; Zaitseva, M. B. et al. (1998) *J. Immunol.* 161(6):3103-3113; Rubbert, A. et al. (1998) *J. Immunol.* 160(8):3933-3941; Bleul, C. C. et al. (1996) *Nature* 382(6594):829-833; and Shirozu, M. et al. (1995) *Genomics* 28(3):495-500; and references cited therein.

As used herein, "angiogenesis" refers to the formation of new blood vessels or the replacement of damaged blood vessels (e.g., capillaries).

CXCR4 Inhibitors

CXCR4 is also referred to as FB22; HM89; LAP3; LCR1; NPYR; WHIM; CD184; LESTR; NPY3R; NPYRL; HSY3RR; NPYY3R; or D2S201E.

As used herein, the term "CXCR4 inhibitor" refers to molecules and compositions that interfere with or inhibit the biological activity of the CXCR4 receptor. Biological activity of the CXCR4 receptor can include, but is not limited to, promoting migration of bone-marrow derived cells to a tumor, promoting migration of cells to a tissue expressing CXCL12, proliferation of hematopoietic stem cells, movement of thymocytes from the thymus, induction of neoplastic cell growth or uncontrolled cell growth, promotion of vascularizaion, promotion of hematopoiesis, promotion of myelopoiesis, and promotion of cardiac septum formation.

The CXCR4 inhibitors can encompass numerous classes of chemical molecules, e.g., small organic or inorganic molecules, polysaccharides, biological macromolecules, e.g., peptides, proteins, peptide analogs and derivatives, peptidomimetics, antibodies, antibody fragments, nucleic acids, nucleic acid analogs and derivatives, an extract made from biological materials such as bacteria, plants, fungi, or animal cells or tissues, naturally occurring or synthetic compositions.

In one embodiment, CXCR4 inhibitor is not a CXCR4 antibody or CXCR4 receptor binding fragment thereof.

In one embodiment, CXCR4 inhibitor is not an antagonist of CXCL12/SDF-1α.

Without wishing to be bound by a theory, a CXCR4 inhibitor can act by a number of different pathways. For example, a CXCR4 inhibitor can bind to a ligand bind site on the CXCR4 receptor and interfere with binding of the ligand to the CXCR4 receptor, bind to a nonligand binding site on the CXCR4 receptor and interfere with binding of the ligand to the CXCR4 receptor, bind with a CXCR4 receptor ligand and interfere with binding of the ligand to the CXCR4 receptor, or inhibit the expression of a polynucleotide (e.g., mRNA) expressing CXCR4.

In some embodiments, a CXCR4 inhibitor inhibits the biological activity of the CXCR4 receptor by at least 5%, at least 10%, at least 15%, at least 20%, at least 30%, at least 40%, at least 50%, at least 60%, at least 70%, at least 75%, at least 80%, at least 85%, at least 90%, or at least 95% relative to a control. In some embodiments, a CXCR4 inhibitor completely abrogates the biological activity of the CXCR4 receptor relative to a control. A control can comprise a sample that is not treated an inhibitor.

In some embodiments, a CXCR4 inhibitor is a nucleic acid. Exemplary CXCR4 nucleic acid inhibitors include, but are not limited to, antisense oligonucleotides, siRNAs, shRNAs, microRNAs, aptamers, ribozymes and decoy oligonucleotides. A CXCR4 nucleic acid inhibitor can inhibit the expression of a CXCR4 gene. Accordingly, in some embodiments, a CXCR4 nucleic acid inhibitor comprises a sequence which is complementary to a portion of SEQ ID No: 1. In some embodiments, a CXCR4 nucleic acid inhibitor comprises a sequence which is complementary to a portion of 5' untranslated region of SEQ ID NO: 1 which also includes the start codon. In some embodiments, a CXCR4 nucleic acid inhibitor comprises a sequence which is complementary to a portion of 3' untranslated region of SEQ ID NO: 1. In some embodiments, complementarity is over a stretch of at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of SEQ ID NO: 1. Exemplary anti CXCR4 siRNAs are described, for example, in U.S. Pat. App. Pub. No. 2007/0238868, No. 2009/0253772, content of both of which is incorporated herein by reference. Some exemplary CXCR4 antisense oligonucleotides are described, for example, in U.S. Pat. App. Pub. No. 2004/0209837, content of which is incorporated herein by reference.

In some embodiments, the CXCR4 inhibitor binds to CXCR4 or to CXCL12 (SDF-1$\alpha$). In another embodiment, the CXCR4 inhibitor is an antibody or antibody fragment. In some embodiments, the CXCR4 inhibitor is a small molecule, for example, AMD-3100, ALX40-4C, T22, T140, Met-SDFlbeta, T134, or AMD-3465.

Exemplary CXCR4 inhibitors include, but are not limited to, 2,2'-bicyclam; 6,6'-bicyclam; the embodiments set forth in U.S. Pat. Nos. 5,021,409, and 6,001,826, and in particular 1,1'-[1,4-phenylene-bis(methylene)]-bis-1,4,8,11tetraazacyclotetradecane, set forth in U.S. Pat. No. 5,583,131, and designated herein AMD3100. In some embodiments, a CXCR4 inhibitor can be N'-(1 Hbenzimidazol-2-ylmethyl)-N'-(5,6,7,8-tetrahydroquinoline-8-yl)-butane-1,4-diamine as described in U.S. Patent Publication No. 2003/0220341, CTCF-0214; CTCF-9908; CP-1221 (linear peptides, cyclic peptides, natural amino-acids, unnatural amino acids, and peptidomimetic compounds); 4F-benzoylTN24003; KRH-1120; KRH-1636; KRH-2731; polyphemusin analogue; ALX40-4C; or those described in WO 01/85196; WO 99/50461; WO 01/94420; WO 03/090512, each of which is incorporated by reference herein in its entirety.

CXCR4 inhibitors include the T-140 analogs and antibodies described in US Patent Publication 2010/0055088, the cycle polyamines described in US Patent Publication 2009/0221683, and the compounds disclosed in US Patent Publication Nos. 2004/0209921, 2005/0059702, 2005/0043367, 2005/0277670, 2010/0178271, and 2003/0220341; U.S. Pat. Nos. 5,021,409, 6,001,826, 5583131, and Patent Publication WO 03/011277, each of which are incorporated herein by reference in their entirety.

CXCR4 inhibitors can also include, but are not limited to, polypeptides that specifically bind to CXCR4. Such inhibitors include T140 and derivatives of T140. Exemplary derivatives of T140 include, but are not limited to, TN14003, TC14012, and TE14011 as well as those found in Tamamura, H. et al. Org. Biomol. Chem. 1:3656-3662, 2003, which is incorporated by reference herein in its entirety.

Administration of CXCR4 Inhibitors

Certain aspects of the invention described herein are based, in part, on the discovery by the inventor that administration of a CXCR4 inhibitor is effective in suppressing tumor regrowth, angiogenesis, and/or metastasis if administered within 5 days of administration of another anti-tumor therapy, e.g. radiation therapy or a VEGF inhibitor. Accordingly, provided herein are methods for the treatment and prevention of a cancer in a subject in need thereof. In some aspects of these methods, a therapeutically effective amount of a CXCR4 inhibitor is administered within 5 days of administration of an anti-tumor agent using a systemic, such as an intraperitoneal or intravenous route. In other aspects of these methods, a therapeutically effective amount of a CXCR4 inhibitor is administered within 5 days of administration of an anti-tumor agent using any other method which results in a therapeutically effective amount of the CXCR4 inhibitor localizing at the area being treated, e.g. intrapulmonary administration. These methods are particularly aimed at treatments of human subjects having or at risk for a cancer. In some embodiments, these methods are particularly aimed at treatments of human subjects having or at risk for metastasis of a cancer. In some embodiments of the aspects described herein, a subject having a cancer is first selected prior to administration of the CXCR4 inhibitor.

In some embodiments, a CXCR4 inhibitor is administered within 15 minutes, within 30 minutes, within 1 hour, within 2 hours, within 3 hours, within 4 hours, within 5 hours, within 6 hours, within 12 hours, within 18 hours, within 1 day, within 2 days, within 3 days, within 4 days, or within 5 days of administering of the anti-tumor therapy.

In some embodiments, a CXCR4 inhibitor is administered at least 15 minutes, at least 30 minutes, at least 1 hour, at least 2 hours, at least 3 hours, at least 4 hours, at least 5 hours, at least 6 hours, at least 2 hours, at least 18 hours, at least 1 day, at least 2 days, at least 3 days, or at least 4 days after administering of the anti-tumor therapy.

In some embodiments, a CXCR4 inhibitor is administered concurrently with the anti-tumor therapy.

The dosage can be determined by a physician and adjusted, as necessary, to suit observed effects of the treatment. Generally, the compositions are administered so that a CXCR4 inhibitor is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the CXCR4 inhibitor is administered daily for a period of at least 1 day, at least 2 days, at least 3 days, at least 4 days, at least 5 days, at least 6 days, at least 1 week, at least 2 weeks, at least 3 weeks, at least 1 month, at least 2 months after administering of the anti-tumor therapy.

The CXCR4 inhibitors described herein can be administered to a subject in need thereof by any appropriate route which results in an effective treatment in the subject. As used herein, the terms "administering," and "introducing" are used interchangeably and refer to the placement of a CXCR4 inhibitor into a subject by a method or route which results in at least partial localization of such agents at a desired site, such as a site of a tumor, such that a desired effect(s) is produced.

The terms "subject" and "individual" are used interchangeably herein, and refer to an animal, for example, a human from whom cells for use in the methods described herein can be obtained (i.e., donor subject) and/or to whom treatment, including prophylactic treatment, with the cells as described herein, is provided, i.e., recipient subject. For treatment of those conditions or disease states that are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

In some embodiments, the CXCR4 inhibitor is administered to a subject diagnosed as having or being at risk for develop a cancer or metastasis of a cancer by any mode of administration that delivers the agent systemically or to a desired surface or target, and can include, but is not limited to, injection, infusion, instillation, intrapulmonary (including intranasal and intratracheal), rectal administration, inhalation and oral administration. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the CXCR4 inhibitors for use in the methods described herein are administered by intravenous infusion or injection.

The phrases "parenteral administration" and "administered parenterally" as used herein, refer to modes of administration other than enteral and topical administration, usually by injection, and includes, without limitation, intravenous, intraperitoneal, intramuscular, intraarterial, intrathecal, intraventricular, intracapsular, intraorbital, intracardiac, intradermal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein refer to the administration of the CXCR4 inhibitor other than directly into a target site, tissue, or organ, such as a tumor site, such that it enters the subject's circulatory system and, thus, is subject to metabolism and other like processes.

In some embodiments of the aspects described herein, the methods further comprise administration of one or more additional therapeutic agents, such as a drug or a molecule, that can enhance or potentiate the effects mediated by the administration of the anti-tumor agent and the CXCR4 inhibitor, such as reducing tumor invasion by BDMCs. The therapeutic agent may be a protein (such as an antibody or antigen-binding fragment), a peptide, a polynucleotide, an aptamer, a virus, a small molecule, a chemical compound, a cell, a drug, etc.

For the clinical use of the methods described herein, administration of the CXCR4 inhibitor can include formulation into pharmaceutical compositions or pharmaceutical formulations for parenteral administration, e.g., intravenous; mucosal, e.g., intranasal; ocular, or other mode of administration. In some embodiments, the CXCR4 inhibitor described herein can be administered along with any pharmaceutically acceptable carrier compound, material, or composition which results in an effective treatment in the subject. Thus, a pharmaceutical formulation for use in the methods described herein can contain a CXCR4 inhibitor as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a bispecific or multispecific polypeptide agent. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

In some embodiments of the aspects described herein, the methods further comprise administration of one or more surfactants as therapeutic agents, or may be used in combination with one or more surfactant therapies. Surfactant, as used herein, refers to any surface active agent, including but not limited to wetting agents, surface tension depressants, detergents, dispersing agents, emulsifiers. Particularly preferred are those that from a monomolecular layer over pulmonary alveolar surfaces, including but not limited to lipoproteins, lecithins, and sphygomyelins. Exemplary surfactants include, but are not limited to surfactant protein A, surfactant protein B, surfactant protein C, surfactant protein D, and mixtures and combinations thereof. Commercially available surfactants include, but are not limited to, KL-4, Survanta, bLES, Infasurf, Curosurf, HL-10, Alveofact, Surfaxin, Venticute, Pumactant/ALEC, and Exosurf.

The CXCR4 inhibitor described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a bispecific or multispecific polypeptide agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of CXCR4 inhibitors that can be used in the methods described herein are illustrated below.

Parenteral Dosage Forms.

Parenteral dosage forms of the CXCR4 inhibitor can also be administered to a subject with a chronic immune condition by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol Formulations.

A CXCR4 inhibitor can be packaged in a pressurized aerosol container together with suitable propellants, for example, hydrocarbon propellants like propane, butane, or isobutane with conventional adjuvants. A CXCR4 inhibitor can also be administered in a non-pressurized form such as in a nebulizer or atomizer. A CXCR4 inhibitor can also be administered directly to the airways in the form of a dry powder, for example, by use of an inhaler.

Suitable powder compositions include, by way of illustration, powdered preparations of a bispecific or multispecific polypeptide agent thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S, and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the CXCR4 inhibitor described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms.

In some embodiments of the aspects described herein, a CXCR4 inhibitor can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the CXCR4 inhibitors described herein. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, a CXCR4 inhibitor for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of a CXCR4 inhibitor administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Cancers

In some embodiments of the methods described herein, the subject having a being administered the CXCR4 inhibitor within 5 days of receiving an anti-tumor treatment has a cancer or tumor.

Accordingly, provided herein are methods to treat a subject having a cancer or tumor comprising administering an effective amount of a CXCR4 inhibitor within 5 days of administering an anti-tumor agent to the subject. In some embodiments, the CXCR4 inhibitor is administered at least 2 days after administration of an anti-tumor agent.

In some embodiments of the invention, the subject is first diagnosed as having a cancer prior to administering the cells according to the methods described herein. In some embodiments, the subject is first diagnosed as being at risk of developing cancer or metastasis of a cancer prior to administering the CXCR4 inhibitor.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

In some embodiments, metastasis is not a metastasis of a head or neck cancer cell.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, cancer is not a glioma or glioblastoma.

In some embodiments of the methods described herein, the methods comprise administering to a subject a CXCR4 inhibitor within 5 days of administering an anti-tumor treatment. In some embodiments, the anti-tumor treatment can be a chemotherapeutic agent. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX);

lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In some embodiments, the anti-tumor treatment can be a VEGF inhibitor. VEGF inhibitors are described elsewhere herein. In some embodiments, the anti-tumor treatment can be a p38 MAPK inhibitor. P38 MAPK inhibitors are described elsewhere herein.

In some embodiments, the anti-tumor treatment can be a radiation treatment or radiation therapy. A variety of radiation therapies are used in tumor therapy. Radiation therapy can be administered locally, to the entire body of the subject, or as a combination thereof.

For some types of tumors, radiation may be given to areas that do not have evidence of tumors. This is done to prevent tumor cells from growing in the area receiving the radiation. This technique is called prophylactic radiation therapy. Radiation therapy also can be given to help reduce symptoms such as pain from cancer that has spread to the bones or other parts of the body. This is called palliative radiation therapy.

Radiation may come from a machine outside the body (external radiation), may be placed inside the body (internal radiation), or may use unsealed radioactive materials that go throughout the body (systemic radiation therapy). The type of radiation to be given depends on the type of cancer, its location, how far into the body the radiation will need to go, the patient's general health and medical history, whether the patient will have other types of cancer radiation, and other factors. Most people who receive radiation therapy for cancer have external radiation. Some patients have both external and internal or systemic radiation therapy, either one after the other or at the same time. External radiation therapy usually is given on an outpatient basis; most patients do not need to stay in the hospital. External radiation therapy is used to treat most types of cancer, including cancer of the bladder, brain, breast, cervix, larynx, lung, prostate, and vagina. In addition, external radiation may be used to relieve pain or ease other problems when cancer spreads to other parts of the body from the primary site.

Intraoperative radiation therapy (IORT) is a form of external radiation that is given during surgery. IORT is used to treat localized cancers that cannot be completely removed or that have a high risk of recurring (coming back) in nearby tissues. After all or most of the cancer is removed, one large, high-energy dose of radiation is aimed directly at the tumor site during surgery (nearby healthy tissue is protected with special shields). The patient stays in the hospital to recover from the surgery. IORT may be used in the radiation of thyroid and colorectal cancers, gynecological cancers, cancer of the small intestine, and cancer of the pancreas. It is also being studied in clinical trials (research studies) to treat some types of brain tumors and pelvic sarcomas in adults.

Prophylactic cranial irradiation (PCT) is external radiation given to the brain when the primary cancer (for example, small cell lung cancer) has a high risk of spreading to the brain.

Internal radiation therapy (also called brachytherapy) uses radiation that is placed very close to or inside the tumor. The radiation source is usually sealed in a small holder called an implant. Implants may be in the form of thin wires, plastic tubes called catheters, ribbons, capsules, or seeds. The implant is put directly into the body. Internal radiation therapy may require a hospital stay. Internal radiation is usually delivered in one of two ways, each of which uses sealed implants. Interstitial radiation therapy is inserted into tissue at or near the tumor site. It is used to treat tumors of the head and neck, prostate, cervix, ovary, breast, and perianal and pelvic regions. Some women treated with external radiation for breast cancer receive a "booster dose" of radiation that may use interstitial radiation or external radiation. Intracavitary or intraluminal radiation therapy is inserted into the body with an applicator. It is commonly used in the radiation of uterine cancer. Researchers are also studying these types of internal radiation therapy for other cancers, including breast, bronchial, cervical, gallbladder, oral, rectal, tracheal, uterine, and vaginal. Systemic radiation therapy uses radioactive materials such as iodine 131 and strontium 89. The materials may be taken by mouth or injected into the body. Systemic radiation therapy is sometimes used to treat cancer of the thyroid and adult non-Hodgkin lymphoma.

In some embodiments, the anti-tumor treatment is a systemic radiopharmaceutical agent. By way of non-limiting example, the radiopharmaceutical agent, Alpharadin® (radium-223 chloride), is useful in treating metastatic prostate cancer.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of a CXCR4 inhibitor as described herein to a subject in order to treat a cancer. As used herein, "alleviating a symptom of a cancer" is ameliorating any condition or symptom associated with the cancer. Alternatively, alleviating a symptom of a cancer can involve reducing the size of a tumor relative to the size, or reduction in size, of a tumor in an untreated control. As compared with an equivalent untreated control, such reduction or degree of prevention is at least 5%, 10%, 20%, 40%, 50%, 60%, 80%, 90%, 95%, or 98% as measured by any standard technique. Desirably, the cancer is completely eliminated as detected by any standard method known in the art, in which case the cancer can be considered to have been treated. A patient who is being treated for a cancer is one who a medical practitioner has diagnosed as having such a condition. Diagnosis can be by any suitable means. Diagnosis and monitoring can involve, for example, MRI, mammography, biopsy, blood count tests, x-rays, ultrasounds tests for the levels of markers associated with particular cancers (e.g. CA125 is associated with ovarian cancer and prostate-specific antigen (PSA) is associated with prostate cancer).

The term "effective amount" as used herein refers to the amount of a CXCR4 inhibitor, needed to alleviate at least one or more symptom of the disease or disorder, and relates to a sufficient amount of pharmacological composition to provide the desired effect, i.e., reduce the size a tumor relative to an untreated control. The term "therapeutically effective amount" therefore refers to an amount of a CXCR4 inhibitor using the methods as disclosed herein, that is sufficient to have a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the bispecific or multispecific polypeptide agent), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

For the clinical use of the methods described herein, a CXCR4 inhibitor as described herein can be administered along with any pharmaceutically acceptable compound, material, or composition which results in an effective treatment in the subject. Thus, a pharmaceutical formulation for use in the methods described herein can contain a CXCR4 inhibitor in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media (e.g., stem cell media), encapsulating material, manufacturing aid (e.g., lubricant, talc magnesium, calcium or zinc stearate, or steric acid), or solvent encapsulating material, involved in maintaining the activity of, carrying, or transporting the isolated or enriched populations of hematopoietic stem cells from one organ, or portion of the body, to another organ, or portion of the body.

Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) phosphate buffered solutions; (3) pyrogen-free water; (4) isotonic saline; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) cellulose, and its derivatives, such as sodium carboxymethyl cellulose, methylcellulose, ethyl cellulose, microcrystalline cellulose and cellulose acetate; (17) powdered tragacanth; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; (25) starches, such as corn starch and potato starch; and (26) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

VEGF Inhibitors

VEGF is also referred to as VPF; VEGFA; MVCD1; or MGC70609.

As used herein, the term "VEGF inhibitor" refers to molecules and compositions that interfere with or inhibit the biological activity of VEGF. The VEGF inhibitors can encompass numerous classes of chemical molecules, e.g., small organic or inorganic molecules, polysaccharides, biological macromolecules, e.g., peptides, proteins, peptide analogs and derivatives, peptidomimetics, antibodies, antibody fragments, nucleic acids, nucleic acid analogs and derivatives, an extract made from biological materials such as bacteria, plants, fungi, or animal cells or tissues, naturally occurring or synthetic compositions.

Without wishing to be bound by a theory, a VEGF inhibitor can act by a number of different pathways. For example, a VEGF inhibitor can bind to a ligand binding site on VEGF and interfere with binding of the VEGF to a receptor, bind to a nonligand binding site on VEGF and interfere with binding of the ligand to a receptor, bind with a VEGF receptor and interfere with binding of the ligand to the receptor, or inhibit the expression of a polynucleotide (e.g., mRNA) expressing VEGF.

In some embodiments, a VEGF inhibitor inhibits the biological activity of VEGF by at least 5%, at least 10%, at least 15%, at least 20%, at least 30%, at least 40%, at least 50%, at least 60%, at least 70%, at least 75%, at least 80%, at least 85%, at least 90%, or at least 95% relative to a control. In some embodiments, a VEGF inhibitor completely abrogates the biological activity of VEGF relative to a control. A control can comprise a sample that is not treated an inhibitor.

In some embodiments, a VEGF inhibitor is a nucleic acid. Exemplary VEGF nucleic acid inhibitors include, but are not limited to, antisense oligonucleotides, siRNAs, shRNAs, microRNAs, aptamers, ribozymes and decoy oligonucleotides. A VEGF nucleic acid inhibitor can inhibit the expression of a VEGF gene. Accordingly, in some embodiments, a VEGF nucleic acid inhibitor comprises a sequence which is complementary to a portion of an mRNA encoding VEGF. In some embodiments, a VEGF nucleic acid inhibitor comprises a sequence which is complementary to a portion of 5' untranslated region of an mRNA encoding VEGF which also includes the start codon. In some embodiments, a VEGF nucleic acid inhibitor comprises a sequence which is complementary to a portion of 3' untranslated region of an mRNA encoding VEGF. In some embodiments, complementarity is over a stretch of at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of SEQ ID NO: 1. Exemplary anti VEGF siRNAs are described, for example, in U.S. Pat. App. Pub. No. 2008/0152654, US 2010/151007, US 2010/0168207, and US 2006/0223770, content of which is incorporated herein by reference.

Exemplary VEGF inhibitors include, but are not limited to, Avastin (bevacizumab), an anti-VEGF monoclonal antibody of Genentech, Inc. of South San Francisco, Calif., CP-547, 632 (Pfizer Inc., NY, USA), AG13736 (Pfizer Inc.), ZD-6474 (AstraZeneca), AEE788 (Novartis), AZD-2171), VEGF Trap (Regeneron/Aventis), Vatalanib (also known as PTK-787, ZK-222584: Novartis & Schering AG), Macugen (pegaptanib octasodium, NX-1838, EYE-001, Pfizer Inc./Gilead/Eyetech), 1M862 (Cytran Inc. of Kirkland, Wash., USA); and angiozyme, a synthetic ribozyme from Ribozyme (Boulder, Colo.) and Chiron (Emeryville, Calif.) and combinations thereof. VEGF inhibitors useful in the practice of the present invention are disclosed in U.S. Pat. Nos. 6,534,524 and 6,235,764, both of which are incorporated in their entirety for all purposed. Additional VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 6,534,524 (discloses AG13736), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety.

Examples of VEGF inhibitors include, but are not limited to, and the compounds disclosed in U.S. Pat. Nos. 7,279,159, 5,521,184, U.S. Pat. No. 5,770,599, U.S. Pat. No. 5,990,141, U.S. Pat. No. 6,235,764, U.S. Pat. No. 6,258,812, U.S. Pat. No. 6,515,004, U.S. Pat. No. 6,630,500, U.S. Pat. No. 6,713,485, or US Patent Publication Nos. 2006/0241115, 2009/0304694, 2003/0105091, US2006/0241115, and WO2005/070891, WO 01/32651, WO 02/68406, WO 02/66470, WO 02/55501, WO 04/05279, WO 04/07481, WO 04/07458, WO 04/09784, WO 02/59110, WO 99/450029, WO 00/59509, WO 99/61422, WO 00/12089, WO 00/02871, and WO 01/37820, all of which are incorporated herein in their entirety particularly in parts pertinent to VEGF inhibitors useful in the invention herein described.

VEGF inhibitors can include, but are not limited to, ABT-869 (Abbott) including formulations for oral administration and closely related VEGF inhibitors; AEE-788 (Novartis) (also called AE-788 and NVPAEE-788, among others) including formulations for oral administration and closely related VEGF inhibitors; AG-13736 (Pfizer) (also called AG-013736) including formulations for oral administration and closely related VEGF inhibitors; AG-028262 (Pfizer) and closely related VEGF inhibitors; Angiostatin (EntreMed) (also called CAS Registry Number 86090-08-6, K1-4, and rhuAngiostatin, among others) and closely related inhibitors as described in, among others, U.S. Pat. Nos. 5,792,825 and 6,025,688 which are hereby incorporated by reference in their entireties, particularly in parts pertaining to Angiostatin and closely related VEGF inhibitors, their structures and properties, and methods for making and using them; Avastin™ (Genentech) (also called bevacizumab, R-435, rhuMAB-VEGF, and CAS Registry Number 21697475-3, among others) and closely related VEGF inhibitors; AVE-8062 (Ajinomoto Co. and Sanofi-aventis) (also called AC-7700 and combretastatin A4 analog, among others), and closely related VEGF inhibitors; AZD-2171 (AstraZeneca) and closely related VEGF inhibitors; Nexavar® (Bayer AG and Onyx) (also called CAS Registry Number 284461-73-0, BAY-43-9006, raf kinase inhibitor, sorafenib, sorafenib analogs, and IDDBCP150446, among others) and closely related VEGF inhibitors; BMS-387032 (Sunesis and Bristol-Myers Squibb) (also called SNS-032 and CAS Registry Number 345627-807, among others) and closely related VEGF inhibitors; CEP-7055 (Cephalon and Sanofi-aventis) (also called CEP-11981 and SSR-106462, among others) and closely related VEGF inhibitors; CHIR-258 (Chiron) (also called CAS Registry Number 405169-16-6, GFKI, and GFKI-258, among others) and closely related VEGF inhibitors; CP-547632 (OSI Pharmaceuticals and Pfizer) (also called CAS Registry Number 252003-65-9, among others) and closely related VEGF inhibitors such as, for instance, CP-564959; E-7080 (Eisai Co.) (also called CAS Registry Number 417716-92-8 and ER-203492-00, among others) and closely related VEGF inhibitors; 786034 (GlaxoSmithKline) and closely related VEGF inhibitors; GW-654652 (GlaxoSmithKline) and closely related indazolylpyrimidine Kdr inhibitors; IMC-1C11 (ImClone) (also called DC-101 and c-p 1 CI 1, among others) and closely related VEGF inhibitors; KRN-951 (Kirin Brewery Co.) and other closely related quinoline-urea VEGF inhibitors; PKC-412 (Novartis) (also called CAS Registry Number 120685-11-2, benzoylstaurosporine, CGP-41251, midostaurin, and STI-412, among others) and closely related VEGF inhibitors; PTK-787 (Novartis and Schering) (also called CAS Registry Numbers 212141-54-3 and 212142-18-2, PTK/ZK, PTK-787/ZK-222584, ZK-22584, VEGF-TKI, VEGF-RKI, PTK-787A, DE-00268, CGP-79787, CGP-79787D, vatalanib, ZK-222584, among others) and closely related anilinophthalazine derivative VEGF inhibitors; SU11248 (Sugen and Pfizer) (also called SU-11248, SU-011248, SU-11248J, Sutent®, and sunitinib malate, among others) and closely related VEGF inhibitors; SU-5416 (Sugen and Pfizer/Pharmacia) (also called CAS Registry Number 194413-58-6, semaxanib, 204005-469, among others) and closely related VEGF inhibitors; SU-6668 (Sugen and Taiho) (also called CAS Registry Number 252916-29-3, SU-006668, and TSU-68, among others) and closely related VEGF inhibitors as described in, among others, WO-09948868, WO-09961422, and WO-00038519, which are hereby incorporated by reference in their entireties, particularly in parts pertaining to SU-6668 and closely related VEGF inhibitors, their structures and properties, and methods for making and using them; VEGF Trap (Regeneron and Sanofi-aventis) (also called AVE-0005 and Systemic VEGF Trap, among others) and closely related VEGF inhibitors as described in, among others, WO-2004110490, which is hereby incorporated by reference in its entirety, particularly in parts pertaining to VEGF Trap and closely related VEGF inhibitors, their structures and properties, and methods for making and using them; Thalidomide (Celgene) (also called CAS Registry Number 50-35-1, Synovir, Thalidomide Pharmion, and Thalomid, among others) and closely related VEGF inhibitors; XL-647 (Exelixis) (also called EXEL-7647, among others) and closely related VEGF inhibitors; XL-999 (Exelixis) (also called EXEL-0999, among others) and closely related VEGF inhibitors; XL-880 (Exelixis) (also called EXEL-2880, among others) and closely related VEGF inhibitors; ZD-6474 (AstraZeneca) (also called CAS Registry Number 443913-73-3, Zactima, and AZD-6474, among others) and closely related anilinoquinazoline VEGF inhibitors; and ZK-304709 (Schering) (also called CDK inhibitors (indirubin derivatives), ZK-CDK, MTGI, and multi-target tumor growth inhibitor, among others) and other closely related compounds including the indirubin derivative VEGF inhibitors described in WO-00234717, WO-02074742, WO-02100401, WO-00244148, WO-02096888, WO-03029223, WO-02092079, and WO-02094814 which are hereby incorporated by reference in their entireties particularly in parts pertinent to these and closely related VEGF inhibitors, their structures and properties, and methods for making and using them. Further non-limiting examples of VEGF inhibitors are Pazopanib, CDP791, Enzastaurin, BIBF 1120, BAY 573952, BAY 734506, XL 184, IMC-1121B, CEP 701, SU 014813, SU 10944, SU 12662, OSI-930, and BMS 582664, and closely related VEGF inhibitors. In addition to the foregoing inhibitors that act directly on VEGF or VEGFR, the following inhibitors have anti-angiogenic properties and can be used in the invention in much the same way as inhibitors that act directly: ZD-6126 (AstraZeneca and Angiogene) (also called CAS Registry Number 219923-05-4, N-acetylcolchinol phosphate, ANG-453, AZD-6126, ZD-6126 derivatives and ZM-445526, among others) and closely related VEGF inhibitors such as other inhibitors in the ANG-400 series; Imatinib (Novartis) (also called CAS Registry Numbers 152459-95-5 and 220127-57-1, Glivec, Gleevec, STI-571, and CGP-57148, among others) and closely related VEGF inhibitors; RAD-001 (Novartis) (also called CAS Registry Number 159351-69-6, RAD-001, SDZ-RAD, Certican, and everolimus, among others) and closely related VEGF inhibitors; and BMS-354825 (Bristol-Myers Squibb) (also called CAS Registry Number 302962-49-8, Src/Abl kinase inhibitor, and dasatinib, among others) and closely related VEGF inhibitors. Also useful in the invention in this are regard are Volociximab, CCI-779, 17-AAG, DMXAA, CI-1040, and CI-1033. VEGF inhibitors can also include, but are not limited to, (a) a compound described in US2003/0125339 or U.S. Pat. No. 6,995,162 which is herein incorporated by reference in its entirety, particularly in parts disclosing VEGF inhibitors; (b) a substituted alkylamine derivative described in US2003/0125339 or US2003/0225106 or U.S. Pat. No. 6,995,162 or U.S. Pat. No. 6,878,714 each of which is herein incorporated by reference in its entirety, particularly in parts disclosing VEGF inhibitors; (c) a non-naturally occurring humanized monoclonal antibody that binds to VEGF; (d) a substituted omega-carboxyaryl diphenyl urea or derivative thereof as described in WO00/42012, WO00/41698, US2005/0038080A1, US2003/0125359A1, US2002/0165394A1, US2001/003447A1, US2001/0016659A1, and US2002/013774A1 which are herein incorporated by reference in their entirety, particularly in parts disclosing the foregoing VEGF inhibitors; (e) an anilinophthalazine or derivative thereof that binds to and inhibits the activity of multiple receptor tyrosine kinases including binding to the protein kinase domain and inhibition of VEGFR1 and VEGFR2; (f) (5-[5-fluoro-2-oxo-1,2-dihydroindol(3Z)-ylidenemethyl]-2,4-dimethyl-1H-pyrrole-3-carboxylic acid [2-diethylaminoethyl]amide) or derivatives thereof that are VEGF inhibitors; and (g) VEGF inhibitors as described in US2006/0241115, including those of Formula IV therein. (h) 4TBPPAPC or a closely related compound described in US2003/0125339 or U.S. Pat. No. 6,995,162 which is herein incorporated by reference in its entirety, particularly in parts disclosing 4TBPPAPC and closely related VEGF inhibitors; (i) AMG 706 or a closely related substituted alkylamine derivative described in US2003/0125339 or US2003/0225106 or U.S. Pat. No. 6,995,162 or U.S. Pat. No. 6,878,714 each of which is herein incorporated by reference in its entirety, particularly in parts disclosing AMG 706 and these closely related VEGF inhibitors; (j) Avastin™ or a closely related non-naturally occurring humanized monoclonal antibody that binds to VEGF, is a VEGF inhibitor, and is at least 90% identical in sequence to Avastin™; (k) Nexavar® or a closely related substituted omega-carboxyaryl diphenyl urea or derivative thereof described in WO00/42012, WO00/41698, US2005/0038080A1, US2003/0125359A1, US2002/0165394A1, US2001/003447A1, US2001/0016659A1, and US2002/013774A1 which are herein incorporated by reference in their entirety, particularly in parts disclosing these VEGF inhibitors; (l) PTK/ZK or a closely related anilinophthalazine or derivative thereof that binds to and inhibits the activity of multiple receptor tyrosine kinases including binding to the protein kinase domain and inhibition of VEGFR1 and VEGFR2; (m) Sutent® or a closely related derivative of (5-[5fluoro-2-oxo-1,2-dihydroindol-(3Z)-ylidenemethyl]-2,4-dimethyl-1H-pyrrole-3-carboxylic acid [2-diethylaminoethyl]amide) that is a VEGF inhibitor; and (n) VEGF inhibitors as described in US2006/0241115, including those of Formula IV therein.

P38 MAPK Inhibitors

P38 MAPK is also referred to as MAPK1, ERK; p40; p41; ERK2; ERT1; MAPK2; PRKM1; PRKM2; P42MAPK; and p41mapk.

As used herein, the term "p38 MAPK inhibitor" means any material that interferes or inhibits the activity of p38 MAPK or blocks signaling through the p38 MAP kinase pathway. As used herein, the term "p38 MAPK activity" means the ability of p38 MAPK to phosphorylate, inter alia, amplified in breast cancer 1 (AIB1), activating transcription factor 2 (ATF-2), estrogen receptor a (ERa), estrogen receptor (3 (ER(3), mitogen activated protein kinase activated protein kinase 2 (MAPKAP-K2), MAPKAP-K3, p38-related/activated protein kinase (PRAK), Menkes copper transporting P-type ATPase (MNK), mitogen- and stress-activated protein kinase (MSK), ribosomal S6 kinase B (RSK-B), signal transducer and activator of transcription 1 (STAT1), Max/Myc complex, Ets-like transcription factor-1 (Elk1), C/EBP homologous protein (CHOP), myocyte enhancer factor 2 (MEF2), and fragments thereof as measured by any phosphorylation assay known in the art. Nonlimiting examples of phosphorylation assays include activity assays (e.g. in-gel kinase assays) and immunologic assays (e.g. use of an antibody that specifically binds to the phosphorylated protein in immunohistochemistry, immunofluorescence, Western blotting, and ELISA). Without limitations, a p38 MAPK inhibitors can function by reducing the amount of p38 MAPK, inhibiting or blocking p38 MAPK activation, or inhibiting other molecules in the signaling pathway.

Exemplary p38 MAPK inhibitors include, but are not limited to, antisense p38 MAPK nucleic acids and fragments thereof, antibodies that bind p38 MAPK and fragments thereof, EO-1428, SB239063 (Legos et al, 2001, Brain Res. 892:70-77; Barone et al, 2001, Med Res Rev. 21(2): 129145), SB281832, VX-702, VX-745, ZM336372, RPR 200765A (Mclay L M et al, 2001, Bioorg Med. Chem. 9(2):537-554), N-(3-tert-butyl-1-methyl-5-pyrazolyl)N'-(4-(4-pyridinylmethyl)phenyl)urea (Dumas J, 2002, Bioorg Med Chem Lett 12(12):1559-62), SB203580 (Ishizuka et al., *J. Immunol.* 167 (4): 2298-304 (2001) and which can be obtained from Calbiochem), SB202190 (Karahashi et al., *Biochim. Biophys. Acta* 1502(2): 207-23 (2000)), PD169316 (Paine et al, *J. Biol. Chem.* 275(15): 11284-290 (2000)), fr-167653 (Matsuoka et al. *Am. J. Physiol. Lung Cell Mol. Phsiol.* 283: L103-12 (2002)), trans-1-(4-hydroxycyclohexyl)-4-(4-fluorophenyl)-5-(2-methoxypyridimidin-4-yl)imidazole (Underwood et al. *Am. J. Physiol. Lung Cell Mol. Physiol.* 279(5): L895-902 (2000)), 2-(4-Chlorophenyl)-4-)4-fluorophenyl)-5-pyridin-4-yl-1,2-dihydropyrazol-3-one (Calbiochem) and those inhibitors disclosed in U.S. Pat. Nos. 5,670,527; 5,658,903; 5,656,644; 5,559,137; 5,593,992; and 5,593,991; US Patent Publication Nos: 2009/0149443, 2009/0203711 and Patent Publications WO 04/078116, WO 98/27098 and WO 99/00357; all of which are herein incorporated by reference in their entirety.

As used herein, the term "p38 MAPK expression" means the formation of a p38 MAPK gene product as measured by any method known in the art including nucleic acid hybridization method, e.g. Northern blotting, in situ hybridization; nuclear run-on assays; polymerase chain reaction amplification; reporter gene expression, i.e. where the reporter gene is operatively linked to p38 MAPK expression control sequences; gene expression arrays. Formation of a p38 MAPK gene product may also be measured by any antibody-based technique including immunohistochemistry, immunofluorescence, Western blotting, and ELISA.

In some embodiments, a p38 MAPK inhibitor inhibits the biological activity of p38 MAPK by at least 5%, at least 10%, at least 15%, at least 20%, at least 30%, at least 40%, at least 50%, at least 60%, at least 70%, at least 75%, at least 80%, at least 85%, at least 90%, or at least 95% relative to a control. In some embodiments, a p38 MAPK inhibitor completely abrogates the biological activity of p38 MAPK relative to a control. A control can comprise a sample that is not treated an inhibitor.

In some embodiments, a p38 MAPK inhibitor is a nucleic acid. Exemplary p38 MAPK nucleic acid inhibitors include, but are not limited to, antisense oligonucleotides, siRNAs, shRNAs, microRNAs, aptamers, ribozymes and decoy oligonucleotides. A p38 MAPK nucleic acid inhibitor can inhibit the expression of a p38 MAPK gene. Accordingly, in some embodiments, a p38 MAPK nucleic acid inhibitor comprises a sequence which is complementary to a portion of an mRNA encoding p38 MAPK. In some embodiments, a p38 MAPK nucleic acid inhibitor comprises a sequence which is complementary to a portion of 5' untranslated region of an mRNA encoding p38 MAPK which also includes the start codon. In some embodiments, a p38 MAPK nucleic acid inhibitor comprises a sequence which is complementary to a portion of 3' untranslated region of an mRNA encoding p38 MAPK. In some embodiments, complementarity is over a stretch of at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of SEQ ID NO: 1. Exemplary anti p38 MAPK siRNAs are described, for example, in U.S. Pat. Nos. 6,448,079, 6,140,124, and US Patent Publication No. 2005/0043212, content of which is incorporated herein by reference.

Measuring the Level of CXCL12 Expression

Without wishing to be bound by a theory, anti-tumor therapy can increase levels of CXCL12 expression in a subject. For example, CXCL12 expression can increase by at least 5%, at least 10%, at least 20%, at least 30%, at least 40%, at least 50%, at least 60%, at least 70%, at least 80%, at least 90%, at least 1-fold, at least 1.5-folds, at least 2-folds or more relative a reference level. A reference level can be the level of CXCL12 expression in the subject before onset of anti-tumor therapy or the level of CXCL12 expression in a healthy subject.

In some embodiments, the method further comprises measuring the level of CXCL12 expression in the subject after administering of the anti-tumor therapy and comparing the level of CXCL12 expression to a reference level. As discussed above, a reference level can be the level of CXCL12 expression in the subject before onset of anti-tumor therapy or the level of CXCL12 expression in a healthy subject. Generally, measurement of the CXCL12expression level is performed before administering of the CXCL12 inhibitor.

In some embodiments, the CXCL12 expression level is measured within 15 minutes, within 30 minutes, within 1 hour, within 2 hours, within 3 hours, within 4 hours, within 5 hours, within 6 hours, within 12 hours, within 18 hours, within 1 day, within 2 days, within 3 days, within 4 days, or within 5 days of administering of the anti-tumor therapy.

In some embodiments, the CXCL12 expression level is measured every day for at least 1 day, at least 2 days, at least 3 days, at least 4 days or at least 5 days after administering of the anti-tumor therapy.

Generally, CXCR4 inhibitor administration can begin after the level of CXCL12 expression has increased following administration of the anti-tumor therapy. Accordingly, in some embodiments, a CXCR4 inhibitor is not administered until the level of CXCL12 expression in the subject is elevated by at least 5%, at least 10%, at least 15%, at least 20%, at least 25%, at least 30%, at least 40%, at least 50%, at least 60%, at least 70%, at least 80%, at least 90%, at least 1-fold, at last 1.5-fold, at least 2-fold or more relative to a reference level. As discussed above, the reference level can be the level of CXCL12 expression in the subject before onset of anti-tumor therapy or the level of CXCL12 expression in a healthy subject.

In some embodiments, the CXCR4 inhibitor is administered until the level of CXCL12 expression in the subject is within 1%, 2%, 3%, 4%, 5%, 6%, 7%, 8%, 9%, 10%, 15%, or 20% of a reference level. As discussed above, the reference level can be the level of CXCL12 expression in the subject before onset of anti-tumor therapy or the level of CXCL12 expression in a healthy subject.

As the term is used herein, "an elevated level", refers to an identified, reproducible, quantitative or qualitative increase in the physical presence of a target molecule or molecules (e.g., CXCL12 mRNA or protein) relative to a reference level. An elevated level is determined by measuring (e.g., quantitative) the target molecule(s) in a target cell or tissue, to produce a determined amount, followed by comparison to a determined control amount obtained by measuring of the target molecule(s) in an appropriate control cell or tissue. Measurement in the target cell or tissue and in the control cell or tissue is performed by as close to identical methods as possible under the given conditions.

Measurement of the physical presence of a molecule typically involves transformation of the target molecule(s), or another indicator, present in the cell, to an indicator molecule, as described herein. The presence of the indicator molecule is then measured or otherwise quantitatively detected (e.g., by a non-human machine).

It will be appreciated that the methods described herein that involve comparison of a determined level or amount to a reference or control amount, that standard methods available to the skilled practitioner can be used to obtain the appropriate reference amounts. In one embodiment, the reference amount is obtained from a reference or control sample obtained from the subject (e.g. a biological sample). The amount is determined by methods identical or analogous to those used to determine the amount of CXCL12 in the test sample. In some embodiments, normal, healthy tissue, (e.g., located adjacent to the sample tissue), is used as the reference or control tissue. In some embodiments, a sample taken from the subject prior to administration of an anti-tumor may be a reference sample. Preferably the control tissue, or biological sample, is of the same type as the tested sample tissue.

In some embodiments, the reference can be a level of CXCL12 in a subject who has not received a anti-tumor treatment. In some embodiments, the reference can be a level of CXCL12 in a normal, healthy subject who has not received a anti-tumor treatment. For example, a normal healthy subject has normal tissue morphology, and/or is not diagnosed with cancer, and/or has been identified as having a genetic predisposition for developing a cancer (e.g. a family history of cancer or a genetic test for genotypes associated with an increased risk of a cancer) and/or has been exposed to risk factors for cancers (e.g. smoke, cigarette smoke, alcohol, tobacco, obesity, etc). In some embodiments, the reference can be a level of CXCL12 in a subject diagnosed with or at risk of having a cancer who has not received a anti-tumor treatment. Preferably the reference is of the same tissue type as the tested sample. In some embodiments, the reference can also be a level of CXCL12 in a control sample, a pooled sample of control individuals or a numeric value or range of values based on the same.

Biological Samples

Provided herein are methods comprising measuring the level of CXCL12 in a subject. Such a measurement can be made, for example, on a representative tissue sample or other form of biological sample, obtained from the subject. In one embodiment, the cell or tissue is obtained from the subject in the form of a biological sample. The appropriate measurement of CXCL12 is then performed on the biological sample. When necessary, the biological sample can be further processed. For example, a bodily fluid obtained from the subject can be further processed to purify or further concentrate cells or tissues therein.

The term "biological sample" as used herein denotes a sample taken or isolated from a biological organism, e.g., biopsy sample, tissue cell culture supernatant, cell lysate, lymph, lymph node tissue, a homogenate of a tissue sample from a subject or a fluid sample from a subject. Exemplary biological samples include, but are not limited to, tissue biopsies, the external sections of the, cells, etc. In some embodiments, the sample is normal tissue. In some embodiments, the sample is taken from a tumor.

In one embodiment, the tissue is an tumor. In some embodiments the tumor is a primary tumor. In some embodiments the tumor is a secondary tumor. Circulating tumor cells can be further isolated from a biological sample (e.g., bodily fluid) such as blood, lymph, biological fluids, or lymph nodes.

The term "biological sample" also includes untreated or pretreated (or pre-processed) biological samples. In some embodiments, the biological sample is an untreated biological sample. As used herein, the phrase "untreated biological sample" refers to a biological sample that has not had any prior sample pre-treatment except for dilution and/or suspension in a solution. Exemplary methods for treating a biological sample include, but are not limited to, centrifugation, filtration, sonication, homogenization, heating, freezing and thawing, and any combinations thereof. The skilled practitioner is aware of methods and processes appropriate for processing of biological samples required for determination of levels of proteins as described herein.

A biological sample can contain cells from subject. In one embodiment, the biological sample contains non-cellular biological material, such as non-cellular fractions that can be used to measure the level of CXCL12. In some embodiments, the sample is from a resection, biopsy, or core needle biopsy. In addition, fine needle aspirate samples can be used. Samples can be either paraffin-embedded or frozen tissue.

The sample can be obtained by removing a sample of cells from a subject, but can also be accomplished by using previously isolated cells (e.g. isolated at a prior timepoint and isolated by the same or another person). In addition, the biological sample can be freshly collected or a previously collected sample. In some embodiments, a biological sample is a biological fluid. Examples of biological fluids include, but are not limited to, saliva, blood, sputum, an aspirate, and any combinations thereof.

In some embodiments, the biological sample is a frozen biological sample, e.g., a frozen tissue or fluid sample such as sputum. The frozen sample can be thawed before employing methods, assays and systems of the invention. After thawing, a frozen sample can be centrifuged before being subjected to methods, assays and systems of the invention. In some embodiments, the biological sample can be treated with at least one chemical reagent, such as a protease inhibitor. In some embodiments, the biological sample is a clarified biological sample, for example, by centrifugation and collection of a supernatant comprising the clarified biological sample. In some embodiments, a biological sample is a pre-processed biological sample, for example, supernatant or filtrate resulting from a treatment selected from the group consisting of centrifugation, filtration, sonication, homogenization, lysis, thawing, amplification, purification, restriction enzyme digestion ligation and any combinations thereof.

In some embodiments, the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample.

Methods of Measuring the Level of CXCL12 Expression

Methods to measure CXCL12 are well known to a skilled artisan. In one embodiment, methods of measurement involve use of a binding protein (e.g. an antibody) for specific detection (e.g., immunodetection) of CXCL12. Such methods to measure protein level include ELISA (enzyme linked immunosorbent assay), western blot, proteomic microarray, immunoprecipitation, immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques.

Antibodies specific for CXCL12 are available in the art. Antibodies specific for CXCL12 are available, for example, from Abcam; Cambridge, Mass. (Cat. No. ab10395). Alternatively, since the amino acid sequences for CXCL12 are known and publically available at the NCBI website (NCBI Gene ID No: 6387, SEQ ID NOs: 7-10), one of skill in the art can raise their own antibodies against these proteins of interest for the purpose of the invention.

The techniques of immunohistochemistry ("IHC") and immunocytochemistry ("ICC") are particularly suitable for use in the methods described herein. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change (e.g., color or light emission), upon encountering the targeted molecules. In some instances, signal amplification can be integrated into the particular protocol, wherein a secondary antibody, that includes the marker stain or marker signal, follows the application of a primary specific antibody.

The technique of proteomic microarray analysis can be used in the methods described herein. Proteomic microarrays are based on miniature arrays of ligands. Proteins in a sample bind to the ligands on the array and are detected and the amount quantified, often using by fluorescent tags (Templin et al. Proteomics 2003 3:2155-2166; MacBeath, Nature Genetics 2002 32:526-532).

In addition, protein levels may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference. Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, E X S 88:133-44 (2000). In certain embodiments, a gas phase ion spectrophotometer is used.

In other embodiments, laser-desorption/ionization mass spectrometry is used to analyze the level of a protein. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait). In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Detection of the presence of AID mRNA or protein will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

In certain embodiments, measuring the level of CXCL12 expression comprises measuring the level of CXCL12 mRNA. Measuring mRNA levels can, for example, involve the use of one or more of the following assays; RT-PCR, quantitative RT-PCR, Ref-Seq, Northern blot, microarray based expression analysis, transcription amplification and/or self-sustained sequence replication. The mRNA sequences of the several CXCL12 isoforms are known (NCBI Gene ID No: 6387; SEQ ID NOs: 3-6) and their use in the methods described herein will be familiar to those skilled in the art Methods for assessing levels of mRNA are well known to those skilled in the art. Preferred embodiments are herein described. Laser Capture Microdissection Laser Capture Microdissection (LCM) is known to those of skill in the art, see, for example, Simon et al. (1998) Trends in Genetics 14:272 and Emmert-Buck et al. (1996) Science 274:998-1001. In one embodiment of the present invention a tumor sample or biopsy is obtained and LCM is used to obtain genetic material, such as, mRNA, for analysis. Nucleic acid molecules can be isolated from a particular biological sample using any of a number of procedures, which are well known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g. a tumor and normal tissue, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.).

To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes. Methods of real-time quantitative PCR using TaqMan probes are well known in the art. Detailed protocols for real-time quantitative PCR are provided, for example, for RNA in: Gibson et al., 1996 Genome Res., 10:995-1001; and for DNA in: Heid et al., 1996 Genome Res., 10:986-994.

A TaqMan-based assay also can be used to quantify MET polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification.

In another embodiment, for example, detection of RNA transcripts may be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). One suitable method for detecting AID mRNA transcripts is described in reference Pabic et. al. Hepatology, 37(5): 1056-1066, 2003, which is herein incorporated by reference in its entirety. Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In another embodiment, CXCL12 nucleotides can be detected using "self-sustained sequence replication." This is a method of nucleic acid amplification using target nucleic acid sequences which are amplified (replicated) exponentially in vitro under isothermal conditions by using three enzymatic activities essential to retroviral replication: (1) reverse transcriptase, (2) RNase H, and (3) a DNA-dependent RNA polymerase (Guatelli, et al., *Proc. Nat. I. Acad. Sci. USA* 87:1874 (1990)). By mimicking the retroviral strategy of RNA replication by means of cDNA intermediates, this reaction accumulates cDNA and RNA copies of the original target. Substantially isothermal means that the temperature may be varied over the course of an approximately one hour reaction time within the temperature range of about 37° C. to 50° C. Alternatively, one temperature may be selected to carry out the entire reaction. Self-sustained sequence replication at 45° C. is preferred.

In another embodiment, ADF-1a nucleotides can be detected using "transcription amplification." In this method of nucleic acid amplification, each cycle is composed of two steps. In the first step, a cDNA copy of a RNA or DNA target is made and in the second step, multiple RNA transcripts of each cDNA copy are generated (see, e.g., Kwoh (1989) Proc. Natl. Acad. Sci. USA 86: 1173).

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Oligonucleotides corresponding to CXCL12 are immobilized on a chip which is then hybridized with labeled nucleic acids of a test sample obtained from a patient. Positive hybridization signal is obtained with the sample containing CXCL12 transcripts. Methods of preparing DNA arrays and their use are well known in the art. (See, for example U.S. Pat. Nos. 66,186,796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858). To monitor mRNA levels, for example, mRNA is extracted from the biological sample to be tested, reverse transcribed, and fluorescent-labeled cDNA probes are generated. The microarrays capable of hybridizing to CXCL12 cDNA are then probed with the labeled cDNA probes, the slides scanned and fluorescence intensity measured. This intensity correlates with the hybridization intensity and expression levels. Quantitative PCR methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y.

DEFINITIONS

For convenience, certain terms employed herein, in the specification, examples and appended claims are collected here. Unless otherwise defined, all technical and scientific terms used herein have the same meaning as commonly understood by one of ordinary skill in the art to which this invention belongs.

As used herein, in vivo (Latin for "within the living") refers to those methods using a whole, living organism, such as a human subject. As used herein, "ex vivo" (Latin: out of the living) refers to those methods that are performed outside the body of a subject, and refers to those procedures in which an organ, cells, or tissue are taken from a living subject for a procedure, e.g., isolating hematopoietic stem cells from umbilical cord blood obtained from a donor subject, and then administering the isolated hematopoietic stem cell sample to a recipient subject. As used herein, "in vitro" refers to those methods performed outside of a subject, such as an in vitro cell culture experiment. For example, isolated hematopoietic stem cells can be cultured in vitro to expand or increase the number of hematopoietic stem cells, or to direct differentiation of the hematopoietic stem cells to a specific lineage or cell type, e.g., respiratory epithelial cells, prior to being used or administered according to the methods described herein.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ ed., 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The term "agent" refers to any entity which is normally not present or not present at the levels being administered to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "antibody" refers to immunoglobulin molecules and immunologically active portions of immunoglobulin molecules, i.e., molecules that contain an antigen binding site that immunospecifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

The term "anti-tumor therapy" refers to a therapy useful in treating cancer. Examples of anti-tumor therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin®), anti-CD20 antibodies, an epidermal growth factor receptor (EGFR)

antagonist (e.g., a tyrosine kinase inhibitor), HER1/EGFR inhibitor (e.g., erlotinib (Tarceva®)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

In some embodiments, anti-tumor therapy is antiangiogenic therapy. As used herein, the term "antiangiogenic therapy" refers to therapy directed against angiogenesis (i.e., the formation of new capillary blood vessels leading to neovascularization), and/or existing vasculature and relating to a disease condition (e.g., vascular targeting therapy).

In some embodiments, anti-tumor therapy comprises administering a VEGF inhibitor to the subject. In some embodiments, anti-tumor therapy comprises administering a p38 mitogen-activating protein kinase (MAPK) inhibitor to the subject.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "peptide" is used in its broadest sense to refer to compounds containing amino acids, amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. The peptides can be linear or cyclic. A peptide can be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid. As used herein, the term "proteogenic" indicates that the amino acid can be incorporated into a protein in a cell through well-known metabolic pathways.

As used herein, the term "peptidemimetic" refers to a molecule which is capable of folding into a defined three-dimensional structure similar to a natural peptide.

Peptides and peptidomimetics include those having naturally occurring or modified peptides, e.g., D or L peptides; $\alpha$, $\beta$, or $\gamma$ peptides; N-methyl peptides; azapeptides; peptides having one or more amide, i.e., peptide, linkages replaced with one or more urea, thiourea, carbamate, or sulfonyl urea linkages; or cyclic peptides. The peptide or peptidomimetic can be about 5-50 amino acids long, e.g., about 5, 10, 15, 20, 25, 30, 35, 40, 45, or 50 amino acids long.

As used herein, the term "nucleic acid" or "oligonucleotide" or grammatical equivalents herein means at least two nucleotides, including analogs or derivatives thereof, that are covalently linked together. The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphosphoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); Nielsen, Nature, 365: 566 (1993)). The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl.

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., *Science* (2005) vol. 309, pp 1577-1581. Without wishing to be bound by theory, administration of a microRNA, microRNA mimic, and/or anti microRNA oligonucleotide, leads to modulation of pathogen viability, growth, development, and/or replication. In some embodiments, the oligonucleotide is a microRNA, microRNA mimic, and/or anti microRNA, wherein microRNA is a host microRNA.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "*The microRNA Registry*" Griffiths-Jones S, NAR, 2004, 32, Database Issue, D109-D111; and also on the worldwide web at microrna.dot.sanger.dot.ac.dot.uk/sequences/.

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int.

Pat. Appl. Publ. No. WO 94/02595, each specifically incorporated herein by reference, and synthesized to be tested in vitro and in vivo, as described therein.

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000). Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

As used herein, the term "oligosaccharide" refers without limitation to several (e.g., two to ten) covalently linked monosaccharide units. Oligosaccharides include, but are not limited to, disaccharides (i.e., two monosaccharide units) such as sucrose, lactose, maltose, isomaltose, cellobiose and the like.

As used herein, the term "polysaccharide" refers without limitation to many (e.g., eleven or more) covalently linked monosaccharide units. Polysaccharides can have molecular masses ranging well into millions of daltons. The polysaccharide can be homopolysaccharides or heteropolysaccharides. Whereas the homopolysaccharides contain only one kind of unit, the heteropolysaccharides consist of monomer units of different kinds. Exemplary polysaccharides include, but are not limited to, cellulose, chitin, starch, glycogen, glycosaminoglycans (e.g., hyaluronic acid, chondroitin-4-sulfate, chondroitin-6-sulfate, dermatan sulfate, keratin sulfate, heparin and the like) and the like. The di-, tri-, oligo- and poly-saccharides can comprise 1→4, 1→6 or a mixture of 1→4 and 1→6 linkages.

As used herein, the term "therapeutic window" encompasses an aspect of time; the earliest and latest times in which administration of a treatment results in desired pharmacologic effect. Additionally, therapeutic window can encompass the dosage of a composition administered to a subject, e.g. that amount of drug or biologic that provides efficacy or a desired pharmacologic effect over time for the disease or condition without unacceptable toxicity; the range of the circulating blood concentrations between the minimal amount to achieve any positive therapeutic effect and the maximum amount which results in a response that is the response immediately before toxicity to the subject (at a higher dose or concentration).

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., COPYRGT. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene, and polypeptides obtained by translation of mRNA transcribed from a gene. In some embodiments, an expression product is transcribed from a sequence that does not encode a polypeptide, such as a microRNA.

The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons)

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-β-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" typically means a decrease by at least about 5%-10% as compared to a reference level, for example a decrease by at least about 20%, or at least about 30%, or at least about 40%, or at least about 50%, or at least about 60%, or at least about 70%, or at least about 80%, or at least about 90% decrease (i.e. absent level as compared to a reference sample), or any decrease between 10-90% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% increase or more or any increase between 10-90% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Example 1

Recruitment of Myeloid but not Endothelial Precursor Cells Facilitates Tumor Regrowth after Local Irradiation Materials and Methods Animals and Tumors.

54A human lung tumors were xenografted in male athymic NCr/Sed nude (nu/nu) mice, and MCa8 mouse mammary carcinomas were implanted in female syngeneic FVB mice (both subcutaneously in the hind limb; refs. 3, 11). To detect specific BMDC populations in tumors (i.e., $Tie2^{+}CD11b^{-}$ EPCs and $Tie2^{+}CD11b^{+}$ TEMs), irradiated wild-type FVB mice were irradiated with 9 Gy of whole-body irradiation (WBI) followed by restorative bone marrow transplantation (BMT) from Tie2-GFP-FVB donors to create chimeric wild-type/Tie2-GFP-BMT mice (3). MCa8 tumors were implanted in these mice 6 weeks post-BMT.

Treatments and Response Evaluation.

Tumor size was measured with a caliper at least thrice a week. When a tumor reached 5.5 mm in mean diameter, the mouse was randomized to a treatment group. Tumors were γ-irradiated using the same dose delivered either locally alone or locally plus a sublethal WBI dose of 6 Gy. Tumors were locally γ-irradiated (137 Cs, dose rate ~4.5 Gy/min) at doses ranging from 6 to 46 Gy by placing the tumor-bearing leg in a 3-cm diameter radiation field. Sublethal 137 Cs γ-WBI at a dose of 6 Gy was delivered at a dose rate of ~0.6 Gy/min. Anti-tumor effects of 6 Gy and 21 Gy given to tumors either entirely by LI, or by 6 Gy of WBI alone, or by 15 Gy of LI plus 6 Gy of WBI were compared. Unsorted BMDCs (from femurs and tibias of one tumor- and treatment-naïve donor to two recipients) or fluorescence-activated cell-sorted $Sca1^{-}CD11b^{+}$ (150,000-200,000 cells) or $Sca1^{+}CD11b^{+}$ (25,000-50,000) BMDCs (from one donor to one recipient) were i.v. infused in mice receiving LI plus WBI. CXCR4 inhibition was achieved using AMD3100 delivered by ALZET micro-osmotic pumps (Model 1002; DURECT Corporation) implanted s.c. in tumor-bearing mice either alone, or immediately or 5 days after 20 Gy of LI. Therapeutic efficacy was measured as the time taken for tumors to grow to 7.5 mm in diameter (i.e., 2.5-fold increase compared with the pretreatment volume).

Immunohistochemistry and Image Analysis.

Tumors were excised, cut in half, fixed for 2 hours in 4% formaldehyde in PBS, incubated in 30% sucrose in PBS overnight at 4° C. and frozen in optimal cutting temperature compound (Tissue-Tek). Transverse tumors sections, 10 μm thick, were immunostained with hamster anti-mouse CD31 antibody (Chemicon/Millipore, Billerica, Mass.) and secondary Cy5-conjugated anti-hamster antibody (Molecular Probes/Invitrogen, Carlsbad, Calif.) to detect blood vessels; PEconjugated anti-mouse CD11b antibody (BD-Pharmingen, San Diego, Calif.) to detect myeloid BMDCs; and rabbit anti-mouse SDF-1α antibody (Cell Sciences, Canton, Mass.) and secondary Cy3-conjugated anti-rabbit antibody (Molecular Probes). Of note, the latter primary antibody cross-reacted with human CXCL12 (SDF-1α), as demonstrated by similar staining of sequential 54A tumor sections using this antibody and a polyclonal antihuman/mouse SDF-1α antibody (BioVision, Inc.) side by side in pilot studies. Samples were counterstained by mounting with DAPI-containing medium (Vectashield, Vector Labs). Images were captured with a stack step of 5 μm using an Olympus confocal microscope. For each tumor, 8 randomly selected fields by confocal microscopy were analyzed and the analysis was restricted to DAPI-positive (viable tissue) areas. The immunostained area was quantified as fraction of DAPI positive area using in-house segmentation algorithms coded on a MATLAB platform (MathWorks). Maximum z-projection was used for all analyses. A median filter was applied to the DAPI, CD31 and CD11b signals to minimize noise. Cells (for CD11b) and vessels (for CD31) were segmented using user-defined thresholds combined with a morphological size-based filtering. Areas with apparent artifacts were manually excluded. Images were randomly shuffled before the analysis and threshold selection was performed in a blinded manner. For SDF1α expression analysis, all the images were analyzed using the same threshold.

Flow Cytometric Analysis.

Flow cytometry was performed on single-cell suspensions prepared from whole tumors after digestion with collagenase type II (Worthington Biochemical Corporation) and immunostaining for CD11b, Gr1, and F4/80 (using fluorescence-labeled monoclonal antibodies from BD PharMingen) as described (3), using an LSR-II flow cytometer (BD Biosciences).

Statistical Analysis.

Differences between mean values in each group were evaluated by t test for independent samples and considered significant when $P<0.05$. Data are presented as mean±SEM. The comparison between collections of groups was carried out using t tests for linear contrasts in one-way ANOVA. Tumor control probabilities were compared using $\chi^2$ test.

Introduction

Tumor neovascularization and growth might be promoted by the recruitment of bone marrow-derived cells (BMDC), which include endothelial precursor cells and "vascular modulatory" myelomonocytic (CD11b+) cells. BMDCs may also drive tumor regrowth after certain chemotherapeutic and vascular disruption treatments. Presented herein are data demonstrating the role of BMDC recruitment in breast and lung carcinoma xenograft models after local irradiation (LI). Bone marrow was depleted by including whole-body irradiation (WBI) of 6 Gy as part of a total tumor dose of 21 Gy, and compared the growth delay with the one achieved after LI of 21 Gy. In both models, the inclusion of WBI induced longer tumor growth delays. Moreover, WBI increased lung tumor control probability by LI. Exogenous delivery of BMDCs from radiation-naïve donors partially abrogated the WBI effect. Myeloid BMDCs, primarily macrophages, rapidly accumulated in tumors after LI. Intratumoral expression of CXCL12 (stromal-derived factor 1α-SDF-1α), a chemokine that promotes tissue retention of BMDCs, was noted 2 days after LI. Conversely, treatment with an inhibitor of SDF-1α receptor CXCR4 (AMD3100) with LI significantly delayed tumor regrowth. However, when administered starting from 5 days post-LI, AMD3100 treatment was ineffective. Lastly, with restorative bone marrow transplantation of Tie2-GFP-labeled BMDC population, the results presented herein demonstrate an increased number of monocytes but not endothelial precursor cells in tumors that recurred following LI. Our results suggest that an increase in intratumoral SDF-1α triggered by LI recruits myelomonocytes/macrophages which promotes tumor regrowth.

The recruitment of various blood-borne bone marrow-derived cells (BMDC) might be important for tumor neovascularization and growth, but their roles are often difficult to differentiate (1, 2). Endothelial precursor cells (EPC) may directly incorporate in 0% to 50% of newly formed tumor vessels, depending on the tumor type, organ site, and mouse strain (3). In addition, other BMDCs, referred to as "vascular modulatory/accessory" cells, might support angiogenesis in a paracrine manner. Among them, arguably the most important for angiogenesis are cells of myeloid/monocyte lineage ($CD11b^+$), in particular, macrophages and Tie2-expressing monocytes (TEM; refs. 4, 5). The trafficking and tissue retention of BMDCs might depend, at least in part, on CXCL12/CXCR4 receptor pathway activation (6, 7).

EPCs might be increasingly attracted to tumor sites as a result of certain therapies and influence their outcome (e.g., vascular-disruptive and certain chemotherapeutic treatments; refs. 8, 9). But it remains unknown if EPCs contribute significantly after local irradiation (LI) of tumors, the neovascularization of which is presumed to be deficient (10,11). Infiltration by other BMDCs—e.g., myelomonocytes/macrophages—has been previously documented in irradiated tumors (12-16). However, their role as modulators of tumor radiation response remains largely uncharacterized. Herein, the role of various BMDCs in tumor regrowth after LI in lung and breast tumor models is evaluated.

Results

WBI Delays Tumor Regrowth after Irradiation.

To diminish the potential involvement in tumors of host-derived cells following LI, tumor-bearing mice were treated with a sublethal dose of 6 Gy WBI. This dose is known to damage the bone marrow and deplete leukocytes temporarily (for 1.5-2 weeks) from the blood circulation (17, 18). Using this approach, the efficacy of the same radiation dose (21 Gy) given to tumors either as two LI fractions or LI plus WBI was compared; a flow chart of these treatments is presented in FIG. 9A note the identical duration of irradiation. The growth of 54A tumors in nude mice was arrested in both groups, but tumor regrowth was significantly delayed when radiotherapy included WBI. In the case of MCa8 carcinomas grown in immunocompetent FVB mice, tumors shrank by 1.5 to 2 mm posttreatment in both groups and WBI significantly delayed their regrowth. In both tumors, the growth inhibition by 6 Gy of WBI alone was also longer than that by 6 Gy of LI. As summarized in FIGS. 9B-9C, WBI provided additional tumor growth delay in both models despite the difference in tumor postradiation dynamics and distinct immune profiles of the hosts. Finally, WBI significantly enhanced tumor curability following LI with higher doses compared with LI alone in 54A xenografts FIG. 9D. Of note, WBI did not change the weight, appearance, or behavior of mice (data not shown).

BMDC Infusion Promotes Tumor Regrowth after LI Plus WBI.

Figure 9B:
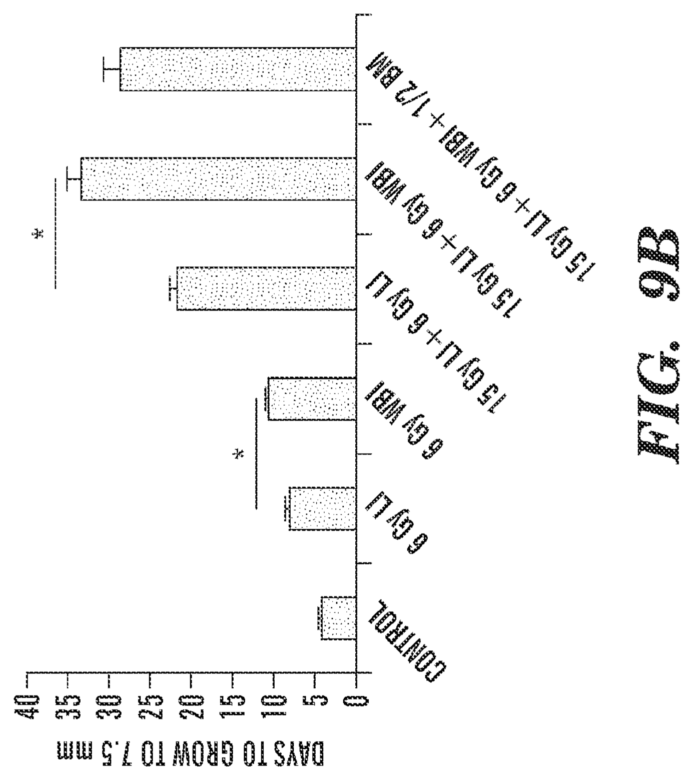
FIGS. 9A-9D demonstrate the antitumor effect of local irradiation (LI) with or without whole body irradiation (WBI).
Figure 9A:
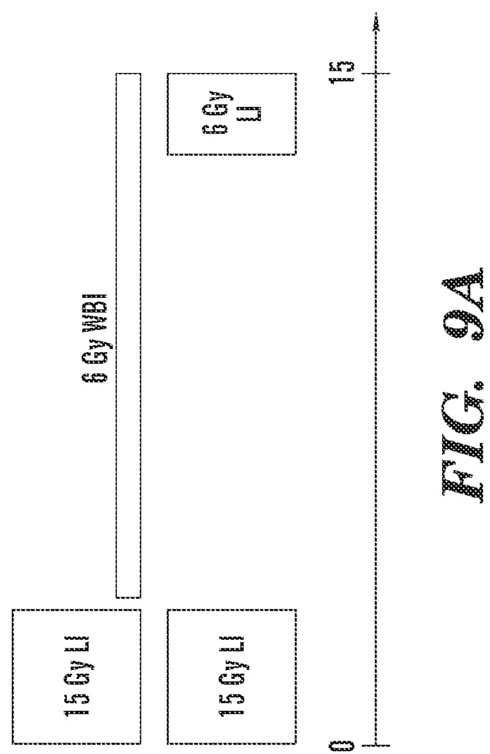
Figure 9D:
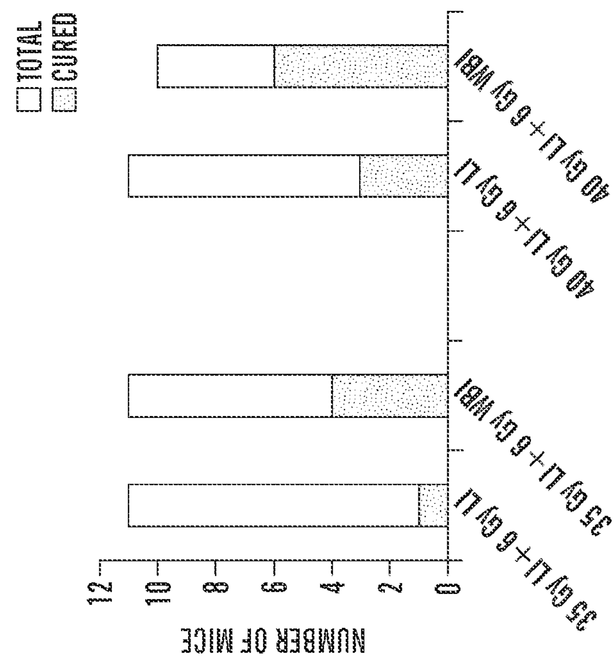
Figure 9C:
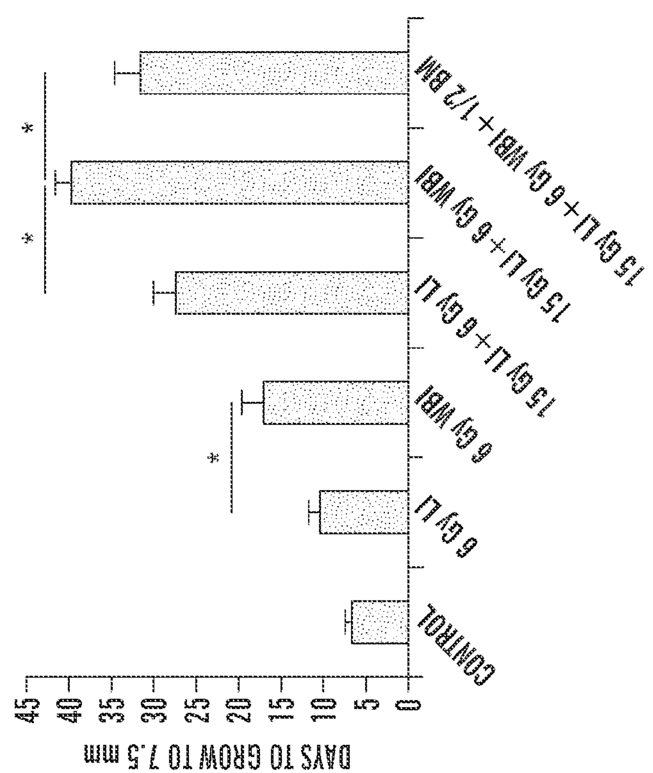

The infusion of unsorted BMDCs in mice treated with 15 Gy of LI plus 6 Gy of WBI abrogated the significant regrowth delay achieved by WBI in both tumor models FIGS. 9B-9C. The "tumor-rescuing" effect was greater for irradiated MCa8 tumors ($P<0.05$, FIG. 9C). Moreover, a similar effect was seen after the infusion of myeloid progenitor BMDCs ($Sca^{1+}$ $CD11b^+$) or more mature myeloid BMDCs ($Sca1^-CD11b^+$) in mice with 54A tumors treated with 15 Gy of LI plus 6 Gy of WBI (data not shown). These results indicate that the recruitment of radiation-naïve BMDCs could facilitate tumor regrowth after LI. As SDF-1α is a critical cytokine for BMDC recruitment (7), its intratumoral levels before and after LI were compared next.

LI Upregulates CXCL12 (SDF-1α) Expression in Tumors.

In both 54A and MCa8 models, 20 Gy of LI significantly increased CXCL12 protein expression in tumor tissues, as measured 2 days later FIG. 10A. In addition, a trend for increased CXCL12 expression was found even after irradiation at a dose of 4 Gy (FIG. 11). This rapid upregulation of CXCL12 is likely induced directly by radiation, and is consistent with previous reports of CXCL12 upregulation shortly after irradiation of normal tissues or cancer cells in vitro (19, 20), CXCL12 might also be upregulated at later time points if tumors become hypoxic (16). As CXCL12 is thought to exert its effects on BMDCs via the CXCR4 receptor (6, 21), whether CXCR4 blockade could delay tumor regrowth after LI was next tested.

CXCR4 Blockade Delays Tumor Regrowth Only when Administered Immediately after LI.

Figures 10A, 10B, 10C:
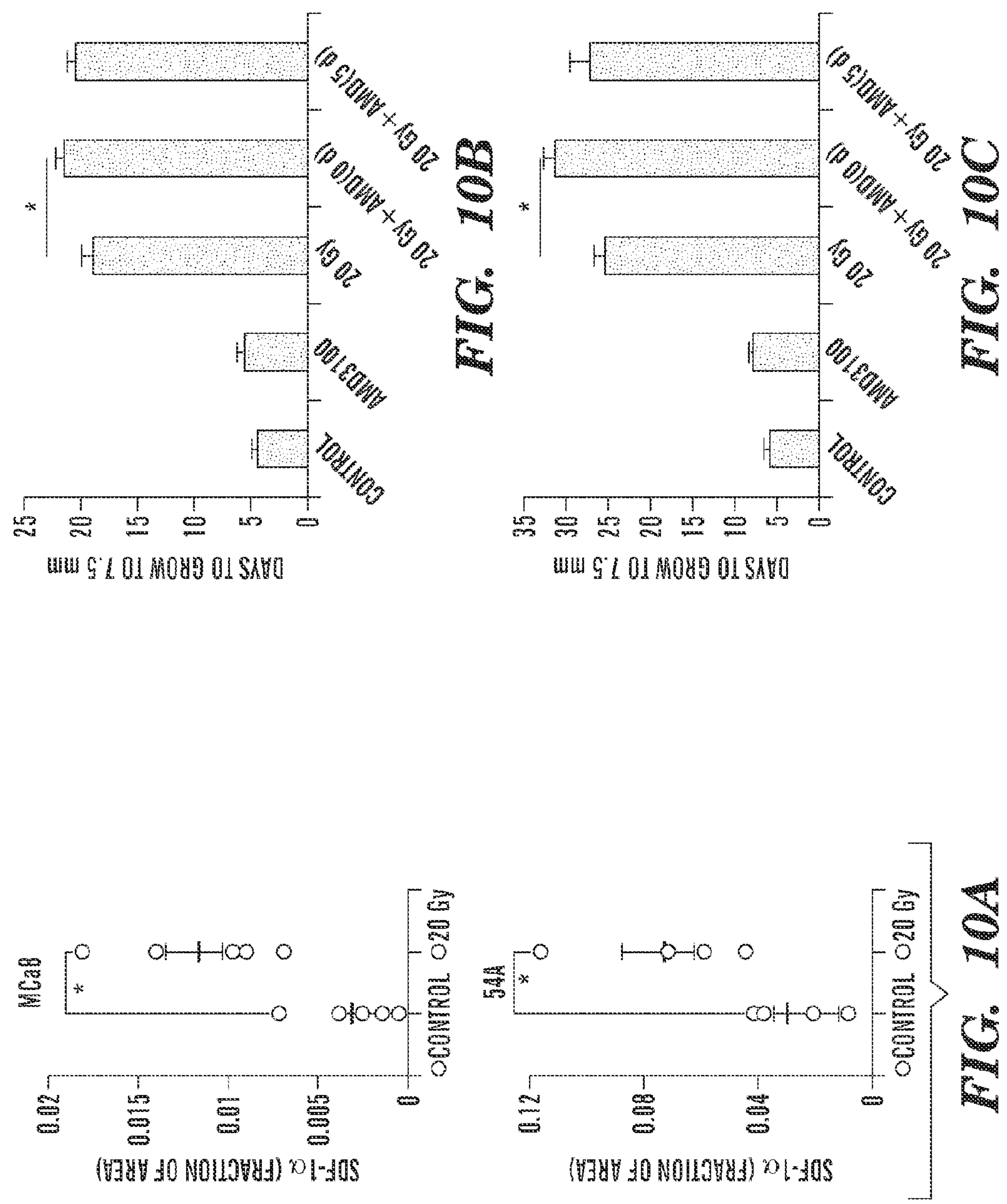
FIGS. 10A-10C demonstrate the role of the CXCL12 (SDF-1$\alpha$)/CXCR4 pathway in tumor regrowth after LI.

Inhibition of CXCL12/CXCR4 signaling for 2 weeks using AMD3100-containing osmotic pumps did not affect tumor growth but significantly inhibited tumor regrowth of both 54A and MCa8 tumors when commenced immediately after 20 Gy of LI (FIGS. 10B-10C). This is consistent with recent data from glioma xenografts (10). However, this effect was abrogated when AMD3100 treatment was initiated 5 days after 20 Gy of LI. On the other hand, the combination of AMD3100 with 6 Gy of WBI immediately after 15 Gy of LI provided no additional growth delay in MCa8 tumors (FIG. 12). This indicates that WBI and AMD3100 treatment have overlapping effects postirradiation. Collectively, these results suggest a critical role for the rapid, radiation-induced recruitment of BMDCs in tumors, mediated by CXCL12/CXCR4 signaling. Therefore, the early BMDC infiltration in tumors after the treatment regimens shown in FIG. 9A was examined.

Rapid Accumulation of Myeloid BMDCs Post-LI May Facilitate Tumor Relapse.

Tumor accumulation of myeloid BMDCs 3 days after radiation treatments was measured. Immunostaining for CD11b showed a significant increase in myeloid BMDC infiltration after LI alone in 54A tumors, whereas the regimens containing WBI abrogated this effect (FIG. 13A). Of interest, immunostaining for CD31 showed no significant change in tumor vessel density at day 3 in any group after radiation compared with nonirradiated tumors (FIG. 13A). Flow cytometric analysis of whole tumor lysates confirmed the significant increase in number of $CD11b^+$ cells after LI and its reduction by WBI, both in 54A and MCa8 tumors (FIGS. 13B-13C). Further phenotypic analyses showed that the vast majority of these cells were $F4/80^+$ macrophages. The number of $F4/80^+$ macrophages was also significantly decreased in tumors by WBI ($P<0.05$, using the linear contrast test for groups with versus without WBI). $CD11b^+Gr1^+$ immune-suppressive myeloid cells were elevated in tumors after 21 Gy of LI, but were not reduced by WBI. These results further support the importance of rapid myeloid cell accumulation for tumor resistance to LI. This LI-induced macrophage infiltration might also be associated with HIF-1α activation as well as inducible nitric oxide synthase and vascular endothelial growth factor overexpression and lead to better survival and further proliferation of irradiated endothelial cells (14).

TEM Infiltration but not EPC Vessel Incorporation is Increased in Recurring Tumors.

Finally, we tested the contribution of various BMDCs to tumors recurring after LI. Although incompletely understood, tumor angiogenesis post-LI might be deficient compared with nonirradiated tumors (11, 15). In this context, vasculogenesis by nonirradiated EPCs could play a more substantial role than in the case of radiation-naïve tumor growth. To test this, MCa8 tumor growing in chimeric wild-type/Tie2-GFP-BMT mice, a tumor model in which EPC recruitment is negligible in the absence of treatment (3) was used. No significant effect of the prior BMT on the tumor growth rate and the growth delay after 20 to 25 Gy of LI was detected, which suggested an efficient bone marrow reconstitution and a lack of apparent local "tumor bed effect" beyond 6 weeks after BMT in FVB mice. Because new vessel formation is mandatory only to support the increasing tumor mass postirradiation (10), EPC incorporation in the vasculature of relapsed tumors (i.e., when they reached a diameter of 7.5 mm) was analyzed. Tumor tissue analysis by confocal fluorescence microscopy showed no difference in $CD31^+$ microvascular density or total myeloid $CD11b^+$ BMDC infiltration between LI-treated tumors and size-matched nonirradiated tumors (FIGS. 14A-14B). However, the accumulation of Tie2-$GFP^+$ BMDCs was significantly increased in tumors recurring after LI. The vast majority of Tie2-$GFP^+$ BMDCs were $CD11b^+CD31^+$ myeloid cells localized in the tumor interstitium but not incorporated into the vessel wall. Thus, recurring tumors contained significantly more vascular-modulatory TEMs. In contrast, the number of EPCs incorporated in tumor vessels was substantially lower than TEM accumulation in tumor tissues and was not significantly different in recurring versus nonirradiated tumors. Collectively, these data support the potential role of TEM paracrine influence but not EPC-based vasculogenesis in recurring tumors after LI. The latter is consistent with the negligible incorporation of EPCs in the vasculature of tumors growing in preirradiated normal tissues (15).

Discussion

Presented herein are data indicating that host-derived BMDC infiltration in tumors is stimulated by LI and facilitates tumor recurrence through paracrine effects on irradiated tumor vasculature, inside and adjacent to the regressing/stabilized tumors. The rapid recruitment of nonirradiated myeloid BMDCs—primarily macrophages—is mediated at least in part by CXCL12 and may create a microenvironment that promotes the survival of tumors and endothelial cells and regrowth. Once tumors recur, an increased TEM, but not EPC infiltration, might promote tumor growth. These results suggest that targeting the CXCL12/CXCR4 pathway in a specific "therapeutic window" or TEM accumulation may delay tumor recurrence after radiotherapy.

REFERENCES FOR EXAMPLE 1

1. Coffelt S B, Lewis C E, Naldini L., Brown J M, Ferrara N, De Palma M. Elusive identities and overlapping phenotypes of proangiogenic myeloid cells in tumors. Am J Pathol 2010; 116:1564-76.
2. Rafii S, Lyden D, Benezra R, Hattori K, Heissig B. Vascular and haematopoietic stem cells: novel targets for anti-angiogenesis therapy? Nat Rev Cancer 2002; 2:826-35.
3. Duda D G, Cohen K S, Kozin S V, et al. Evidence for incorporation of bone marrow-derived endothelial cells into perfused blood vessels in tumors. Blood 2006; 107: 2774-6.
4. De Palma M, Venneri M A, Galli R, et al. Tie2 identifies a hematopoietic lineage of proangiogenic monocytes required for tumor vessel formation and a mesenchymal population of pericyte progenitors. Cancer Cell 2005; 8:211-26.
5. Loges S, Schmidt T, Carmeliet P. "Antimyeloangiogenic" therapy for cancer by inhibiting PIGF. Clin Cancer Res 2009; 15:3648-53.
6. R, Lu K V, Petritsch C, et al. HIF1α induces the recruitment of bone marrow-derived vascular modulatory cells to regulate tumor angiogenesis and invasion. Cancer Cell 2008; 13:206-20.
7. Grunewald M, Avraham I, Dor Y, et al. VEGF-induced adult neovascularization: recruitment, retention, and role of accessory cells. Cell 2006; 124:175-89.
8. Shaked Y, Ciarrocchi A, Franco M, et al. Therapy-induced acute recruitment of circulating endothelial progenitor cells to tumors. Science 2006; 313:1785-7.

9. Shaked Y. Henke E, Roodhart J M, et al. Rapid chemotherapy-induced acute endothelial progenitor cell mobilization: implications for antiangiogenic drugs as chemosensitizing agents. Cancer Cell 2008; 14:263-73.
10. Denekamp J. Limited role of vasculature-mediated injury in tumor response to radiotherapy. J. Natl. Cancer Inst 1993:85:935-7.
11. Kozin S V, Winkler F. Garkavtsev I, Hicklin D J, Jain R K, Boucher Y. Human tumor xenografts recurring after radiotherapy are more sensitive to anti-vascular endothelial growth factor receptor-2 treatment than treatment-naive tumors. Cancer Res 2007; 67:5076-82,
12. Stephens T C, Currie G A, Peacock J H. Repopulation γ-irradiated Lewis lung carcinoma by malignant cells and host macrophage progenitors. Br J Cancer 1978; 38:573-82.
13. Jung H, Kruger H J, Brammer I, Zywietz F, Beck-Bornholdt H P. Cell population kinetics of the rhabdomyosarcoma R1H of the rat after single doses of X-rays. Int J Radiat Biol 1990; 57:567-89.
14. Li F, Sonveaux P, Rabbani Z N, et al. Regulation of HIF-1α stability through S-nitrosylation. Mol Cell 2007; 26:63-74.
15. Ahn G O, Brown J M. Matrix metalloproteinase-9 is required for tumor vasculogenesis but not for angiogenesis: role of bone marrow-derived myelomonocytic cells. Cancer Cell 2008; 13:193-205.
16. Kioi M, Vogel H, Schultz G, Hoffman R M, Harsh G R, Brown J M. Inhibition of vasculogenesis, but not angiogenesis, prevents the recurrence of glioblastoma after irradiation in mice. J Clin Invest 2010; 120:694-705.
17. Heissig B, Rafii S, Akiyama H, et al. Low-dose irradiation promotes tissue revascularization through VEGF release from mast cells and MMP-9-mediated progenitor cell mobilization, J Exp Med 2005; 202:739-50.
18. Seung L P, Weichselbaum R R, Toledano A, Schreiber K, Schreiber H. Radiation can inhibit tumor growth indirectly while depleting circulating leukocytes. Radiat Res 1996; 146:612-8.
19. Zong Z W, Cheng T M, Su Y P, et al. Recruitment of transplanted dermal multipotent stem cells to sites of injury in rats with combined radiation and wound injury by interaction of SDF-1 and CXCR4. Radiat Res 2008; 170:444-50,
20. Tabatabai G, Frank B, Mohle R, Weller M. Wick W. Irradiation and hypoxia promote homing of haematopoietic progenitor cells towards gliomas by TGF-β-dependent HIF-1α-mediated induction of CXCL12. Brain 2006; 129: 2426-35.
21, Jin D K, Shido K, Kopp H G, et al. Cytokine-mediated deployment of SDF-1 induces revascularization through recruitment of CXCR4$^+$ hemangiocytes, Nat Med 2006; 12:557-67.

Example 2

C—X—C Receptor Type 4 Promotes Metastasis by Activating p38 Mitogen-Activated Protein Kinase in Myeloid Differentiation Antigen (Gr-1)-Positive Cells Materials and Methods Reagents.

Human recombinant (r)VEGF (National Cancer Institute), mouse rCXCL12 and rPlGF (R&D Systems), AMD3100 (Sigma), Alzet osmotic pumps (DURECT), p38 MAPK and phospho-p38 MAPK antibodies (Cell Signaling), and a p38 inhibitor (Invitrogen) (SI Materials and Methods) were used. TRAMP-C1 prostate cancer cells were purchased from ATCC. The E0771 breast cancer cell line was originally established by F. M. Sirotnak and kindly provided by E. Mihich (Roswell Park Memorial Institute) (34). Both cell lines are derived from tumors from C57BL/6 mice.

Animals.

All animal procedures were performed following the guidelines of the Public Health Service Policy on Humane Care of Laboratory Animals and approved by the Institutional Animal Care and Use Committee of the Massachusetts General Hospital. VEGFR1$^{TK-/-}$ mice were kindly provided by M. Shibuya at the University of Tokyo (36). To obtain double knockout mice, CXCR4$^{+/-}$ mice (The Jackson Laboratory; #004341, B6.129x-CXCR4tm1Qma/J) were mated with VEGFR1$^{TK-/-}$ mice to generate CXCR4$^{+/-}$VEGFR1$^{TK-/-}$ mice. Next, CXCR4$^{+/-}$VEGFR1TK$^{-/-}$ mice were cross-bred with MxCre-CXCR4$^{flox/flox}$ mice (37) to generate MxCre-CXCR4$^{flox/-}$VEGFR1$^{TK-/-}$ mice. C57BL/6 (#000664) and Actb-GFP [#003291, C57BL/6-Tg(CAG-EGFP)1Osb/J, constitutively expressing EGFP] mice were obtained from the The Jackson Laboratory. All mice were backcrossed to 99.9% C57BL/6 strain background (N10 equivalent). Strain background was verified by the The Jackson Laboratory Speed Congenic Development Service.

Bone Marrow Transplantation.

C57BL/6 mice (8 wk old) were lethally irradiated (137 Cs Irradiator; Atomic Energy of Canada) using one 12-Gy fraction delivered to the whole body. Irradiated mice were rescued 24 h later by a bone marrow transplant isolated from Actb-GFP/C57BL/6. Eight weeks after BMT, we confirmed over 90-95% reconstruction from GFP-bone marrow cells using flow cytometry analyses. After the irradiation condition was set up for C57BL/6 mice, BMT was carried out using several genotyped mice. The following were used as bone marrow donors: WT C57BL/6 mice, VEGFR1$^{TK-/-}$ mice, MxCre-CXCR4$^{flox/-}$VEGFR1$^{TK-/-}$ mice, MxCre-CXCR4$^{flox/-}$VEGFR1$^{TK-/-}$ mice, or MxCre-CXCR4$^{flox/-}$VEGFR1$^{TK-/-}$ in the control group. Cre expression (and hence CXCR4 deficiency in BMDCs) was induced by seven weekly i.p. injections of poly (I) poly (C) (250 μg per body; Invitrogen) in the BMT mice, as described previously (37). Tumor implantations were performed after 8 wk (1 wk after the last i.p. injection).

Tumor Implantation and Metastasis Assay.

TRAMP-C1 tumors were implanted s.c. in male C57BL/6 mice, and E0771 tumors were implanted s.c. in female C57BL/6 mice after BMT and recovery and/or after BMT and Mx-Cre recombination (n=5-6 mice) (SI Materials and Methods). Primary tumors were resected when they reached a diameter of 10 mm (TRAMP-C1) or 13 mm (E0771), sizes that have been shown to reproducibly induce lung metastasis in pilot studies. Lung tissue was isolated from mice 2-4 wk after removal of the primary tumor.

Pharmacologic CXCR4 Inhibition Using AMD3100.

AMD3100 was delivered by s.c. Alzet pumps containing 10 mg/mL AMD3100 in PBS at a dose of 60 μg/day, and pumps with PBS only were used as a control. The pumps were replaced every 2 wk.

Immunohistochemistry and Western Blot Analysis.

Primary tumor tissues were fixed and frozen. Sections were stained with rat antibodies against mouse CD11b, MECA 32, Gr-1 (BD Pharmingen), and F4/80 (Serotec). Cy3- or FITC-conjugated secondary antibodies were used for the detection of signals by confocal microscopy. Slides were counterstained with DAPI for nuclear staining. The number of cells was quantified by measuring the area occupied by immunostained mononuclear cells normalized by the area of DAPI-stained nuclei (i.e., unitless). Phopho-p38 MAPK level was measured by Western blotting.

Isolation of Mononuclear Cells and CD11b+, F4/80+, and Gr-1+ BMDCs.

Bone marrow cells were collected in heparin-mixed PBS. The cellular filtrate was washed and a layer containing mononuclear BM cells was separated using Histopaque-1083 (Sigma). For the migration assay, BM cells were separated by CD11b, F4/80, or Gr-1 magnetic microbeads (MACS-beads; Miltenyi Biotech) from VEGFR1TK+/+ and VEGFR1TK−/− mice as per manufacturer's protocol. These cells were incubated with recombinant proteins for migration assays Statistical Analysis.

All data are expressed as mean±SEM. The Student t test was used for all analyses. A p value of less than 0.05 was considered to be statistically significant.

Reagents.

Human recombinant VEGF was supplied by the National Institute of Cancer Research Resources. Recombinant mouse CXCL12 (SDF1$\alpha$) and placental growth factor (PlGF) 2 were purchased from R&D Systems, AMD3100 from Sigma-Aldrich, Alzet osmotic pumps (type 1002) from DURECT, p38 MAPK (#9212) and phospho-p38 MAPK (Thr180/Tyr182) (D3F9) XP antibodies (#4511) from Cell Signaling, and the p38 MAPK inhibitor (SB203580) from Invitrogen.

Tumor Implantation and Metastasis Assay.

Mice ranging from 8 to 22 wk old [due to prior bone marrow transplantation (BMT) and/or recombination procedures] were used. Mice were s.c. injected into the hind limbs with an optimal number of cells established in studies to provide reproducible tumor growth: $5\times10^6$ E0771 cells and $1\times10^7$ TRAMP-C1 cells in mice regardless of age. All experiments were performed at least twice. Metastatic tumor volume was measure by the formula: V=small diameter×long diameter×number of microscopic metastases.

Immunohistochemistry.

Primary tumor tissues were fixed in 4% paraformaldehyde at 4° C. for 2 h, dehydrated in 30% sucrose overnight, and embedded in optimal cutting temperature (OCT) compound in frozen samples for immunofluorescence histological analyses.

Western Blot Analysis.

Bone marrow-derived cells (BMDCs) were lysed with lysis buffer (50 mM Hepes, pH 7.4, 1% Triton X100, 150 mM sodium chloride, 1 mM EGTA, and 5 mM EDTA) with protease inhibitor mixture, 1 mM phenylmethylsulfonyl fluoride, 1 mM sodium fluoride, and 1 mM sodium orthovanadate. Phopho-p38 MAPK signals were detected by anti-phosphop38 MAPK antibody (Cell Signaling) and normalized by total p38 MAPK expression level in BMDCs.

In Vitro Migration Assay.

The migration of mononuclear CD11b+ BMDCs (2×106 cells per mL), F4/80+ BMDCs (8×105 cells per mL), and Gr-1+ BMDCs (8×105 cells per mL) was evaluated using a chemotaxis Boyden chamber (Neuroprobe). The upper and lower wells were separated by a 5-1 μm pore size polyvinylpyrrolidone-free polycarbonate filter (Nucreopore; Costar). The chemoattractants (recombinant CXCL12, VEGF, or PlGF) were added in the lower wells, and the p38 inhibitor (Promega) was added to both lower and upper wells. Chemotaxis activity was checked in myeloid BMDCs using various concentrations (from 10 pg/mL to 1 μg/mL) of rCXCL12 and rVEGF and used 100 ng/mL for all experiments because a peak in migration index was found at this concentration. A 50-μl aliquot of the cell suspension was seeded in the upper wells and incubated for 3 h at 37° C. with 5% CO2. The number of cells that migrated through the membrane was counted.

Introduction

To form distant metastases, cancer cells must have the ability to survive and reach the distal organ through circulation, extravasate, invade, and grow into a macroscopic tumor while evading the immune system (1). The efficiency of this multistep process is governed by interactions between the cancer cells and the host cells (1, 2).

Increasing evidence supports a critical role for the interaction between cancer cells and myeloid (CD11b+) bone marrow-derived cells (BMDCs) during tumor growth and metastasis. Myeloid BMDCs are mobilized into blood circulation and infiltrate the neoplastic tissues from early stages of tumor growth in response to tumor- and stroma-derived cytokines (3). Upon recruitment to the tumor, some of these inflammatory cells can facilitate new blood vessel formation either by directly incorporating into the vessel wall or by secreting factors that promote angiogenesis and activate stromal fibroblasts (4-6). For example, both tumor-associated macrophages (TAMs) and myeloid differentiation antigen (Gr-1)-positive myeloid BMDCs can promote angiogenesis and tumor progression (5). Of the cytokines that contribute to recruitment of myeloid BMDCs, VEGF, and placental growth factor (PlGF) may play important roles by activating their cognate tyrosine kinase (TK) receptor VEGF receptor 1 (VEGFR1) in TAMs (7). In particular, phosphorylation of p38 mitogen-activating protein kinase (p38 MAPK) is important for monocyte migration in response to VEGFR1 activation by VEGF or PlGF (8). However, recruitment by tumors of other myeloid BMDCs—such as Gr-1+ BMDCs—is independent of VEGF or VEGFR1 activity (9, 10). This may be critical for early metastatic growth because Gr-1+ myeloid BMDCs can promote tumor growth and mediate tumor resistance to anti-VEGF therapy (5, 10).

Because Gr-1+ myeloid BMDCs express C—X—C receptor type 4 (CXCR4 or fusin) in addition to VEGFR1, whether the chemokine (C—X—C motif) ligand 12 (CXCL12)/CXCR4 pathway compensates for inhibition of VEGFR1 activity in BMDCs and lead to tumor infiltration by these cells and promotion of metastasis was examined. The effect of genetic ablation of CXCR4 was first evaluated—with or without inhibition of VEGFR1-TK activity—in BMDCs on primary tumor growth and metastasis in highly metastatic tumor models of breast and prostate cancer. Then, whether pharmacologic blockade of CXCR4 overcomes resistance to VEGFR1-TK inhibition in myeloid BMDCs and inhibit metastasis was examined.

Results

Deletion of CXCR4 in BMDCs Has Moderate Effects on Primary Tumor Growth but Substantially Reduces Metastasis Independently of VEGFR1-TK Activity in BMDCs.

Figure 1A:
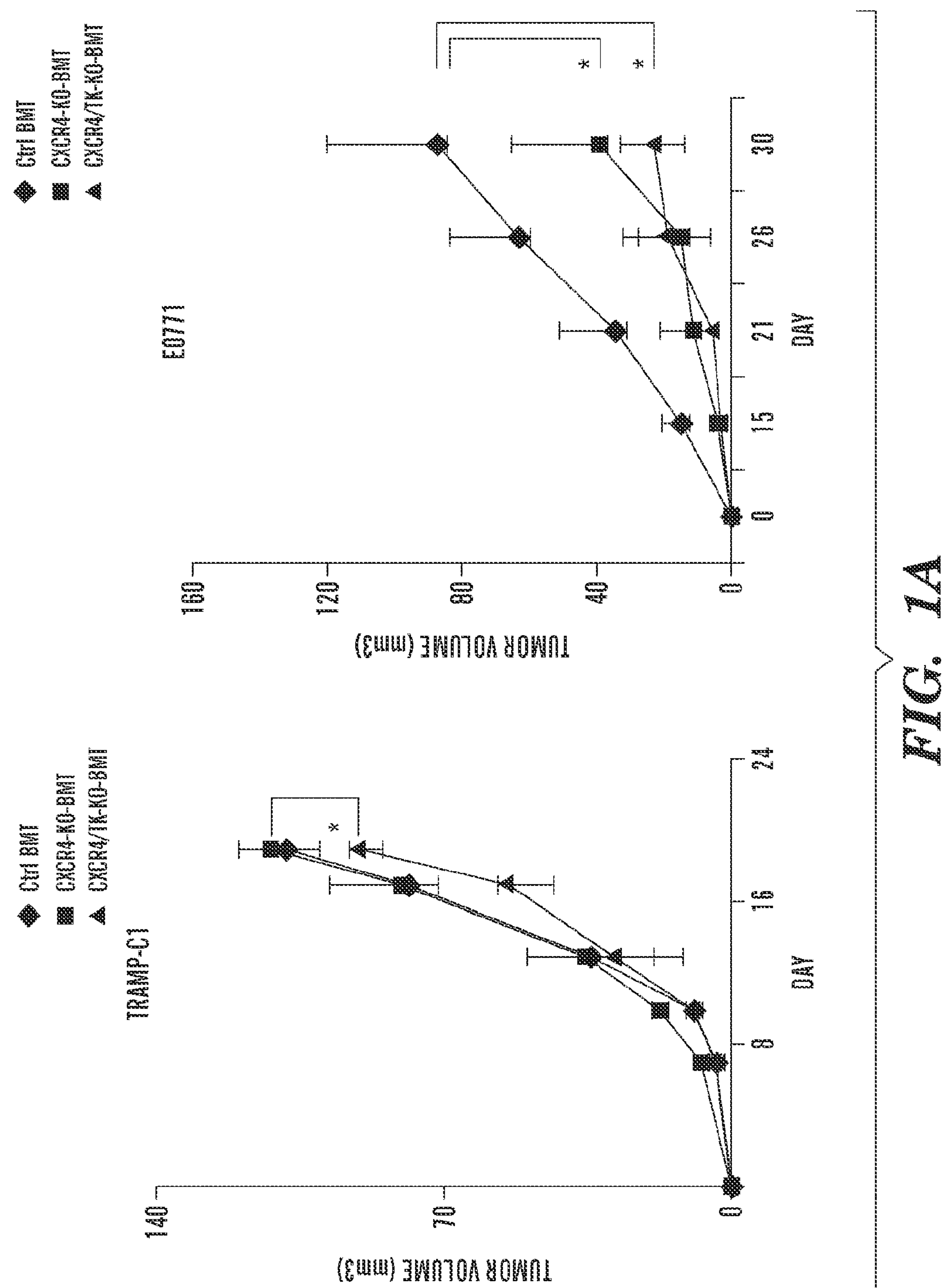
FIGS. 1A-1C demonstrate specific inhibition of CXCR4 in BMDCs induces slight delays in tumor growth but potently inhibits lung metastasis.
Figure 1B:
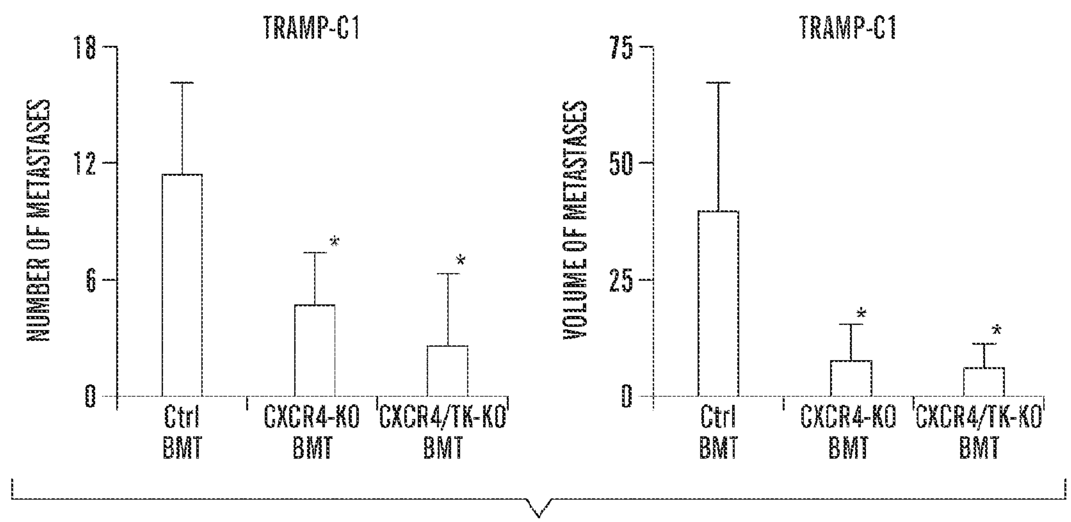
Figure 1C:
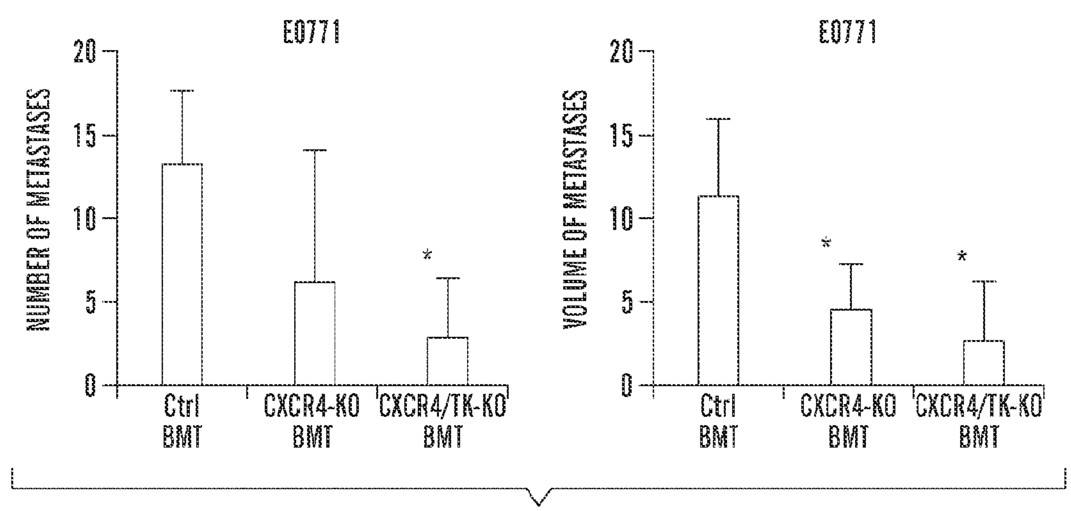

Because CXCR4−/− mice are embryonically lethal and because CXCR4 is a critical player in hematopoietic stem cell trafficking, CXCR4 deficiency was induced in BMDCs after restorative bone marrow transplantation (BMT) in C57BL/6 mice using MxCre-CXCR4$^{flox/-}$ mice as donors. Cre expression was then induced to generate CXCR4$^{-/-}$ BMDCs in the BMT mice (referred heretofore as BMT-CXCR4$^{-/-}$ mice; see Materials and Methods). To achieve inhibition of both CXCR4 and VEGFR-TK activity in BMDCs, BMT from MxCre-CXCR4$^{flox/-}$ VEGFR1$^{TK-/-}$ donor mice to lethally irradiated C57BL/6 mice was performed and the CXCR4 null phenotype was then induced in BMDCs (referred herein as "BMT-CXCR4$^{-/-}$VEGFR1$^{TK-/-}$"). Next we evaluated the growth rate of TRAMP-C1 prostate tumors and E0771 mammary tumors in mice with BMDCs deficient for only CXCR4 or for both CXCR4 and VEGFR1-TK versus control (Materials and Methods). Both TRAMP-C1 and E0771 cells express detectable levels of CXCR4 transcripts by RT-PCR. However, BMDC-specific deficiency in CXCR4 and VEGFR1-TK induced a modest growth delay in both tumors, and BMDC-specific deficiency in CXCR4 alone induced a growth delay in the E0771 mammary carcinoma (FIG. 1A). More importantly, lung metastatic burden after primary tumor resection was reduced by more than twofold in BMT-CXCR4$^{-/-}$ mice and by more than threefold in BMT-CXCR4$^{-/-}$VEGFR1$^{TK-/-}$ mice (FIGS. 1B and 1C). Thus, BMDC-specific inhibition of CXCR4 reduces metastasis—with or without VEGFR1-TK inhibition—despite the minimal delay in primary tumor growth. To dissect the mechanisms by which CXCR4 activity in BMDCs mediates metastasis, tumor angiogenesis and myeloid BMDC infiltration was evaluated in the primary tumors.

CXCR4 Deletion in BMDCs Reduces Primary Tumor Angiogenesis Independently of VEGFR1-TK Activity in BMDCs.

Figure 2A:
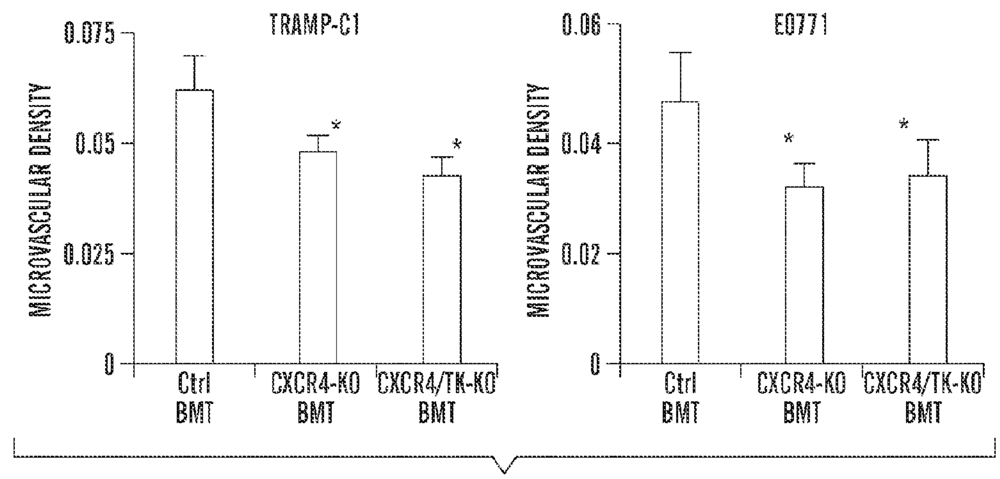
FIGS. 2A-2D demonstrate specific inhibition of CXCR4 in BMDCs decreases tumor angiogenesis and Gr-1$^{+}$ myeloid BMDC recruitment.

Microvascular density (MVD) was measured by quantitative immunostaining for MECA32 in sections from size-matched primary tumors (Materials and Methods). MVD was significantly decreased in both tumor models when grown in BMT-CXCR4$^{-/-}$ or BMT-CXCR4$^{-/-}$ VEGFR1TK$^{-/-}$ mice compared with control BMT mice (FIG. 2A). Thus, the effect of CXCR4 deletion in BMDCs on metastasis can at least in part mediated by inhibition of angiogenesis.

CXCR4 Deletion in BMDCs Reduces the Number of Tumor-Infiltrating Gr-1+ Myeloid BMDCs Independently of VEGFR1-TK Activity in BMDCs.

Figure 2B:
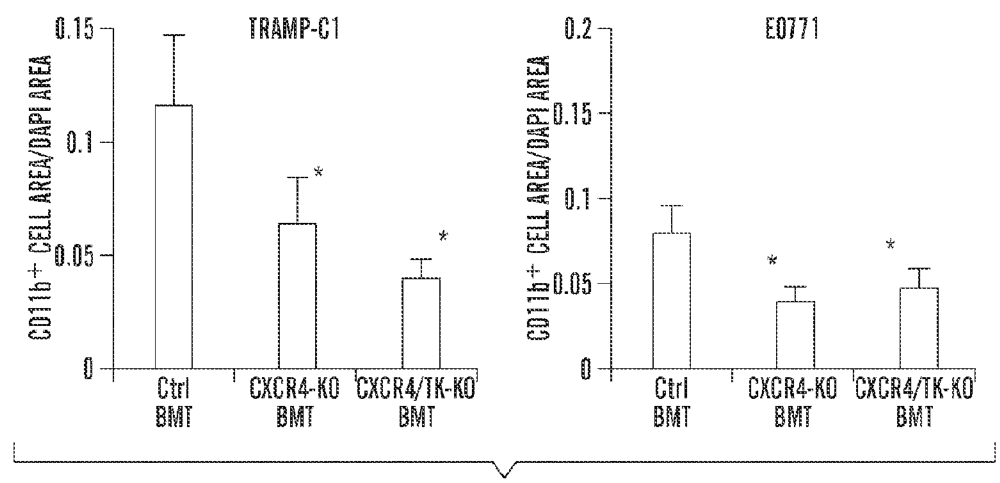
Figure 2C:
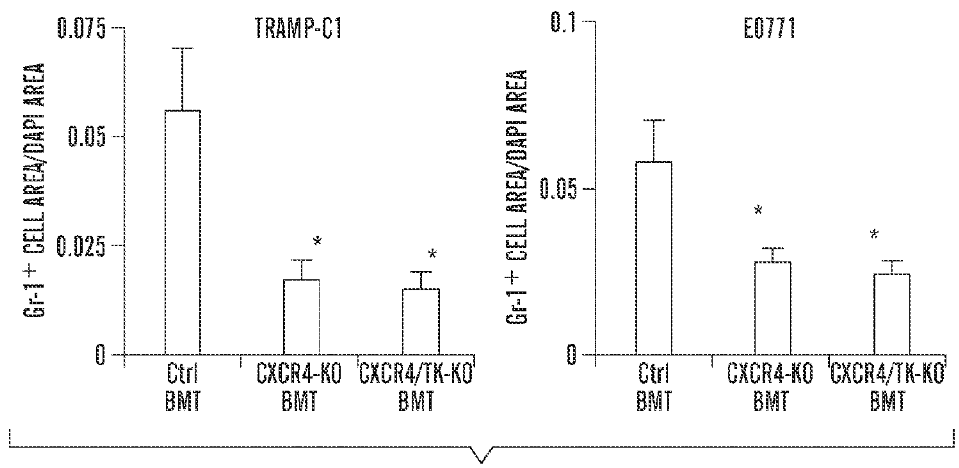
Figure 2D:
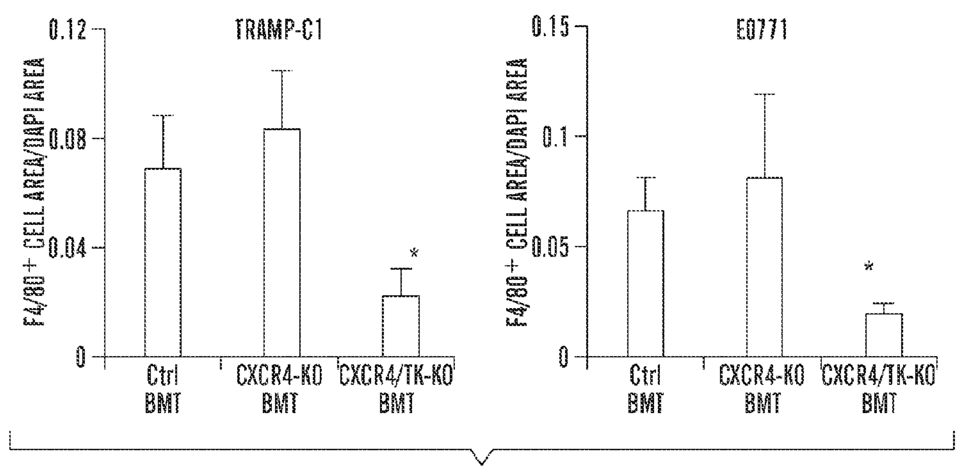

In addition, the tumor-infiltrated myeloid BMDCs were evaluated by quantitative immunostaining with myeloid markers in sizematched primary tumors (Materials and Methods). In both tumor models, the total number of tumor-infiltrating myeloid BMDCs was significantly decreased in mice deficient for CXCR4 in their BMDCs (FIG. 2B). However, further analysis of myeloid (CD11b+) BMDC subsets showed that, whereas the tumor infiltration by Gr-1+ BMDCs was decreased in both BMT-CXCR4$^{-/-}$ and BMT-CXCR4$^{-/-}$ VEGFR1$^{TK-/-}$ mice, the number of F4/80+ TAMs was reduced only in mice with BMDCs deficient in VEGFR1-TK (FIGS. 2C and 2D). Thus, the effect of CXCR4 inhibition in BMDCs on metastasis can be mediated by Gr-1+ myeloid BMDC recruitment to tumors. Next, to dissect the roles of CXCR4 and VEGFR1-TK in specific BMDC populations and to gain further insight into the kinetics of Gr-1+ myeloid BMDC recruitment to tumors, treatment with the CXCR4 inhibitor AMD3100 at different time points during tumor growth in BMT-VEGFR1$^{TK-/-}$ mice and C57BL/6 mice (Materials and Methods) was used.

Pharmacologic Blockade of CXCR4 Efficiently Delays Tumor Growth and Reduces Metastasis Only in Mice with VEGFR1-TK-Deficient BMDCs.

Figure 3C:
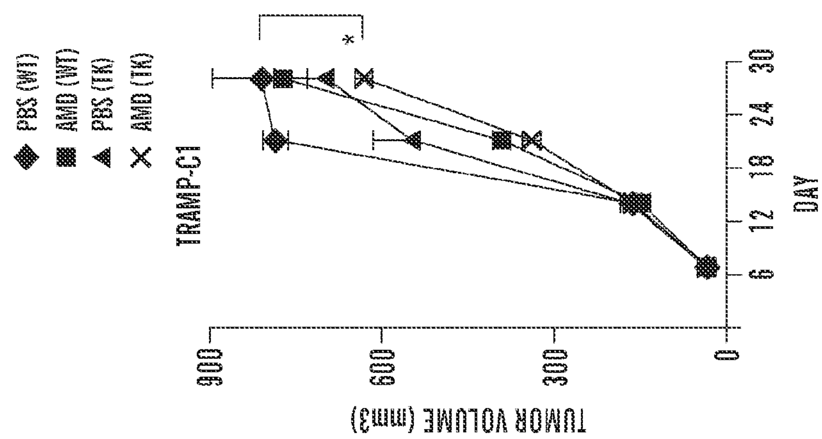
FIGS. 3A-3E demonstrate pharmacologic blockade of CXCR4 results in a substantial tumor growth delay only when combined with VEGFR1-TK inhibition and inhibits lung metastasis in a tumor-dependent manner.
Figure 3B:
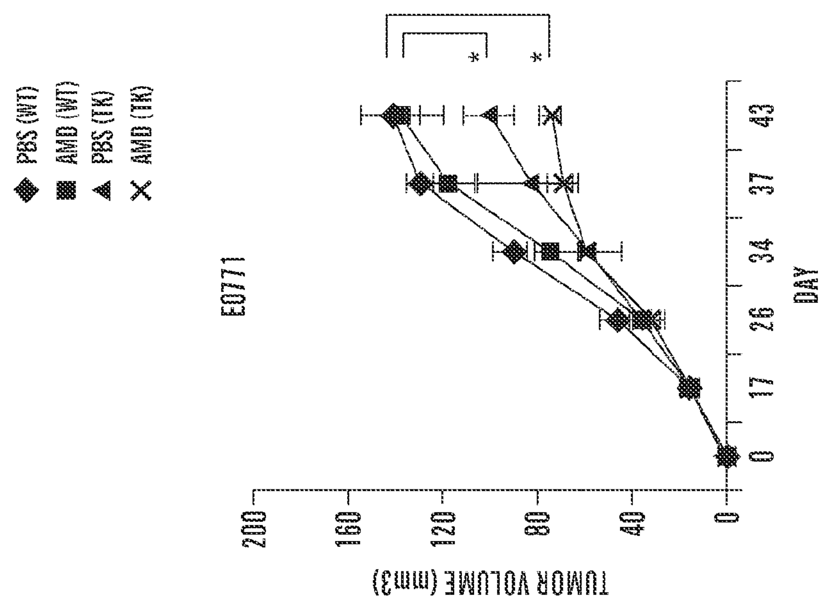
Figure 3A:
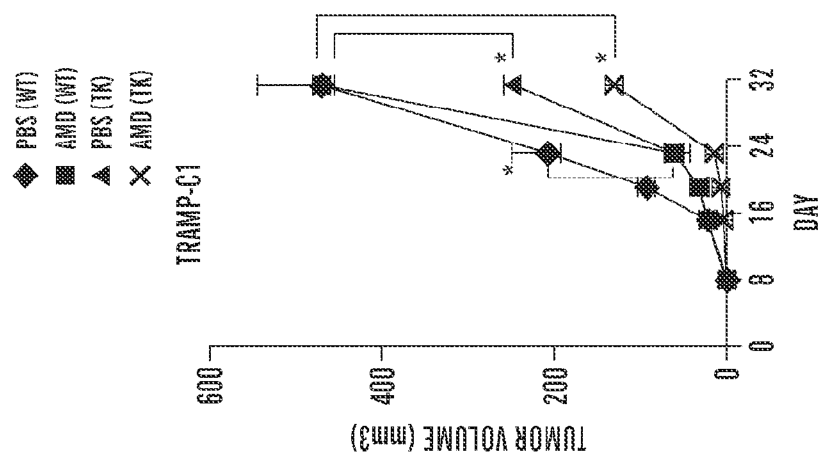

First, the effect of CXCR4 inhibition alone was tested by delivering AMD3100 using osmotic pumps from the time of tumor implantation (i.e., in a prevention setting). Consistent with the genetic deficiency model, AMD3100 treatment induced a minor and transient delay in the early growth of TRAMP-C1 and E0771 tumors (FIGS. 3A and 3B). On the other hand, whereas VEGFR1-TK inhibition in BMDCs induced a minor tumor growth delay in E0771 and TRAMP-C1 tumors, AMD3100 treatment substantially delayed tumor growth in BMT-VEGFR1$^{TK-/-}$ mice (FIGS. 3A and 3B).

Next, the effect of AMD3100 treatment on the growth of established tumors (in an intervention setting, i.e., with the time for growth from 4 mm to ~1 cm in diameter) was tested. Treatment with AMD3100 induced a less substantial growth delay in established TRAMP-C1 tumors, which was maintained after 4 wk of treatment only in BMT-VEGFR1$^{TK-/-}$ mice (FIG. 3C).

Figure 3D:
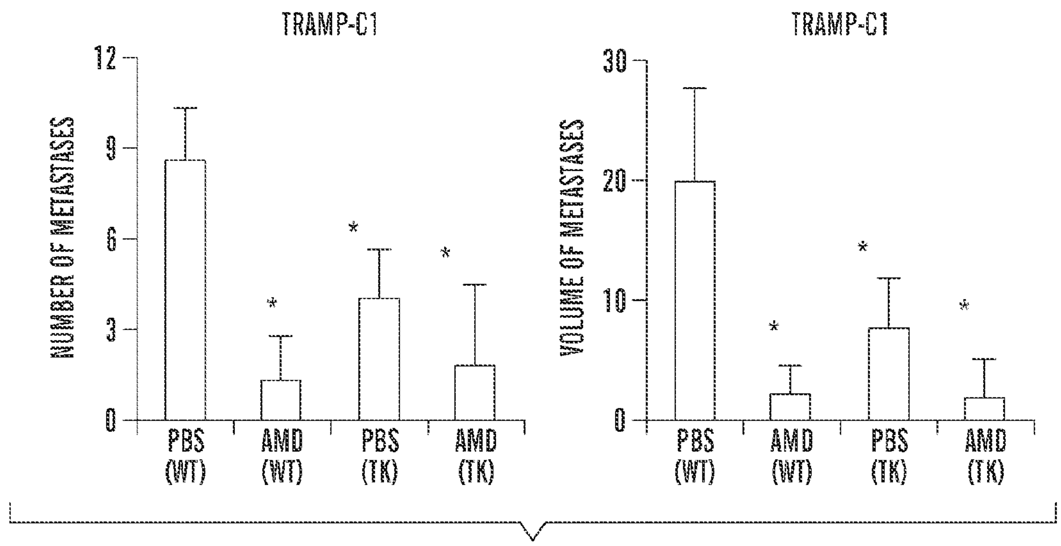
Figure 3E:
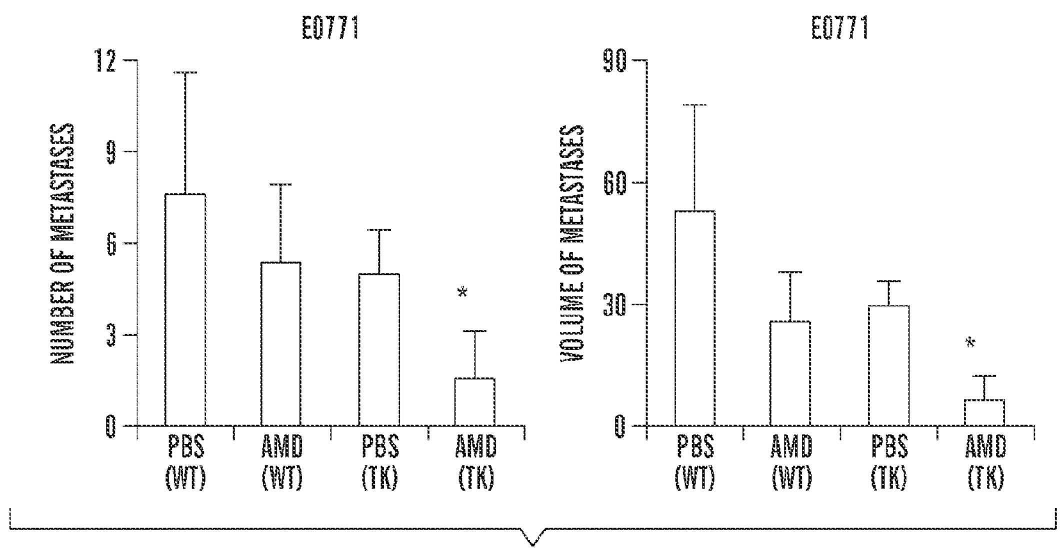

Finally, spontaneous lung metastasis was evaluated after primary tumor resection. AMD3100 treatment significantly reduced metastatic burden in both tumor models only in BMT-VEGFR1$^{TK-/-}$ mice (FIGS. 3D and 3E). As seen in the genetic model of CXCR4 deficiency in BMDCs (FIGS. 1B and 1C), the inhibition of metastasis by AMD3100 treatment alone was significant only in the TRAMP-C1 model (FIGS. 3D and 3E). Thus, the effect of CXCR4 inhibition on metastasis is tumor-dependent, and inhibition of both CXCR4 and VEGFR1-TK in BMDCs is required to achieve a significant tumor growth delay and reduction of lung metastasis. The effects of AMD3100 treatment on tumor angiogenesis and myeloid BMDC infiltration in size-matched primary tumors was evaluated next.

CXCR4-Mediated Gr-1+ BMDC Infiltration Promotes Early Tumor Growth and Metastasis.

Figure 4A:
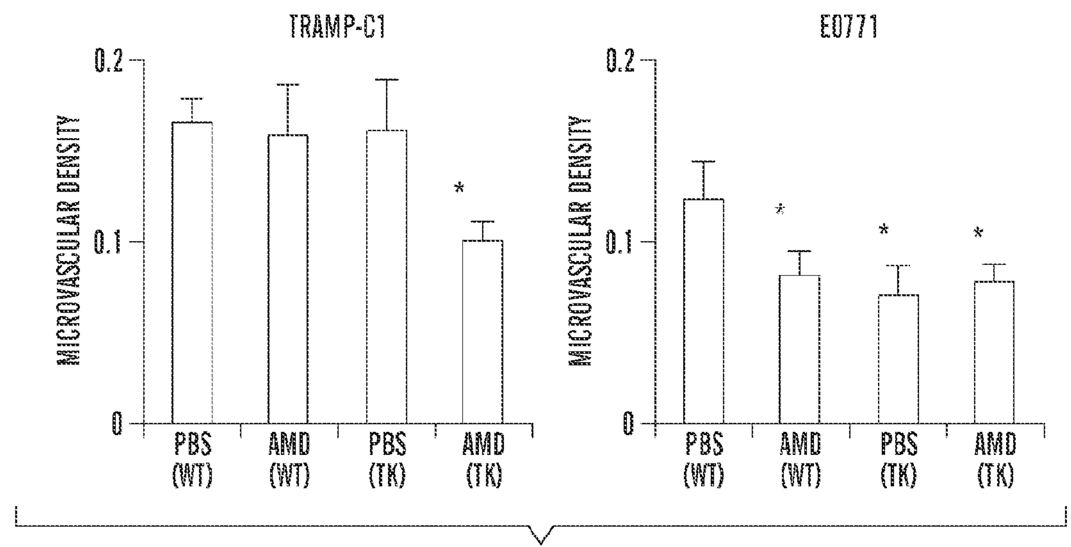
FIGS. 4A-4D demonstrate pharmacologic blockade of CXCR4 consistently decreases tumor angiogenesis and overall myeloid BMDC recruitment only in BMT-VEGFR1TK$^{-/-}$ mice.
Figure 7:
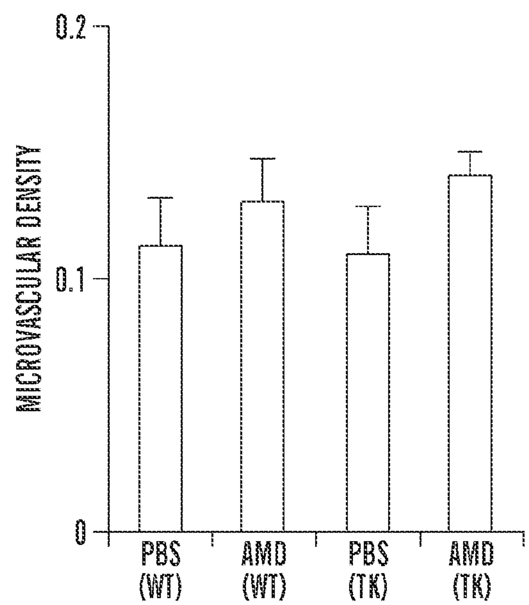
FIG. 7 shows pharmacologic blockade of CXCR4 does not decrease angiogenesis when administered to mice with established tumors, irrespective of VEGFR1-TK status in BMDCs. CXCR4 blockade with AMD3100 pumps (AMD) does not change tumor microvascular density in established TRAMP-C1 tumors in C57BL/6 (WT) or in BMT-VEGFR1$^{TK-/-}$ mice (TK) compared with PBS-treated WT or TK mice.

AMD3100 treatment alone decreased MVD when administered in a prevention setting in E0771 tumors but not in TRAMP-C1 tumors (FIG. 4A). However, AMD3100 treatment decreased MVD in both tumors when grown in BMT-VEGFR1$^{TK-/-}$ mice (FIG. 4A). AMD3100 treatment had no effect on MVD when administered in an interventional setting (to established tumors), irrespective of VEGFR1-TK status in BMDCs (FIG. 7).

Figure 4B:
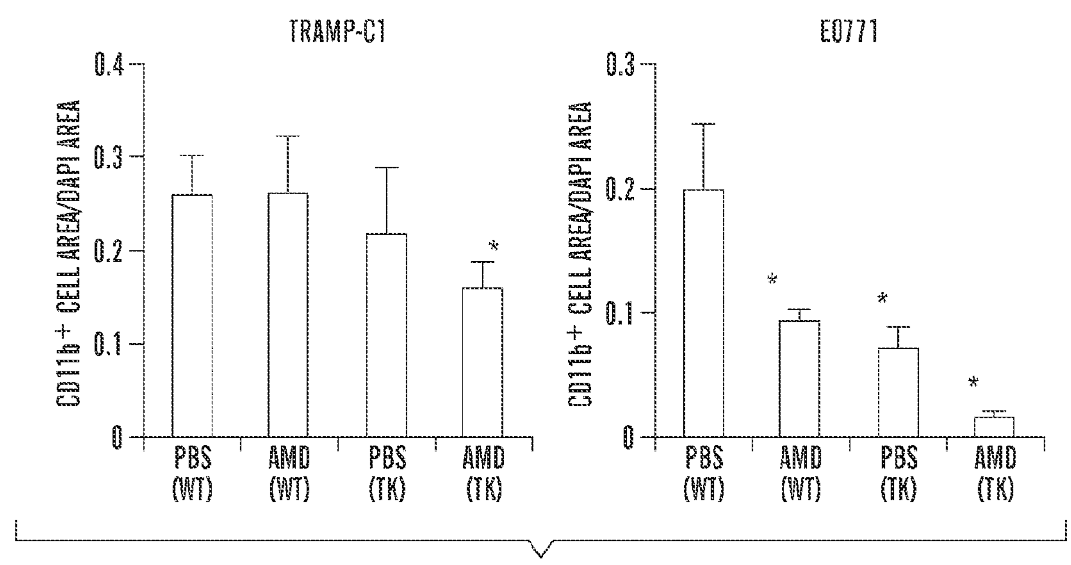
Figure 4C:
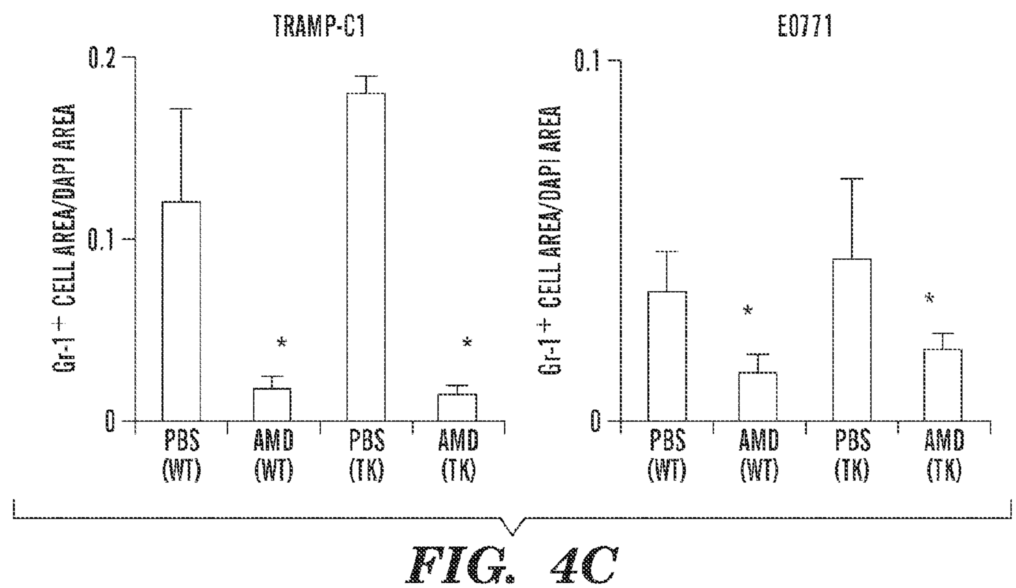
Figure 4D:
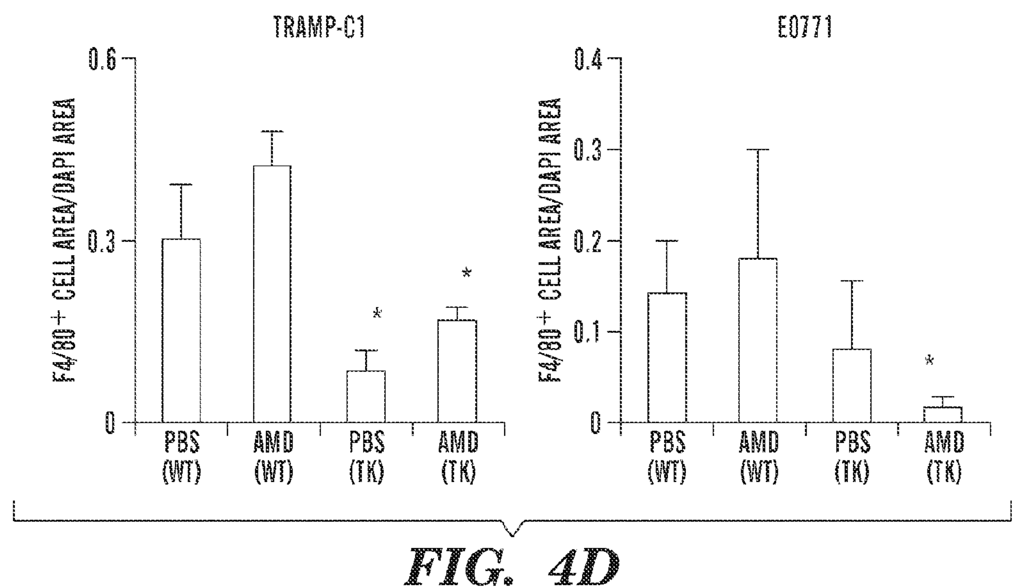

Similarly, AMD3100 treatment alone decreased the number of total myeloid BMDCs only in E0771 tumors, but not in TRAMP-C1 tumors, and decreased the number of myeloid BMDCs in both tumors when grown in BMT-VEGFR1$^{TK-/-}$ mice (FIG. 4B). However, AMD3100 treatment decreased Gr-1+ myeloid BMDCs in both tumors irrespective of VEGFR1-TK status in BMDCs (FIG. 4C). Consistent with data from the genetic deficiency model, CXCR4 inhibition by AMD3100 treatment did not affect the TAM infiltration in the tumors. However, when combined with VEGFR1-TK deficiency in BMDCs, CXCR4 blockade showed significantly decreased TAM infiltration in both tumor models (FIG. 4D).

Figure 8:
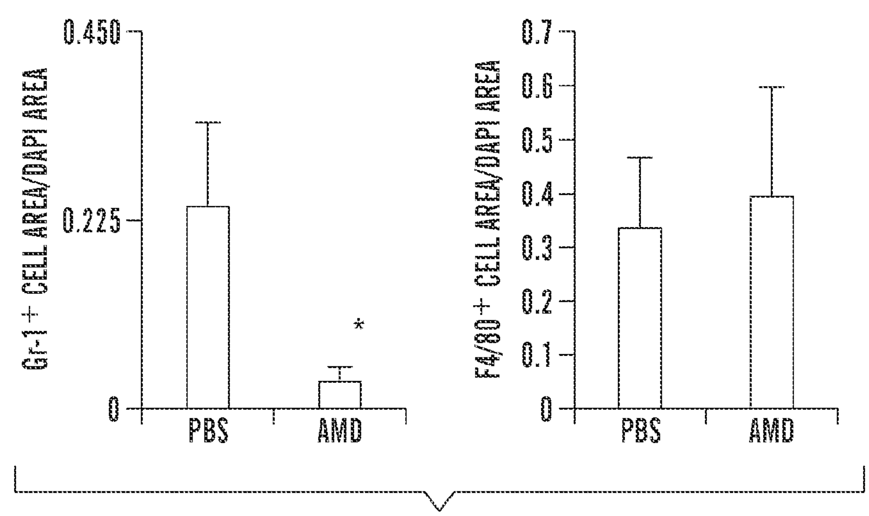
FIG. 8 demonstrates pharmacologic blockade of CXCR4 decreases Gr-1$^{+}$ myeloid BMDC recruitment but does not change tumor-associated macrophage (TAM) infiltration in tumors. Blockade of CXCR4 has differential effects on myeloid BMDC subsets: AMD3100 significantly reduces Gr-1$^{+}$ myeloid BMDC infiltration but does not change F4/80$^{+}$ TAM infiltration during early tumor growth in the TRAMP-C1 model in 8-wk-old mice.

Finally, to confirm the specific role of CXCR4 in Gr-1+ BMDC recruitment during early tumor growth, the infiltration of Gr-1+ BMDCs was evaluated in small (4-mm) tumors growing after AMD3100 treatment in a preventive setting. CXCR4 blockade significantly decreased the number of Gr-1+ BMDCs but not TAMs (FIG. 8). Thus, a substantial reduction in primary tumor growth and metastasis in these models required the combination of CXCR4 inhibition with AMD3100 with inhibition of VEGFR1-TK activity in BMDCs to reduce Gr-1+ myeloid BMDC as well as TAM infiltration and to inhibit angiogenesis.

CXCR4 and VEGFR1 Independently Mediate Gr-1+ BMDC and TAM Infiltration Via p38 Activation.

Figure 5A:
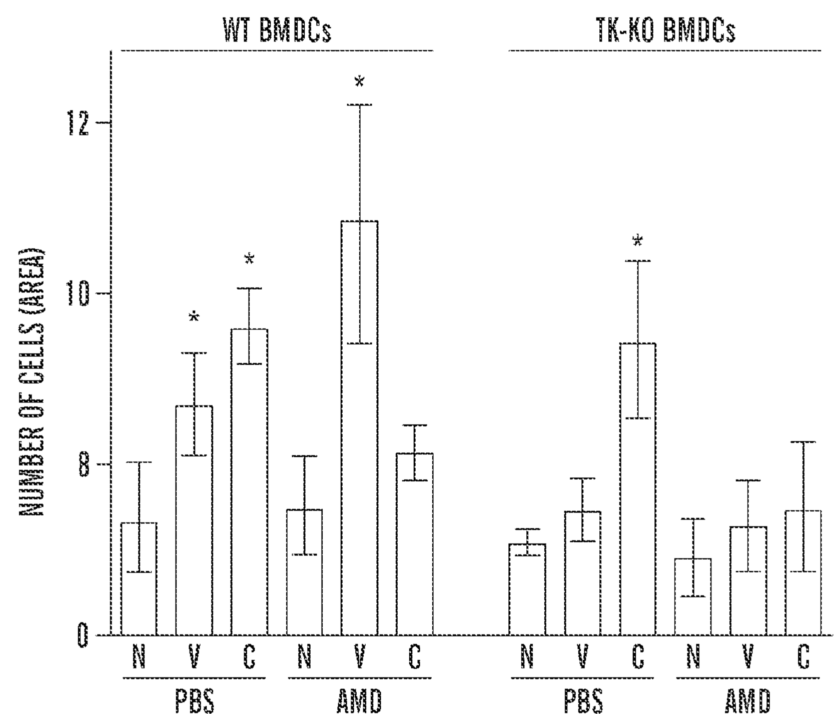
FIGS. 5A-5F demonstrate that blocking CXCR4 and/or VEGFR1-TK activity significantly inhibits BMDC migration via inhibition of P38 MAPK activity.

To reveal the mechanism of action of VEGFR1 and CXCR4 in myeloid BMDCs, bone marrow cells were harvested from C57BL/6 and VEGFR1 TK−/− mice and purified mononuclear myeloid BMDCs using magnetic separation for CD11b+ cells. The migration of myeloid BMDCs in response to recombinant (r)VEGF (100 ng/mL) and rCXCL12 (100 ng/mL) was measured in a transwell assay with or without blockade of CXCR4 using 1 μg/mL of AMD3100. rVEGF and rCXCL12 significantly increased WT-myeloid BMDC migration, and the effect was reversed when using VEGFR1 TK−/− myeloid BMDCs or AMD3100, respectively (FIG. 5A).

Figure 5B:
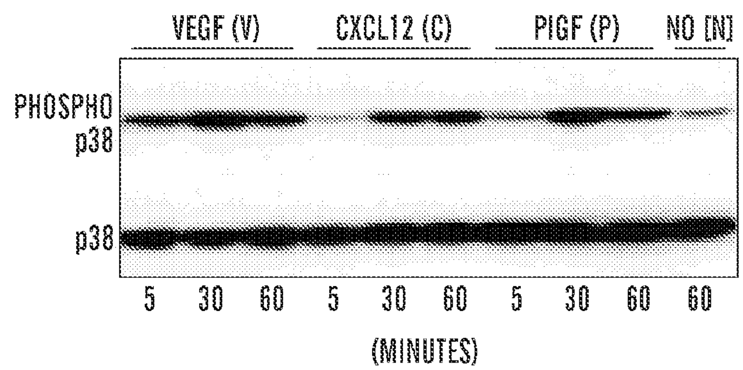
Figure 5C:
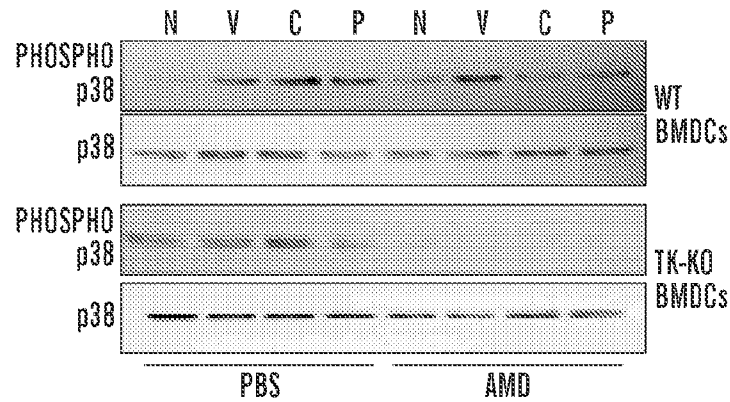
Figure 5D:
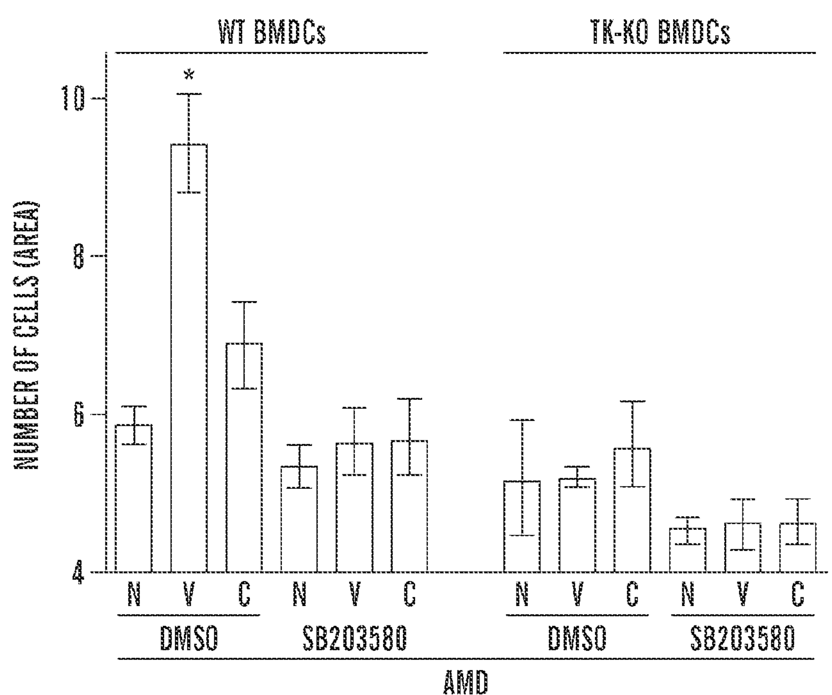

Next, phosphorylated p38 MAPK—a key factor in cell migration—was measured in myeloid BMDCs by Western blotting. rVEGF, rPlGF, and rCXCL12 rapidly increased p38 MAPK phosphorylation in myeloid BMDCs, with a peak level of activation after 30 min (FIG. 5B). Blockade of VEGFR1 TK (using VEGFR1 TK−/− myeloid BMDCs) or CXCR4 (using AMD3100) selectively reversed the p38 MAPK phosphorylation induced in myeloid BMDC by rVEGF/rPlGF or by rCXCL12, respectively (FIG. 5C). Blockade of p38 MAPK using SB203580 (1 μM) significantly reduced the migration of myeloid BMDCs, irrespective of the chemotactic stimulus (FIG. 5D).

Figure 5E:
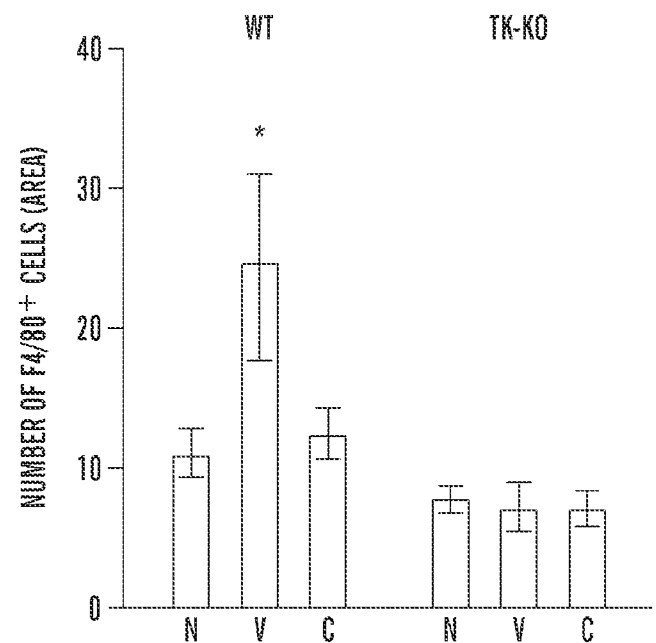
Figure 5F:
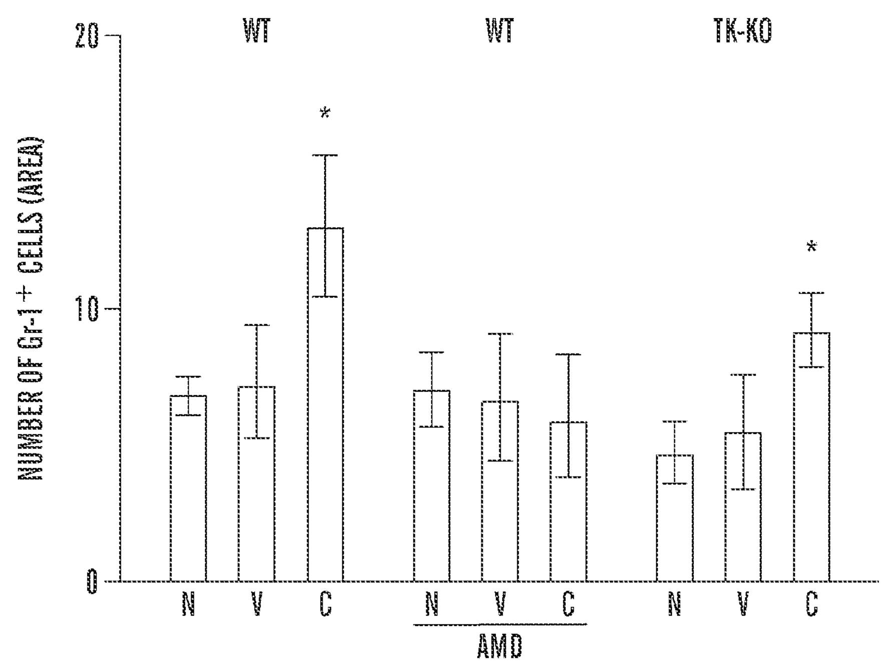

To establish if CXCL12 and VEGF promote the migration of specific myeloid BMDC populations, Gr-1+ and F4/80+ BMDCs were separated and their migration in vitro was evaluated. As expected, rVEGF increased the migration of F4/80+ BMDCs, and this effect was not seen when using VEGFR1 TK−/−F4/80+ BMDCs (FIG. 5E). In contrast, rCXCL12 did not affect the migration of F4/80+ BMDCs, but significantly increased the migration of Gr-1+ BMDCs (FIGS. 5E and 5F). The effect of rCXCL12 was reversed by AMD3100, but not by the use of VEGFR1 TK−/−Gr-1+ BMDCs (FIG. 5F).

Discussion

CXCR4 is a receptor specific for CXCL12 (also known as stromal-derived factor 1α) (11). Knockout of CXCR4 or CXCL12 is lethal due to the pleiotropic activity of this pathway, which is critical for hematopoietic, neural, vascular, and craniofacial organogenesis (12, 13). CXCR4 is constitutively expressed or induced by hypoxia in cancer cells and may mediate their migration and metastasis (14). However, CXCR4 is also a marker of myeloid BMDCs and is critical for BMDC retention in the bone marrow as well as for circulating BMDC infiltration in tissues (15-17). In brain tumors, hypoxia-inducible factor 1α (HIF-1α) activation—which can induce local expression of VEGF, PlGF, VEGFR1, and CXCL12—was shown to enhance the recruitment of multiple BMDC populations via the CXCL12/CXCR4 pathway (17). However, the effects of CXCR4 activity on angiogenesis may be independent of the VEGF pathway (18, 19). For example, in mice with brain tumors, treatment with a pan-VEGFR-TK inhibitor led to an increase in circulating CXCR4+ BMDCs and myeloid BMDC infiltration in the tumors growing in the face of treatment (20). It was desired to elucidate the interplay between CXCR4 and VEGFR1 activity specifically in myeloid BMDC subsets and to determine its impact on tumor angiogenesis, growth, and metastasis in two highly metastatic tumor models.

Recent reports indicate that VEGF pathway inhibition may not prevent metastasis formation on the basis of studies of anti-VEGF agents in experimental models in mice as well as trials in cancer patients treated in neoadjuvant or adjuvant settings (9, 21-24). Moreover, although blockade of VEGFR1 activity decreases the number of TAMs in certain tumors, it does not completely suppress myeloid BMDC infiltration in growing primary tumors or lung metastases (9, 25, 26). This may be due, at least in part, without wishing to be bound or limited by theory, to the inability of VEGF/VEGFR1 inhibition to prevent Gr-1+ myeloid cell infiltration into tumors (9, 10).

The hypothesis that CXCR4 activation leads to myeloid BMDC recruitment in the face of VEGFR1 inhibition in BMDCs was examined. To gain definitive genetic evidence that CXCR4 activity in BMDCs is required for VEGFR1-TK-independent BMDC recruitment in tumors and facilitation of tumor growth, an established animal model for conditional CXCR4 deficiency with and without VEGFR1-TK deletion was utilized. Using TRAMP-C1 prostate carcinoma and E0771 mammary carcinoma models in C57BL/6 mice (33, 34), it is demonstrated herein that CXCR4 activity in BMDC specifically mediates the tumor infiltration of Gr-1+ BMDCs during early tumor growth and metastasis formation. Moreover, it is shown herein that CXCR4-driven Gr-1+ BMDC infiltration is independent of the VEGFR1-TK activity blockade, which primarily mediates TAM infiltration in established tumors, and their interplay modulates primary tumor growth and angiogenesis. Although CXCR4 inhibition had a minor effect on primary tumor growth, it significantly reduced metastasis.

The effect of CXCR4 versus VEGFR1 activity was further dissected using a pharmacologic blockade of CXCR4 with AMD3100 alone versus VEGFR1-TK genetic inhibition. As in the genetic model, the effect of CXCR4 inhibition was specific reduction in Gr-1+ BMDC infiltration in the primary tumor, but the effects on tumor growth and metastasis were tumor-dependent. CXCR4 inhibition alone delayed primary tumor growth and metastasis in the TRAMP-C1 model. In the E0771 model, a significant delay in primary tumor growth and metastasis was seen only after concomitant inhibition of CXCR4 and VEGFR1 in BMDCs.

Collectively, these data indicate that a CXCR4 blockade can reduce the infiltration of Gr-1+ BMDCs—independently of VEGFR1-TK activity in BMDCs—and delay early tumor growth and metastasis formation. This mechanism may potentially explain, without wishing to be bound or limited by theory, the association between increased CXCL12 concentration and poor outcome in cancer patients after anti-VEGF therapy (35).

In vitro studies revealed that VEGF and CXCL12 independently affect the migration of myeloid BMDC subsets. This effect was pathway-specific as (i) the CXCR4 blockade did not affect myeloid BMDC migration in response to rVEGF, and (ii) VEGFR1TK−/− myeloid BMDCs show increased migration in response to rCXCL12.

To identify the mechanisms responsible for this "escape" from VEGFR1 inhibition in myeloid BMDCs, the role of p38 MAPK in cell migration was evaluated. As demonstrated herein, p38 MAPK phosphorylation is a common mediator of myeloid BMDC migration—downstream of both CXCR4 in Gr-1+ BMDCs and VEGFR1-TK in F4/80+TAMs.

Figure 6:
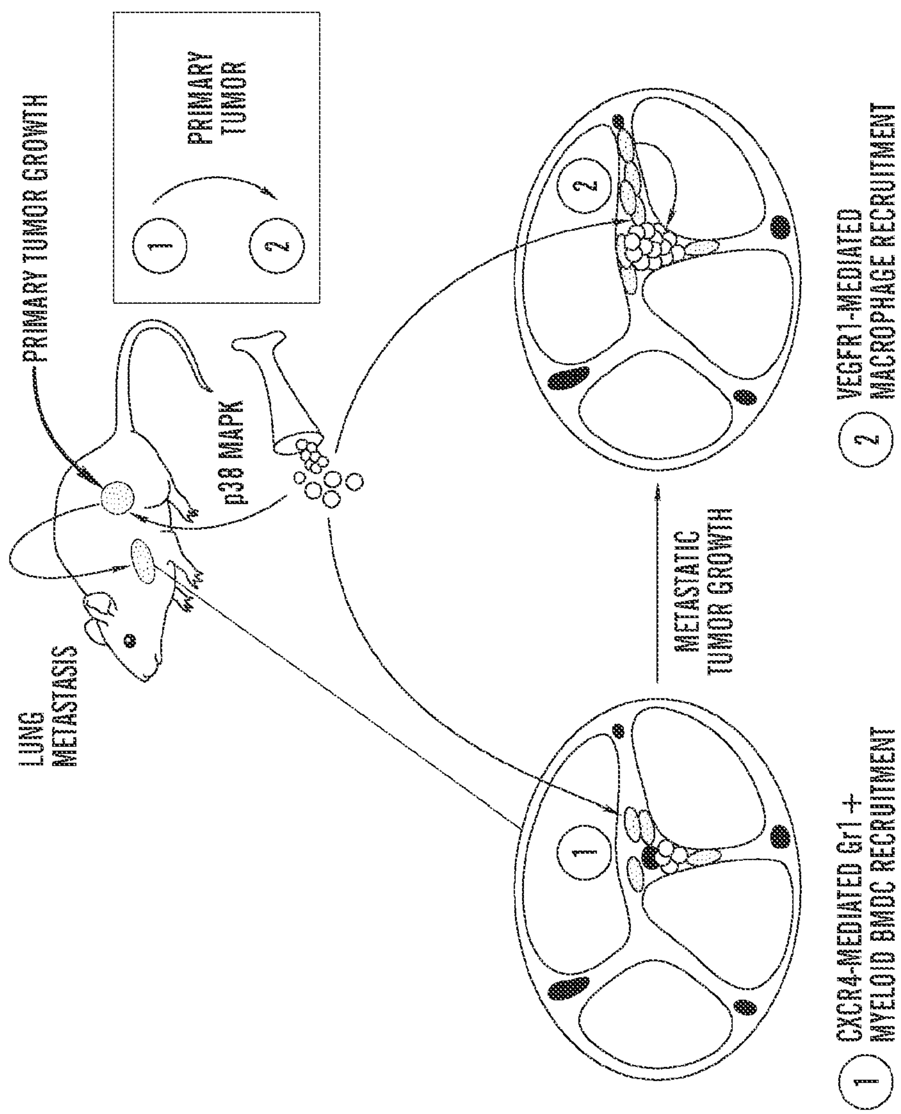
FIG. 6 depicts a model of hematopoietic myeloid (CD11b$^{+}$) BMDC contribution to tumors during metastasis. On the basis of our data, we propose a model, without wishing to be bound or limited by theory, in which the recruitment of tumor-promoting myeloid BMDCs is sequential. First, small tumors primarily recruit Gr-1$^{+}$ myeloid BMDCs for their early growth using CXCL12/CXCR4 pathway to activate p38 MAPK in these cells. Next, established tumors recruit primarily macrophages by VEGFR1-TK and p38 MAPK activation in these BMDCs. This cycle can repeat during micrometastasis growth into a metastatic nodule: Initially the micrometastases can recruit Gr1$^{+}$ myeloid BMDCs and, when established in a metastatic nodule, can recruit macrophages that are resident in the adjacent lung or from blood circulation.

In conclusion, inhibition of CXCR4 in myeloid BMDCs can suppress tumor growth, angiogenesis, and metastasis. This relies in a significant manner on selectively decreasing Gr-1+ BMDC infiltration in primary tumors. Activation of CXCR4 is particularly critical for Gr-1+ BMDC infiltration during tumor growth, whereas VEGFR1-TK activity selectively modulates TAM in filtration in established tumors. The results described herein indicate that inhibition of both CXCR4 and VEGFR1-TK activity can be required for a meaningful decrease in tumor angiogenesis, myeloid BMDC infiltration, and metastasis (FIG. 6). In addition, it is demonstrated herein that p38 MAPK activation is a critical mediator downstream of both CXCR4 and VEGFR1-TK activation in BMDCs, which supports the development of p38 MAPK inhibitors for cancer. These results also have important implications for therapeutics that are widely used in the clinic and indicate, as described herein, that combining the CXCR4 blockade with drugs that inhibit VEGFR1-TK activity can be a valid strategy to induce greater tumor growth delay and prevent or inhibit metastasis.

TABLE 1

Association between CXCL12 and outcome of anti-VEGF therapy with antibodies or receptor tyrosine kinase inhibitors

| Cancer type (anti-VEGF agent) | Locally advanced rectal cancer (anti-VEGF antibody bevacizumab) | Recurrent GBM (VEGFR TKI cediranib) | Advanced HCC (VEGF receptor TKI sunitinib) | Advanced sarcoma (VEGFR TKI sorafenib) |
|---|---|---|---|---|
| CXCL12 | Expression of CXCL12 and its receptor CXCR4 is increased in cancer cells by VEGF blockade with bevacizumab ($P < 0.05$) (1) | Anti-VEGFR therapy increases circulating CXCL12 ($P < 0.001$) (2, 3) | Anti-VEGFR therapy increases circulating CXCL12 ($P < 0.001$) (4) | Anti-VEGFR therapy increases circulating CXCL12 ($P < 0.01$) (5) |
| | Higher levels of circulating CXCL12 during anti-VEGF treatment is associated with higher rates of distant metastasis at 3 y ($P < 0.05$) (1) | Circulating CXCL12 increase is associated with rapid recurrence after VEGFR blockade ($P < 0.01$) (2, 3) | Circulating CXCL12 increase is associated with lower survival after anti-VEGFR ($P < 0.01$) (4) | Circulating CXCL12 increase is associated with poor response after anti-VEGFR treatment ($P < 0.5$) (5) |

VEGFR, VEGF receptor; TKI, tyrosine kinase inhibitor; GBM, glioblastoma; HCC, hepatocellular carcinoma

REFERENCES FOR EXAMPLE 2 AND THE SPECIFICATION

1. Talmadge J E, Fidler I J (2010) AACR centennial series. The biology of cancer metastasis: Historical perspective. Cancer Res 70:5649-5669
2. McAllister S S, Weinberg R A (2010) Tumor-host interactions: A far-reaching relationship. Clin Oncol 28:4022-4028.
3. Mantovani A, Allavena P, Sica A, Balkwill F (2008) Cancer-related inflammation. Nature 454:436-444.
4. De Palma M, et al. (2005) Tie2 identifies a hematopoietic lineage of proangiogenic monocytes required for tumor vessel formation and a mesenchymal population of pericyte progenitors. Cancer Cell 8:211-226.
5. Murdoch C, Muthana M, Coffelt S B, Lewis C E (2008) The role of myeloid cells in the promotion of tumour angiogenesis. Nat Rev Cancer 8:618-631.
6. Yan L, Borregaard N, Kjeldsen L, Moses M A (2001) The high molecular weight urinary matrix metalloproteinase (MMP) activity is a complex of gelatinase B/MMP-9 and neutrophil gelatinase-associated lipocalin (NGAL). Modulation of MMP-9 activity by NGAL. J Biol Chem 276:37258-37265.
7. Fischer C, Mazzone M, Jonckx B, Carmeliet P (2008) FLT1 and its ligands VEGFB and PlGF: Drug targets for anti-angiogenic therapy? Nat Rev Cancer 8:942-956.
8. Tchaikovski V, Fellbrich G, Waltenberger J (2008) The molecular basis of VEGFR-1 signal transduction pathways in primary human monocytes. Arterioscler Thromb Vasc Biol 28:322-328.
9. Dawson M R, Duda D G, Chae S S, Fukumura D, Jain R K (2009) VEGFR1 activity modulates myeloid cell infiltration in growing lung metastases but is not required for spontaneous metastasis formation. PLoS ONE 4:e6525.
10. Shojaei F, et al. (2007) Tumor refractoriness to anti-VEGF treatment is mediated by CD11b+Gr1+ myeloid cells. Nat Biotechnol 25:911-920.
11. Teicher B A, Fricker S P (2010) CXCL12 (SDF-1)/CXCR4 pathway in cancer. Clin Cancer Res 16:2927-2931.
12. Nagasawa T, et al. (1996) Defects of B-cell lymphopoiesis and bone-marrow myelopoiesis in mice lacking the CXC chemokine PBSF/SDF-1. Nature 382:635-638.
13. Tachibana K, et al. (1998) The chemokine receptor CXCR4 is essential for vascularization of the gastrointestinal tract. Nature 393:591-594.
14. Staller P, et al. (2003) Chemokine receptor CXCR4 downregulated by von Hippel-Lindau tumour suppressor pVHL. Nature 425:307-311.
15. Grunewald M, et al. (2006) VEGF-induced adult neovascularization: Recruitment, retention, and role of accessory cells. Cell 124:175-189.
16. Jin D K, et al. (2006) Cytokine-mediated deployment of SDF-1 induces revascularization through recruitment of CXCR4+ hemangiocytes. Nat Med 12:557-567.
17. Du R, et al. (2008) HIF1alpha induces the recruitment of bone marrow-derived vascular modulatory cells to regulate tumor angiogenesis and invasion. Cancer Cell 13:206-220.
18. Kryczek I, et al. (2005) CXCL12 and vascular endothelial growth factor synergistically induce neoangiogenesis in human ovarian cancers. Cancer Res 65:465-472.
19. Kryczek I, Wei S, Keller E, Liu R, Zou W (2007) Stroma-derived factor (SDF-1/CXCL12) and human tumor pathogenesis. Am J Physiol Cell Physiol 292:C987-C995.
20. Kamoun W S, et al. (2009) Edema control by cediranib, a vascular endothelial growth factor receptor-targeted kinase inhibitor, prolongs survival despite persistent brain tumor growth in mice. J Clin Oncol 27:2542-2552.
21. Padera T P, et al. (2008) Differential response of primary tumor versus lymphatic metastasis to VEGFR-2 and VEGFR-3 kinase inhibitors cediranib and vandetanib. Mol Cancer Ther 7:2272-2279.
22. Dawson M R, Duda D G, Fukumura D, Jain R K (2009) VEGFR1-activity-independent metastasis formation. Nature 461:E4-E5; discussion E5.
23. Allegra C J, et al. (2010) Phase III trial assessing bevacizumab in stages II and III carcinoma of the colon: Results of NSABP protocol C-08. J Clin Oncol, 10.1200/JCO.2010.30.0855.
24. Willett C G, et al. (2010) A safety and survival analysis of neoadjuvant bevacizumab with standard chemoradiation in a phase I/II study compared with standard chemoradiation in locally advanced rectal cancer. Oncologist 15:845-851.
25. Casanovas O, Hicklin D J, Bergers G, Hanahan D (2005) Drug resistance by evasion of antiangiogenic targeting of VEGF signaling in late-stage pancreatic islet tumors. Cancer Cell 8:299-309.
26. Kerber M, et al. (2008) Flt-1 signaling in macrophages promotes glioma growth in vivo. Cancer Res 68:7342-7351.
27. Batchelor T T, et al. (2007) AZD2171, a pan-VEGF receptor tyrosine kinase inhibitor, normalizes tumor vasculature and alleviates edema in glioblastoma patients. Cancer Cell 11:83-95.

28. Ebos J M, Lee C R, Christensen J G, Mutsaers A J, Kerbel R S (2007) Multiple circulating proangiogenic factors induced by sunitinib malate are tumor-independent and correlate with antitumor efficacy. Proc Natl Acad Sci USA 104:17069-17074.

29. Willett C G, et al. (2009) Efficacy, safety, and biomarkers of neoadjuvant bevacizumab, radiation therapy, and fluorouracil in rectal cancer: A multidisciplinary phase II study. J Clin Oncol 27:3020-3026.

30. Zhu A X, et al. (2009) Efficacy, safety, and potential biomarkers of sunitinib monotherapy in advanced hepatocellular carcinoma: A phase II study. J Clin Oncol 27:3027-3035.

31. Xu L, et al. (2009) Direct evidence that bevacizumab, an anti-VEGF antibody, upregulates SDF1alpha, CXCR4, CXCL6, and neuropilin 1 in tumors from patients with rectal cancer. Cancer Res 69:7905-7910.

32. Raut C P, et al. (2010) Measurement of interstitial fluid pressure (IFP) and circulating biomarkers in soft tissue sarcoma (STS): An exploratory phase II clinical and correlative study of sorafenib (SOR) in patients with refractory STS (NCI Protocol 6948). J Clin Oncol 28:(Suppl; abstr 10091).

33. Somers K D, et al. (2003) Orthotopic treatment model of prostate cancer and metastasis in the immunocompetent mouse: Efficacy of flt3 ligand immunotherapy. Int J Cancer 107:773-780.

34. Ewens A, Mihich E, Ehrke M J (2005) Distant metastasis from subcutaneously grown E0771 medullary breast adenocarcinoma. Anticancer Res 25(6B):3905-3915.

35. Jain R K, et al. (2009) Biomarkers of response and resistance to antiangiogenic therapy. Nat Rev Clin Oncol 6:327-338.

36. Hiratsuka S, Minowa O, Kuno J, Noda T, Shibuya M (1998) Flt-1 lacking the tyrosine kinase domain is sufficient for normal development and angiogenesis in mice. Proc Natl Acad Sci USA 95:9349-9354.

37. Sugiyama T, Kohara H, Noda M, Nagasawa T (2006) Maintenance of the hematopoietic stem cell pool by CXCL12-CXCR4 chemokine signaling in bone marrow stromal cell niches. Immunity 25:977-988.

38. Xu L, et al. (2009) Direct evidence that bevacizumab, an anti-VEGF antibody, up-regulates SDF1alpha, CXCR4, CXCL6, and neuropilin 1 in tumors from patients with rectal cancer. Cancer Res 69:7905-7910.

39. Batchelor T T, et al. (2010) Phase II study of cediranib, an oral pan-VEGF receptor tyrosine kinase inhibitor, in patients with recurrent glioblastoma. J Clin Oncol 28:2817-2823.

40. Batchelor T T, et al. (2007) AZD2171, a pan-VEGF receptor tyrosine kinase inhibitor, normalizes tumor vasculature and alleviates edema in glioblastoma patients. Cancer Cell 11:83-95.

41. Zhu A X, et al. (2009) Efficacy, safety, and potential biomarkers of sunitinib monotherapy in advanced hepatocellular carcinoma: A phase II study. J Clin Oncol 27:3027-3035.

42. Raut C P, et al. (2010) Measurement of interstitial fluid pressure (IFP) and circulating biomarkers in soft tissue sarcoma (STS): An exploratory phase II clinical and correlative study of sorafenib (SOR) in patients with refractory STS (NCI Protocol 6948). J Clin Oncol 28 (Suppl; abstr 10091).

We claim:

1. A method of treating a cancer tumor in a subject in need thereof, comprising:

administering an anti-tumor therapy to the subject; and administering a therapeutically effective amount of a CXCR4 inhibitor to the subject within 5 days of administering the anti-tumor therapy;

measuring the level of CXCL12 expression in the subject;

comparing the level of CXCL12 expression in the subject to a reference level;

and administering the CXCR4 inhibitor to the subject until CXCL12 expression is within 10% of the reference level.

2. The method of claim 1, wherein the treatment comprises treating metastasis of a cancer tumor.

3. The method of claim 1, wherein the CXCR4 inhibitor is selected from the group consisting of small organic or inorganic molecules; polysaccharides; peptides; polypeptides; proteins; antibodies; peptide analogs and derivatives; peptidomimetics; nucleic acids; nucleic acid analogs and derivatives; and any combinations thereof.

4. The method of claim 3, wherein the CXCR4 inhibitor is selected from the group consisting of 1,1'-[1,4-phenylene-bis(methylene)]-bis-1,4,8,11-tetraazacyclotetradecane (AMD-3100); NOXA12; CTCE-9908; ALX40-4C; T22; T140; Met-SDF1 beta (Met-SDF-1β); T134; AMD-3465; N'-(1-Hbenzimidazol-2-yl methyl)-N1-(5,6,7,8-tetrahydroquinoline8-yl)-butane 1,4-diamine; CTCF-0214; CTCF-9908; CP-1221; 4F-benzoylTN24003; KRH-1120; KRH-1636; KRH-2731; polyphemusin analogue; ALX40-4C; T-140; T-140 analogs and derivatives; TN14003; TC14012; TE14011; and any combinations thereof.

5. The method of claim 1, wherein the anti-tumor therapy is selected from the group consisting of radiation therapy, chemotherapy, antiangiogenic therapy, and any combinations thereof.

6. The method of claim 5, wherein the anti-tumor therapy increases the expression of CXCL12 by at least 10%.

7. The method of claim 1, wherein the antitumor therapy comprises administering a VEGF inhibitor.

8. The method of claim 7, wherein the VEGF inhibitor is selected from the group consisting of: ABT-869: AEE-788; AG-13736; AG-028262; Angiostatin; bevacizumab; AVE-8062; AZD-2171; sorafenib; BMS-387032; CEP-7055; CHIR-258; GFKI; CP-547632; CP-564959; E-7080; 786034; GW-654652; IMC-1 C11; KRN-951; PKC-412; PTK-787; SU11248; SU-5416; SU-6668; AVE-0005; thalidomide; XL-647; XL-999; ZD-6474; ZK-304709; Pazopanib; CDP791; Enzastaurin; BIBF 1120; BAY 573952; BAY 734506; XL 184; IMC-1121B; CEP 701; SU 014813; SU 10944; SU 12662; OSI-930; BMS 582664; ZD-6126; Imatinib; STI-571; CGP-57148; RAD-001; BMS-354825; Volociximab; CCI-779; 17-AAG; DMXAA; CI-1040; CI-1033; (5-[5-fluoro-2-oxo-1,2-dihydroindol(3Z)-ylidenemethyl]-2,4-dimethyl-1H-pyrrole-3-carboxylic acid [2-diethylaminoethyl]amide); 4TBPPAPC; AMG 706; and PTK/ZK.

9. The method of claim 1, wherein the anti-tumor therapy comprises administering a p38 MAPK inhibitor.

10. The method of claim 9, wherein the p38 MAPK inhibitor is selected from the group consisting of antisense p38 MAPK nucleic acids and fragments thereof, antibodies that bind p38 MAPK and fragments thereof, EO-1428, SB239063, SB281832, VX-702, VX-745, ZM336372, RPR 200765A, N-(3-tert-butyl-1-methyl-5-pyrazolyl)N'-(4-(4-pyridinylmethyl)phenyl)urea, SB203580, SB202190, PD169316, fr-167653, trans-1-(4-hydroxycyclohexyl)-4-(4-fluorophenyl)-5-(2 methoxypyridimidin-4-yl)imidazole, 2-(4-Chlorophenyl)-4-)4-fluorophenyl)-5-pyridin-4-yl-1,2-dihydropyrazol-3-one, and any combinations thereof.

11. The method of claim 1, wherein the cancer is selected from the group consisting of basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

12. The method of claim 1, wherein the CXCR4 inhibitor administration is systemic administration.

13. The method of claim 1, wherein the CXCR4 inhibitor administration is by injection, infusion, instillation, inhalation, or ingestion.

14. The method of claim 13, wherein said injection is intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, or intrasternal injection.

15. The method of claim 1, wherein the therapeutically effective amount of the CXCR4 inhibitor is 1 μg/kg to 150 mg/kg of bodyweight.

16. The method of claim 1, wherein the CXCR4 inhibitor is administered for at least 1 day.

17. The method of claim 16, wherein the CXCR4 inhibitor is administered for at least one week.

18. The method of claim 1, wherein the subject is a human.

* * * * *

SEQUENCE LISTING

```
<160> NUMBER OF SEQ ID NOS: 10

<210> SEQ ID NO 1
<211> LENGTH: 1912
<212> TYPE: DNA
<213> ORGANISM: Homo sapiens

<400> SEQUENCE: 1

tttttttct tccctctagt gggcggggca gaggagttag ccaagatgtg actttgaaac     60

cctcagcgtc tcagtgccct tttgttctaa acaaagaatt ttgtaattgg ttctaccaaa    120

gaaggatata atgaagtcac tatgggaaaa gatggggagg agagttgtag gattctacat    180

taattctctt gtgcccttag cccactactt cagaatttcc tgaagaaagc aagcctgaat    240

tggtttttta aattgcttta aaaatttttt ttaactgggt taatgcttgc tgaattggaa    300

gtgaatgtcc attcctttgc ctcttttgca gatatacact tcagataact acaccgagga    360

aatgggctca ggggactatg actccatgaa ggaaccctgt ttccgtgaag aaaatgctaa    420

tttcaataaa atcttcctgc ccaccatcta ctccatcatc ttcttaactg gcattgtggg    480

caatggattg gtcatcctgg tcatgggtta ccagaagaaa ctgagaagca tgacggacaa    540

gtacaggctg cacctgtcag tggccgacct cctctttgtc atcacgcttc ccttctgggc    600

agttgatgcc gtggcaaact ggtactttgg gaacttccta tgcaaggcag tccatgtcat    660

ctacacagtc aacctctaca gcagtgtcct catcctggcc ttcatcagtc tggaccgcta    720

cctggccatc gtccacgcca ccaacagtca gaggccaagg aagctgttgg ctgaaaaggt    780

ggtctatgtt ggcgtctgga tccctgccct cctgctgact attcccgact tcatctttgc    840
```

```
caacgtcagt gaggcagatg acagatatat ctgtgaccgc ttctacccca atgacttgtg    900
ggtggttgtg ttccagtttc agcacatcat ggttggcctt atcctgcctg gtattgtcat    960
cctgtcctgc tattgcatta tcatctccaa gctgtcacac tccaagggcc accagaagcg   1020
caaggccctc aagaccacag tcatcctcat cctggctttc ttcgcctgtt ggctgcctta   1080
ctacattggg atcagcatcg actccttcat cctcctggaa atcatcaagc aagggtgtga   1140
gtttgagaac actgtgcaca agtggatttc catcaccgag gccctagctt tcttccactg   1200
ttgtctgaac ccatcctct atgctttcct tggagccaaa tttaaaacct ctgcccagca   1260
cgcactcacc tctgtgagca gagggtccag cctcaagatc ctctccaaag gaaagcgagg   1320
tggacattca tctgtttcca ctgagtctga gtcttcaagt tttcactcca gctaacacag   1380
atgtaaaaga cttttttta tacgataaat aacttttttt taagttacac atttttcaga   1440
tataaaagac tgaccaatat tgtacagttt ttattgcttg ttggattttt gtcttgtgtt   1500
tctttagttt ttgtgaagtt taattgactt atttatataa attttttttg tttcatattg   1560
atgtgtgtct aggcaggacc tgtggccaag ttcttagttg ctgtatgtct cgtggtagga   1620
ctgtagaaaa gggaactgaa cattccagag cgtgtagtga atcacgtaaa gctagaaatg   1680
atccccagct gtttatgcat agataatctc tccattcccg tggaacgttt ttcctgttct   1740
taagacgtga ttttgctgta gaagatggca cttataacca aagcccaaag tggtatagaa   1800
atgctggttt ttcagttttc aggagtgggt tgatttcagc acctacagtg tacagtcttg   1860
tattaagttg ttaataaaag tacatgttaa acttaaaaaa aaaaaaaaaa aa           1912
```

```
<210> SEQ ID NO 2
<211> LENGTH: 1691
<212> TYPE: DNA
<213> ORGANISM: Homo sapiens

<400> SEQUENCE: 2

aacttcagtt tgttggctgc ggcagcaggt agcaaagtga cgccgagggc ctgagtgctc     60
cagtagccac cgcatctgga gaaccagcgg ttaccatgga ggggatcagt atatacactt    120
cagataacta caccgaggaa atgggctcag gggactatga ctccatgaag gaaccctgtt    180
tccgtgaaga aaatgctaat ttcaataaaa tcttcctgcc caccatctac tccatcatct    240
tcttaactgg cattgtgggc aatggattgg tcatcctggt catgggttac cagaagaaac    300
tgagaagcat gacggacaag tacaggctgc acctgtcagt ggccgacctc ctctttgtca    360
tcacgcttcc cttctgggca gttgatgccg tggcaaactg gtactttggg aacttcctat    420
gcaaggcagt ccatgtcatc tacacagtca acctctacag cagtgtcctc atcctggcct    480
tcatcagtct ggaccgctac ctggccatcg tccacgccac caacagtcag aggccaagga    540
agctgttggc tgaaaaggtg gtctatgttg gcgtctggat ccctgccctc ctgctgacta    600
ttcccgactt catctttgcc aacgtcagtg aggcagatga cagatatatc tgtgaccgct    660
tctaccccaa tgacttgtgg gtggttgtgt tccagtttca gcacatcatg gttggcctta    720
tcctgcctgg tattgtcatc ctgtcctgct attgcattat catctccaag ctgtcacact    780
ccaagggcca ccagaagcgc aaggccctca agaccacagt catcctcatc ctggctttct    840
tcgcctgttg gctgccttac tacattggga tcagcatcga ctccttcatc ctcctggaaa    900
tcatcaagca agggtgtgag tttgagaaca ctgtgcacaa gtggatttcc atcaccgagg    960
ccctagcttt cttccactgt tgtctgaacc ccatcctcta tgctttcctt ggagccaaat   1020
ttaaaacctc tgcccagcac gcactcacct ctgtgagcag agggtccagc ctcaagatcc   1080
```

```
tctccaaagg aaagcgaggt ggacattcat ctgtttccac tgagtctgag tcttcaagtt   1140
ttcactccag ctaacacaga tgtaaaagac tttttttat acgataaata actttttttt    1200
aagttacaca tttttcagat ataaaagact gaccaatatt gtacagtttt tattgcttgt   1260
tggatttttg tcttgtgttt ctttagtttt tgtgaagttt aattgactta tttatataaa   1320
ttttttttgt ttcatattga tgtgtgtcta ggcaggacct gtggccaagt tcttagttgc   1380
tgtatgtctc gtggtaggac tgtagaaaag ggaactgaac attccagagc gtgtagtgaa   1440
tcacgtaaag ctagaaatga tccccagctg tttatgcata gataatctct ccattcccgt   1500
ggaacgtttt tcctgttctt aagacgtgat tttgctgtag aagatggcac ttataaccaa   1560
agcccaaagt ggtatagaaa tgctggtttt tcagttttca ggagtgggtt gatttcagca   1620
cctacagtgt acagtcttgt attaagttgt taataaaagt acatgttaaa cttaaaaaaa   1680
aaaaaaaaaa a                                                        1691
```

<210> SEQ ID NO 3
<211> LENGTH: 1940
<212> TYPE: DNA
<213> ORGANISM: Homo sapiens

<400> SEQUENCE: 3

```
gccgcacttt cactctccgt cagccgcatt gcccgctcgg cgtccggccc ccgacccgcg     60
ctcgtccgcc cgcccgcccg cccgcccgcg ccatgaacgc caaggtcgtg gtcgtgctgg    120
tcctcgtgct gaccgcgctc tgcctcagcg acgggaagcc cgtcagcctg agctacagat    180
gcccatgccg attcttcgaa agccatgttg ccagagccaa cgtcaagcat ctcaaaattc    240
tcaacactcc aaactgtgcc cttcagattg tagcccggct gaagaacaac aacagacaag    300
tgtgcattga cccgaagcta aagtggattc aggagtacct ggagaaagct ttaaacaagt    360
aagcacaaca gccaaaaagg actttccgct agacccactc gaggaaaact aaaaccttgt    420
gagagatgaa agggcaaaga cgtgggggag gggccttaa ccatgaggac caggtgtgtg     480
tgtggggtgg gcacattgat ctgggatcgg gcctgaggtt tgccagcatt tagaccctgc    540
atttatagca tacggtatga tattgcagct tatattcatc catgccctgt acctgtgcac    600
gttggaactt ttattactgg ggtttttcta agaaagaaat tgtattatca acagcatttt    660
caagcagtta gttccttcat gatcatcaca atcatcatca ttctcattct catttttaa     720
atcaacgagt acttcaagat ctgaatttgg cttgtttgga gcatctcctc tgctcccctg    780
gggagtctgg gcacagtcag gtggtggctt aacagggagc tggaaaaagt gtcctttctt    840
cagacactga ggctcccgca gcagcgcccc tcccaagagg aaggcctctg tggcactcag    900
ataccgactg gggctgggcg ccgccactgc cttcacctcc tctttcaacc tcagtgattg    960
gctctgtggg ctccatgtag aagccactat tactgggact gtgctcagag acccctctcc   1020
cagctattcc tactctctcc ccgactccga gagcatgctt aatcttgctt ctgcttctca   1080
tttctgtagc ctgatcagcg ccgcaccagc cgggaagagg gtgattgctg gggctcgtgc   1140
cctgcatccc tctcctccca gggcctgccc cacagctcgg gccctctgtg agatccgtct   1200
ttggcctcct ccagaatgga gctggccctc tcctggggat gtgtaatggt cccccctgctt  1260
acccgcaaaa gacaagtctt tacagaatca aatgcaattt taaatctgag agctcgcttt   1320
gagtgactgg gttttgtgat tgcctctgaa gcctatgtat gccatggagg cactaacaaa   1380
ctctgaggtt tccgaaatca gaagcgaaaa aatcagtgaa taaaccatca tcttgccact   1440
```

```
accccctcct gaagccacag cagggtttca ggttccaatc agaactgttg gcaaggtgac   1500

atttccatgc ataaatgcga tccacagaag gtcctggtgg tatttgtaac tttttgcaag   1560

gcattttttt atatatattt ttgtgcacat tttttttac gtttctttag aaaacaaatg   1620

tatttcaaaa tatatttata gtcgaacaat tcatatattt gaagtggagc catatgaatg   1680

tcagtagttt atacttctct attatctcaa actactggca atttgtaaag aaatatatat   1740

gatatataaa tgtgattgca gcttttcaat gttagccaca gtgtattttt tcacttgtac   1800

taaaattgta tcaaatgtga cattatatgc actagcaata aaatgctaat tgtttcatgg   1860

tataaacgtc ctactgtatg tgggaattta tttacctgaa ataaaattca ttagttgtta   1920

gtgatggagc ttaaaaaaaa                                                1940
```

<210> SEQ ID NO 4
<211> LENGTH: 3545
<212> TYPE: DNA
<213> ORGANISM: Homo sapiens

<400> SEQUENCE: 4

```
gccgcacttt cactctccgt cagccgcatt gcccgctcgg cgtccggccc ccgacccgcg     60

ctcgtccgcc cgcccgcccg cccgcccgcg ccatgaacgc caaggtcgtg gtcgtgctgg    120

tcctcgtgct gaccgcgctc tgcctcagcg acgggaagcc cgtcagcctg agctacagat    180

gcccatgccg attcttcgaa agccatgttg ccagagccaa cgtcaagcat ctcaaaattc    240

tcaacactcc aaactgtgcc cttcagattg tagcccggct gaagaacaac aacagacaag    300

tgtgcattga cccgaagcta aagtggattc aggagtacct ggagaaagct ttaaacaaga    360

ggttcaagat gtgagagggt cagacgcctg aggaaccctt acagtaggag cccagctctg    420

aaaccagtgt tagggaaggg cctgccacag cctcccctgc cagggcaggg ccccaggcat    480

tgccaagggc tttgttttgc acactttgcc atattttcac catttgatta tgtagcaaaa    540

tacatgacat ttatttttca tttagtttga ttattcagtg tcactggcga cacgtagcag    600

cttagactaa ggccattatt gtacttgcct tattagagtg tctttccacg gagccactcc    660

tctgactcag ggctcctggg ttttgtattc tctgagctgt gcaggtgggg agactgggct    720

gagggagcct ggccccatgg tcagccctag ggtggagagc caccaagagg gacgcctggg    780

ggtgccagga ccagtcaacc tgggcaaagc ctagtgaagg cttctctctg tgggatggga    840

tggtggaggg ccacatggga ggctcacccc cttctccatc cacatgggag ccgggtctgc    900

ctcttctggg agggcagcag ggctaccctg agctgaggca gcagtgtgag gccagggcag    960

agtgagaccc agccctcatc ccgagcacct ccacatcctc cacgttctgc tcatcattct   1020

ctgtctcatc catcatcatg tgtgtccacg actgtctcca tggccccgca aaaggactct   1080

caggaccaaa gctttcatgt aaactgtgca ccaagcagga aatgaaaatg tcttgtgtta   1140

cctgaaaaca ctgtgcacat ctgtgtcttg tttggaatat tgtccattgt ccaatcctat   1200

gtttttgttc aaagccagcg tcctcctctg tgaccaatgt cttgatgcat gcactgttcc   1260

ccctgtgcag ccgctgagcg aggagatgct ccttgggccc tttgagtgca gtcctgatca   1320

gagccgtggt cctttggggt gaactacctt ggttccccca ctgatcacaa aaacatggtg   1380

ggtccatggg cagagcccaa gggaattcgg tgtgcaccag ggttgacccc agaggattgc   1440

tgccccatca gtgctccctc acatgtcagt accttcaaac tagggccaag cccagcactg   1500

cttgaggaaa acaagcattc acaacttgtt tttggttttt aaaacccagt ccacaaaata   1560

accaatcctg gacatgaaga ttctttccca attcacatct aacctcatct tcttcaccat   1620
```

```
ttggcaatgc catcatctcc tgccttcctc ctgggccctc tctgctctgc gtgtcacctg   1680
tgcttcgggc ccttcccaca ggacatttct ctaagagaac aatgtgctat gtgaagagta   1740
agtcaacctg cctgacattt ggagtgttcc ccttccactg agggcagtcg atagagctgt   1800
attaagccac ttaaaatgtt cacttttgac aaaggcaagc acttgtgggt ttttgttttg   1860
tttttcattc agtcttacga atacttttgc cctttgatta aagactccag ttaaaaaaaa   1920
ttttaatgaa gaaagtggaa aacaaggaag tcaaagcaag gaaactatgt aacatgtagg   1980
aagtaggaag taaattatag tgatgtaatc ttgaattgta actgttcttg aatttaataa   2040
tctgtagggt aattagtaac atgtgttaag tattttcata agtatttcaa attggagctt   2100
catggcagaa ggcaaaccca tcaacaaaaa ttgtccctta aacaaaaatt aaaatcctca   2160
atccagctat gttatattga aaaaatagag cctgagggat ctttactagt tataaagata   2220
cagaactctt tcaaaacctt ttgaaattaa cctctcacta taccagtata attgagtttt   2280
cagtggggca gtcattatcc aggtaatcca agatatttta aaatctgtca cgtagaactt   2340
ggatgtacct gcccccaatc catgaaccaa gaccattgaa ttcttggttg aggaaacaaa   2400
catgacccta aatcttgact acagtcagga aaggaatcat ttctatttct cctccatggg   2460
agaaaataga taagagtaga aactgcaggg aaaattattt gcataacaat tcctctacta   2520
acaatcagct ccttcctgga gactgcccag ctaaagcaat atgcatttaa atacagtctt   2580
ccatttgcaa gggaaaagtc tcttgtaatc cgaatctctt tttgctttcg aactgctagt   2640
caagtgcgtc cacgagctgt ttactaggga tccctcatct gtccctccgg gacctggtgc   2700
tgcctctacc tgacactccc ttgggctccc tgtaacctct tcagaggccc tcgctgccag   2760
ctctgtatca ggacccagag gaaggggcca gaggctcgtt gactggctgt gtgttgggat   2820
tgagtctgtg ccacgtgttt gtgctgtggt gtgtcccccct ctgtccaggc actgagatac   2880
cagcgaggag gctccagagg gcactctgct tgttattaga gattacctcc tgagaaaaaa   2940
ggttccgctt ggagcagagg ggctgaatag cagaaggttg cacctccccc aaccttagat   3000
gttctaagtc tttccattgg atctcattgg acccttccat ggtgtgatcg tctgactggt   3060
gttatcaccg tgggctccct gactgggagt tgatcgcctt tcccaggtgc tacacccttt   3120
tccagctgga tgagaatttg agtgctctga tccctctaca gagcttccct gactcattct   3180
gaaggagccc cattcctggg aaatattccc tagaaacttc caaatcccct aagcagacca   3240
ctgataaaac catgtagaaa atttgttatt ttgcaacctc gctggactct cagtctctga   3300
gcagtgaatg attcagtgtt aaatgtgatg aatactgtat tttgtattgt ttcaattgca   3360
tctcccagat aatgtgaaaa tggtccagga gaaggccaat tcctatacgc agcgtgcttt   3420
aaaaaataaa taagaaacaa ctctttgaga aacaacaatt tctactttga agtcatacca   3480
atgaaaaaat gtatatgcac ttataatttt cctaataaag ttctgtactc aaatgtagcc   3540
accaa                                                              3545
```

<210> SEQ ID NO 5
<211> LENGTH: 524
<212> TYPE: DNA
<213> ORGANISM: Homo sapiens

<400> SEQUENCE: 5

```
gccgcacttt cactctccgt cagccgcatt gcccgctcgg cgtccggccc ccgacccgcg     60
ctcgtccgcc cgcccgcccg cccgcccgcg ccatgaacgc caaggtcgtg gtcgtgctgg    120
```

```
tcctcgtgct gaccgcgctc tgcctcagcg acgggaagcc cgtcagcctg agctacagat    180

gcccatgccg attcttcgaa agccatgttg ccagagccaa cgtcaagcat ctcaaaattc    240

tcaacactcc aaactgtgcc cttcagattg tagcccggct gaagaacaac aacagacaag    300

tgtgcattga cccgaagcta aagtggattc aggagtacct ggagaaagct ttaaacaagg    360

ggcgcagaga agaaaaagtg gggaaaaaag aaaagatagg aaaaaagaag cgacagaaga    420

agagaaaggc tgcccagaaa aggaaaaact agttatctgc cacctcgaga tggaccacag    480

ttcacttgct ctcggcgctt tgtaaatttg ctcgatcctc ctcc                    524


<210> SEQ ID NO 6
<211> LENGTH: 1209
<212> TYPE: DNA
<213> ORGANISM: Homo sapiens

<400> SEQUENCE: 6

gccgcacttt cactctccgt cagccgcatt gcccgctcgg cgtccggccc ccgacccgcg     60

ctcgtccgcc cgcccgcccg cccgcccgcg ccatgaacgc caaggtcgtg gtcgtgctgg    120

tcctcgtgct gaccgcgctc tgcctcagcg acgggaagcc cgtcagcctg agctacagat    180

gcccatgccg attcttcgaa agccatgttg ccagagccaa cgtcaagcat ctcaaaattc    240

tcaacactcc aaactgtgcc cttcagattg tagcccggct gaagaacaac aacagacaag    300

tgtgcattga cccgaagcta aagtggattc aggagtacct ggagaaagct ttaaacaacc    360

tgatcagcgc cgcaccagcc gggaagaggg tgattgctgg ggctcgtgcc ctgcatccct    420

ctcctcccag ggcctgcccc acagctcggg ccctctgtga gatccgtctt tggcctcctc    480

cagaatggag ctggccctct cctggggatg tgtaatggtc cccctgctta cccgcaaaag    540

acaagtcttt acagaatcaa atgcaatttt aaatctgaga gctcgctttg agtgactggg    600

ttttgtgatt gcctctgaag cctatgtatg ccatggaggc actaacaaac tctgaggttt    660

ccgaaatcag aagcgaaaaa atcagtgaat aaaccatcat cttgccacta ccccctcctg    720

aagccacagc agggtttcag gttccaatca gaactgttgg caaggtgaca tttccatgca    780

taaatgcgat ccacagaagg tcctggtggt atttgtaact tttgcaagg catttttta    840

tatatatttt tgtgcacatt tttttttacg tttctttaga aaacaaatgt atttcaaaat    900

atatttatag tcgaacaatt catatatttg aagtggagcc atatgaatgt cagtagttta    960

tacttctcta ttatctcaaa ctactggcaa tttgtaaaga aatatatatg atatataaat   1020

gtgattgcag cttttcaatg ttagccacag tgtatttttt cacttgtact aaaattgtat   1080

caaatgtgac attatatgca ctagcaataa aatgctaatt gtttcatggt ataaacgtcc   1140

tactgtatgt gggaatttat ttacctgaaa taaaattcat tagttgttag tgatggagct   1200

taaaaaaaa                                                           1209


<210> SEQ ID NO 7
<211> LENGTH: 89
<212> TYPE: PRT
<213> ORGANISM: Homo sapiens

<400> SEQUENCE: 7

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
```

```
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85


<210> SEQ ID NO 8
<211> LENGTH: 93
<212> TYPE: PRT
<213> ORGANISM: Homo sapiens

<400> SEQUENCE: 8

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90


<210> SEQ ID NO 9
<211> LENGTH: 119
<212> TYPE: PRT
<213> ORGANISM: Homo sapiens

<400> SEQUENCE: 9

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Lys Arg Gln Lys Lys Arg Lys
            100                 105                 110

Ala Ala Gln Lys Arg Lys Asn
        115


<210> SEQ ID NO 10
<211> LENGTH: 140
<212> TYPE: PRT
<213> ORGANISM: Homo sapiens

<400> SEQUENCE: 10

Met Asn Ala Lys Val Val Val Val Leu Val Leu Val Leu Thr Ala Leu
1               5                   10                  15
```

-continued

```
Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn Leu Ile Ser Ala Ala Pro Ala
                85                  90                  95

Gly Lys Arg Val Ile Ala Gly Ala Arg Ala Leu His Pro Ser Pro Pro
            100                 105                 110

Arg Ala Cys Pro Thr Ala Arg Ala Leu Cys Glu Ile Arg Leu Trp Pro
        115                 120                 125

Pro Pro Glu Trp Ser Trp Pro Ser Pro Gly Asp Val
    130                 135                 140
```